United States Patent
Hirayama et al.

(10) Patent No.: US 12,152,027 B2
(45) Date of Patent: Nov. 26, 2024

(54) HETEROCYCLIC COMPOUND

(71) Applicant: Takeda Pharmaceutical Company Limited, Osaka (JP)

(72) Inventors: Takaharu Hirayama, Kanagawa (JP); Yoshiteru Ito, Kanagawa (JP); Noriyuki Nii, Kanagawa (JP); Youichi Kawakita, Kanagawa (JP); Shinichi Imamura, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 607 days.

(21) Appl. No.: 17/296,434

(22) PCT Filed: Nov. 27, 2019

(86) PCT No.: PCT/JP2019/046261
§ 371 (c)(1),
(2) Date: May 24, 2021

(87) PCT Pub. No.: WO2020/111087
PCT Pub. Date: Jun. 4, 2020

(65) Prior Publication Data
US 2022/0048916 A1    Feb. 17, 2022

(30) Foreign Application Priority Data

Nov. 28, 2018   (JP) ................... 2018-222530

(51) Int. Cl.
*C07D 487/04*   (2006.01)
*C07D 471/04*   (2006.01)

(52) U.S. Cl.
CPC ......... *C07D 471/04* (2013.01); *C07D 487/04* (2013.01)

(58) Field of Classification Search
CPC .................................................. C07D 487/04
USPC ......................................................... 544/236
See application file for complete search history.

(56) References Cited

U.S. PATENT DOCUMENTS 4,031,230 A    6/1977  Gottschlich et al.

FOREIGN PATENT DOCUMENTS

| JP | 2016-539975 A | 12/2016 | |
| WO | 1999015526 A2 | 4/1999 | |
| WO | 2015181747 A1 | 12/2015 | |
| WO | 2017081641 A1 | 5/2017 | |
| WO | 2018020474 A1 | 2/2018 | |
| WO | 2018085247 A1 | 5/2018 | |
| WO | 2018165385 A1 | 9/2018 | |
| WO | 2020111087 | * 11/2019 | |
| WO | WO-2020111087 A1 * | 6/2020 | ......... A61K 31/4375 |

OTHER PUBLICATIONS

International Search Report of PCT/JP2019/046261.

* cited by examiner

*Primary Examiner* — Niloofar Rahmani
(74) *Attorney, Agent, or Firm* — Sughrue Mion, PLLC

(57) ABSTRACT

Provided is a compound that can have an effect of inhibiting MALT1 and is expected as useful as a prophylactic or therapeutic drug for cancer, etc. A compound represented by formula (I) [wherein each symbol is as defined in the description], a salt thereof, or a cocrystal, a hydrate or a solvate of the same.

4 Claims, No Drawings
Specification includes a Sequence Listing.

SEQUENCE LISTING

<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: linker sequence

<400> SEQUENCE: 1
ggaagtggct caggtagc                                                     18

HETEROCYCLIC COMPOUND

CROSS REFERENCE TO RELATED APPLICATION

The present application is a U.S. National Stage Entry of the International Patent Application No. PCT/JP2019/046261, filed on Nov. 27, 2019, which claims priority to Japanese Application No. 2018-222530, filed on Nov. 28, 2018. The entire contents of those applications are incorporated herein for all purposes by this reference.

SEQUENCE LISTING

The instant application contains a Sequence Listing which has been submitted electronically in ASCII format and is hereby incorporated by reference in its entirety. Said ASCII copy, created on May 21, 2021, is named 051532-502N01US_SL.txt and is 420 bytes in size.

TECHNICAL FIELD

The present invention relates to a heterocyclic compound that can have an effect of inhibiting MALT1 (Mucosa associated lymphoid tissue protein 1) and is expected as useful as a prophylactic or therapeutic drug for cancer etc.

BACKGROUND ART

In the major T cells and B cells responsible for cell-mediated immunity, the T-cell receptor signal and B-cell receptor signal play important roles in their function. Transduction abnormality of these signals causes various diseases such as cancer and inflammatory disease. In fact, in the case of cancer, it has been reported that genetic analysis of patients with T cell-derived leukemia lymphoma such as ATL (adult T cell leukemia lymphoma), which is one of refractory lymphomas, reveals a genetic abnormality in the T-cell receptor signal/NF-κB pathway, and that the B-cell receptor signaling pathway/NF-κB pathway is also persistently activated in other B-cell lymphomas such as ABC-type DLBCL (diffuse large B-cell lymphoma) and MCL (mantle cell lymphoma).

A CBM protein complex in which these T-cell and B-cell receptor signals merge is composed of a scaffold protein CARD11, an adapter protein BCL10, and a MALT1 having paracaspase activity. The formation of the CBM protein complex is promoted by the T-cell receptor signal and the B-cell receptor signal, leading to an enhancement of the paracaspase activity of MALT1 and activating the transcription factor NF-κB.

Accordingly, an inhibitor that inhibits the activity of MALT1 is expected to be able to correct the enhancement of the activity of MALT1 caused by abnormalities in T-cell receptor signal and B-cell receptor signal, and is considered to be useful as a prophylactic or therapeutic drug for cancer, inflammatory disease and the like caused by the activity of MALT1.

The compound of the present invention is expected to be useful for prevention or treatment of diseases that may be affected by MALT1 (occasionally abbreviated as "MALT1-related diseases" in the description). It is expected to be useful for prevention or treatment of diseases including, but not limited to, cancer [for example, colorectal cancer (e.g., colon cancer, rectal cancer, anal cancer, familial colorectal cancer, hereditary nonpolyposis colorectal cancer and gastrointestinal stromal tumor), lung cancer (e.g., non-small cell lung cancer, small cell lung cancer and malignant mesothelioma), mesothelioma, pancreatic cancer (e.g., pancreatic ductal cancer and pancreatic endocrine tumor), pharyngeal cancer, laryngeal cancer, esophageal cancer, gastric cancer (e.g., papillary adenocarcinoma, mucinous adenocarcinoma and adenosquamous carcinoma), duodenal cancer, small intestine cancer, breast cancer (e.g., invasive ductal carcinoma, ductal carcinoma in situ, and inflammatory breast cancer), ovarian cancer (e.g., epithelial ovarian cancer, extragonadal germ cell tumor, ovarian germ cell tumor and low-grade ovarian tumor), testicular cancer, prostate cancer (e.g., hormone-dependent prostate cancer, hormone-independent prostate cancer and castration-resistant prostate cancer), liver cancer (e.g., hepatocellular carcinoma, primary liver cancer and extrahepatic cholangiocarcinoma), thyroid cancer (e.g., medullary thyroid cancer), renal cancer (e.g., renal cell carcinoma (e.g., clear cell renal cell carcinoma), transitional cell carcinoma of the renal pelvis and ureter), uterine cancer (e.g., cervical cancer, endometrial cancer and uterine sarcoma), gestational choriocarcinoma, brain tumor (e.g., medulloblastoma, glioma, pineal astrocytoma, pilocytic astrocytoma, diffuse astrocytoma, anaplastic astrocytoma and pituitary adenoma), retinoblastoma, skin cancer (e.g., basal cell carcinoma and malignant melanoma (e.g., melanoma)), sarcomas (e.g., rhabdomyosarcoma, leiomyosarcoma, soft tissue sarcoma, spindle cell sarcoma and osteosarcoma), malignant bone tumor, bladder cancer, hematological cancer (e.g., multiple myeloma, leukemia (e.g., acute myeloid leukemia and acute lymphocytic leukemia)), malignant lymphoma (e.g., diffuse large B-cell lymphoma, mantle cell lymphoma, adult T-cell leukemia/lymphoma and chronic myeloproliferative disorder), Hodgkin's disease, and cancer of unknown primary], inhibition of cancer growth, suppression of metastasis, promotion of apoptosis, or prevention or treatment of precancerous lesion (e.g., bone marrow atypia syndrome). In addition, the compound of the present invention is expected to be useful for prevention or treatment of autoimmune and/or inflammatory diseases (e.g., encephalomyelitis, colitis, atopic disease, rheumatoid arthritis, multiple sclerosis and systemic lupus erythematosus), bone disease, metabolic disease, neurological disease and neurodegenerative diseases, cancer, cardiovascular disease, allergies and asthma, Alzheimer's disease, hormone-related disease, inflammatory disease, viral infection (e.g., human immunodeficiency viral infections), and bacterial infection (e.g., sepsis).

Patent Literature 1 discloses the following compounds as compounds having an effect of inhibiting MALT1 and being useful for treating autoimmune disorders and inflammatory diseases such as rheumatoid arthritis, multiple sclerosis, systemic lupus erythematosus and vasculitis conditions, cancers derived from the haemopoietic system, including chronic myelogenous leukemia, myelogenous leukemia, non-Hodgkin's lymphoma and other B-cell lymphomas, or solid tumors and the like.

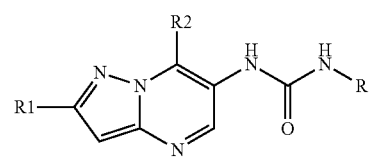

(I)

[wherein each symbol is as defined in the Literature.]

Patent Literature 2 discloses the following compounds as compounds having an effect of inhibiting MALT1 and being useful for treating autoimmune disorders and inflammatory diseases such as rheumatoid arthritis, multiple sclerosis, psoriasis, Sjogren's syndrome, systemic lupus erythematosus and vasculitis conditions, cancers derived from the haemopoietic system, including chronic myelogenous leukemia, myelogenous leukemia, non-Hodgkin's lymphoma and other B-cell lymphomas, or solid tumors and the like.

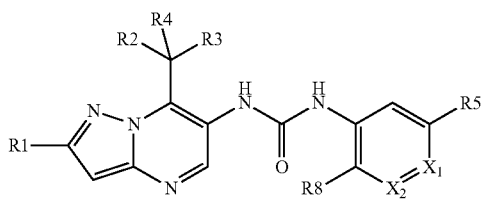

[wherein each symbol is as defined in the Literature.]

Patent Literature 3 discloses the following compounds as compounds having an effect of inhibiting MALT1 and being useful for treating autoimmune disorders, inflammatory diseases, cancers and the like.

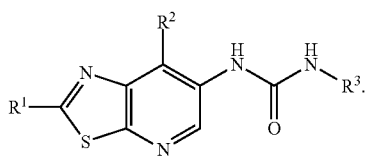

[wherein each symbol is as defined in the Literature.]

Patent Literature 4 discloses the following compounds as compounds having both effects of inhibiting MALT1 and promoting degradation of MALT1 protein through supplementation with E3 ubiquitin ligase, and being useful for treating cancers such as hematological cancer, lymphocytic malignant disease, leukemia, lymphoma and multiple myeloma, and the like.

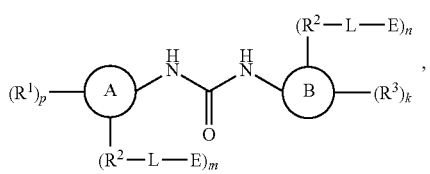

[wherein each symbol is as defined in the Literature.]

CITATIONS LIST

Patent Literatures

Patent Literature 1: WO 2015/181747
Patent Literature 2: WO 2017/081641
Patent Literature 3: WO 2018/020474
Patent Literature 4: WO 2018/085247

SUMMARY OF INVENTION

Technical Problems

An object of the present invention is to provide a novel compound that can have an effect of inhibiting MALT1 and is expected as useful as a prophylactic or therapeutic drug for cancer etc., and a medicine containing the same.

Solutions to Problems

As a result of diligent studies to solve the above problems, the present inventors have found that the compound represented by the following formula (I) can have an excellent effect of inhibiting MALT1, leading to completion of the present invention.

That is, the present invention is as follows.

[1] A compound represented by the formula (I):

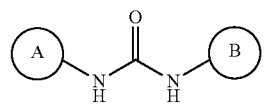

(wherein
A represents

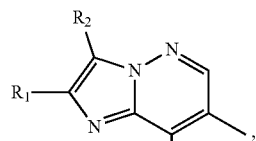

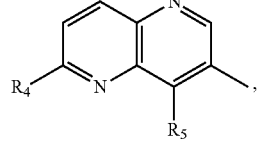

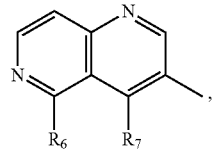

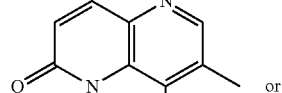

or

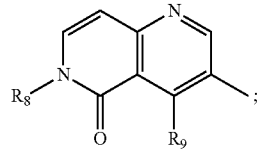

$R_1$ represents 1) a hydrogen atom, 2) a halogen atom, 3) a cyano group, 4) a $C_{1-3}$ alkyl group which may be substituted with 1 to 3 halogen atoms, 5) a $C_{1-3}$ alkoxy group, 6) a $C_{3-6}$ cycloalkyl group, or 7) a phenyl group;
$R_2$ represents 1) a hydrogen atom or 2) a halogen atom;

$R_3$ represents 1) a $C_{1-6}$ alkyl group which may be substituted with 1 to 3 substituents selected from a $C_{1-3}$ alkoxy group, a hydroxyl group and a halogen atom, 2) a pyrazolyl group which may be substituted with 1 to 3 substituents selected from a $C_{1-3}$ alkyl group and a halogen atom, 3) a $C_{3-6}$ cycloalkyl group, 4) an amino group di-substituted with a $C_{1-3}$ alkyl group, or 5) a phenyl group which may be substituted with 1 to 3 halogen atoms;

$R_4$ and $R_6$ represent 1) a hydrogen atom, 2) a halogen atom, 3) a $C_{1-3}$ alkyl group which may be substituted with 1 to 3 substituents selected from a) a hydroxyl group, b) a $C_{1-3}$ alkoxy group which may be substituted with a 4-methoxyphenyl group and c) a halogen atom, or 4) a $C_{1-3}$ alkoxy group which may be substituted with 1 to 3 halogen atoms;

$R_5$, $R_7$ and $R_9$ represent 1) a $C_{1-6}$ alkyl group which may be substituted with 1 to 3 $C_{1-3}$ alkoxy groups or 2) a phenyl group which may be substituted with 1 to 3 halogen atoms;

$R_8$ represents a $C_{1-3}$ alkyl group; and

B represents 1) a phenyl group which may be substituted with 1 to 3 substituents selected from a) a halogen atom, b) a cyano group, c) a $C_{1-3}$ alkoxy group which may be substituted with 1 to 3 halogen atoms, and d) a triazolyl group,
2) a $C_{3-6}$ cycloalkyl group which may be substituted with 1 to 3 substituents selected from a) a $C_{1-3}$ alkyl group which may be substituted with 1 to 3 halogen atoms and b) a halogen atom,
3) a pyridyl group which may be substituted with 1 to 3 substituents selected from a) a halogen atom, b) a cyano group, c) a $C_{1-3}$ alkyl group which may be substituted with 1 to 3 halogen atoms, d) a $C_{1-3}$ alkoxy group which may be substituted with 1 to 3 substituents selected from a halogen atom and a $C_{1-3}$ alkoxy group, e) a pyrazolyl group which may be substituted with 1 to 3 $C_{1-3}$ alkyl groups, f) an imidazolyl group which may be substituted with 1 to 3 $C_{1-3}$ alkyl groups, g) a triazolyl group which may be substituted with 1 to 3 $C_{1-3}$ alkyl groups which may be substituted with 1 to 3 substituents selected from a $C_{1-3}$ alkoxy group and a halogen atom, h) an azetidinyl group, i) a pyrrolidonyl group, j) a tetrazolyl group which may be substituted with 1 to 3 $C_{1-3}$ alkyl groups, k) a pyrimidinyl group, and l) an oxazolyl group,
4) a pyrazolyl group which may be substituted with 1 to 3 substituents selected from a) a $C_{1-3}$ alkyl group which may be substituted with 1 to 3 halogen atoms, b) a $C_{1-3}$ alkoxy group which may be substituted with 1 to 3 halogen atoms, c) a cyano group, and d) a halogen atom, or
5) an imidazopyridyl group which may be substituted with 1 to 3 halogen atoms)

or a salt thereof, or a co-crystal, a hydrate or a solvate thereof (sometimes abbreviated as "Compound (I)" in the description).

[2] The compound according to [1], wherein A is

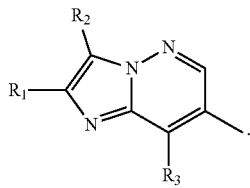

[3] The compound according to [1], wherein A is

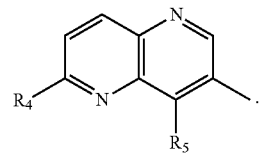

[4] The compound according to [1], wherein A is

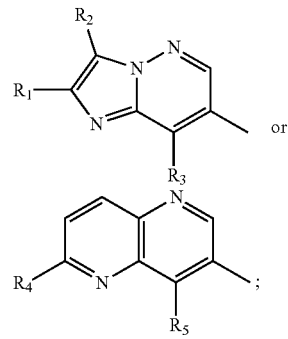

$R_1$ is 1) a halogen atom or 2) a $C_{1-3}$ alkyl group;

$R_2$ is a hydrogen atom;

$R_3$ is a $C_{1-6}$ alkyl group which may be substituted with 1 to 3 $C_{1-3}$ alkoxy groups;

$R_4$ is 1) a halogen atom or 2) a $C_{1-3}$ alkyl group;

$R_5$ is a $C_{1-6}$ alkyl group which may be substituted with 1 to 3 $C_{1-3}$ alkoxy groups; and B is a pyridyl group which may be substituted with 1 to 3 substituents selected from a) a halogen atom, b) a cyano group, c) a $C_{1-3}$ alkyl group which may be substituted with 1 to 3 halogen atoms, d) a $C_{1-3}$ alkoxy group which may be substituted with 1 to 3 halogen atoms, and e) a triazolyl group.

[5] The compound according to [1], being (S)-N-(5-chloro-6-(difluoromethoxy)pyridin-3-yl)-N'-(8-(1-methoxyethyl)-2-methylimidazo[1,2-b]pyridazin-7-yl)urea, (S)-N-(6-chloro-4-(1-methoxyethyl)-1,5-naphthyridin-3-yl)-N'-(6-(2H-1,2,3-triazol-2-yl)-5-(trifluoromethyl)pyridin-3-yl)urea, (S)-N-(4-(1-methoxyethyl)-6-methyl-1,5-naphthyridin-3-yl)-N'-(6-(2H-1,2,3-triazol-2-yl)-5-(trifluoromethyl)pyridin-3-yl)urea, (S)-N-(5-chloro-6-(2H-1,2,3-triazol-2-yl)pyridin-3-yl)-N'-(8-(1-methoxyethyl)-2-methylimidazo[1,2-b]pyridazin-7-yl)urea, (S)-N-(5-cyano-6-(difluoromethoxy)pyridin-3-yl)-N'-(8-(1-methoxyethyl)-2-methylimidazo[1,2-b]pyridazin-7-yl)urea, (S)-N-(8-(1-methoxyethyl)-2-methylimidazo[1,2-b]pyridazin-7-yl)-N'-(6-(2H-1,2,3-triazol)-2-yl)-5-(trifluoromethylpyridin-3-yl)urea, N-(5-chloro-6-(2H-1,2,3-triazol-2-yl)pyridin-3-yl)-N'-(8-(2-methoxypropan-2-yl)-2-methylimidazo[1,2-b]pyridazin-7-yl)urea, N-(5-chloro-6-(difluoromethoxy)pyridin-3-yl)-N'-(2-chloro-8-(propan-2-yl)imidazo[1,2-b]pyridazin-7-yl)urea, or N-(5-chloro-6-(2H-1,2,3-triazol-2-yl)pyridin-3-yl)-N'-(2-methyl-8-(propan-2-yl)imidazo[1,2-b]pyridazin-7-yl)urea.

[6] The compound according to [1], being (S)-N-(5-chloro-6-(difluoromethoxy)pyridin-3-yl)-N'-(8-(1-methoxyethyl)-2-methylimidazo[1,2-b]pyridazin-7-yl)urea.
[7] The compound according to [1], being (S)-N-(6-chloro-4-(1-methoxyethyl)-1,5-naphthyridin-3-yl)-N'-(6-(2H-1,2,3-triazol-2-yl)-5-(trifluoromethyl)pyridin-3-yl)urea.
[8] A medicine containing the compound according to [1], or a salt thereof, or a co-crystal, a hydrate or a solvate thereof.
[9] The medicine according to [8], being a MALT1 inhibitor.
[10] The medicine according to [8], being a prophylactic or therapeutic drug for cancer.

Advantageous Effects of Invention

The compound of the present invention can have an effect of inhibiting MALT1 and be useful as a medicine such as a prophylactic or therapeutic drug for cancer etc.

DESCRIPTION OF EMBODIMENTS

Hereinafter, a detailed description is made of the definition of each substituent used in the description. Unless otherwise specified, each substituent has the following definition.

In the description, examples of the "halogen atom" include fluorine, chlorine, bromine and iodine.

In the description, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the description, examples of the "$C_{3-6}$ cycloalkyl group" include cyclopropyl, cyclobutyl, cyclopentyl and cyclohexyl.

In the description, examples of the "$C_{1-3}$ alkoxy group" include methoxy, ethoxy, propoxy and isopropoxy.

In the description, examples of the "amino group disubstituted with a $C_{1-3}$ alkyl group" include dimethylamino, ethylmethylamino, diethylamino, ethylpropylamino and dipropylamino.

In the description, the "$C_{1-3}$ alkyl group" includes the above "$C_{1-6}$ alkyl group" having 1 to 3 carbon atoms.

Hereinafter, a detailed description is made of the definition of each symbol in the formula (I).

A represents

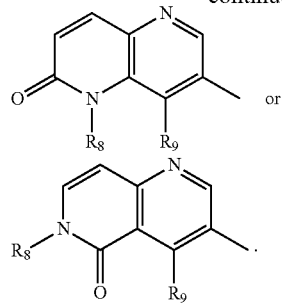,

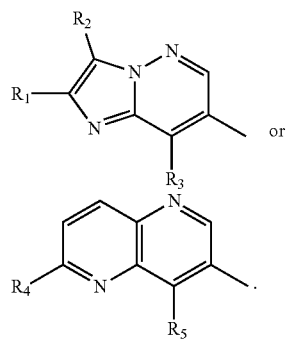,

,

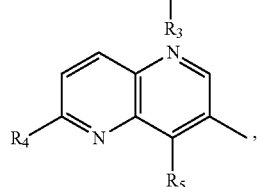,

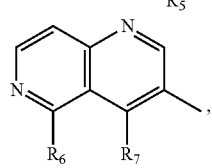

-continued

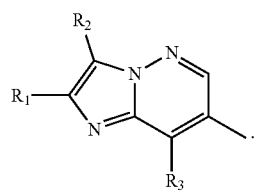 or

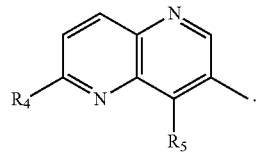.

A is preferably

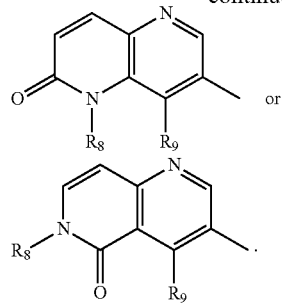 or

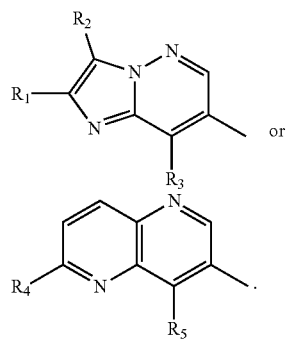.

In one preferred embodiment of the invention, A is

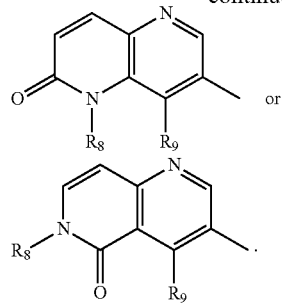.

In another preferred embodiment of the present invention, A is

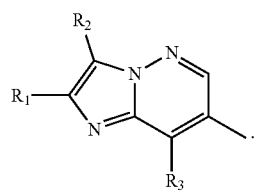.

$R_1$ represents 1) a hydrogen atom, 2) a halogen atom (e.g., chlorine atom, bromine atom), 3) a cyano group, 4) a $C_{1-3}$ alkyl group (e.g., methyl) which may be substituted with 1 to 3 halogen atoms (e.g., fluorine atom), 5) a $C_{1-3}$ alkoxy group (e.g., methoxy), 6) a $C_{3-6}$ cycloalkyl group (e.g., cyclopropyl), or 7) a phenyl group.

$R_1$ is more preferably 1) a halogen atom (e.g., chlorine atom) or 2) a $C_{1-3}$ alkyl group (e.g., methyl).

$R_2$ represents 1) a hydrogen atom or 2) a halogen atom (e.g., fluorine atom, chlorine atom).

$R_2$ is preferably a hydrogen atom.

$R_3$ represents 1) a $C_{1-6}$ alkyl group (e.g., ethyl, isopropyl, sec-butyl) which may be substituted with 1 to 3 substituents selected from a $C_{1-3}$ alkoxy group (e.g., methoxy), a hydroxyl group and a halogen atom (e.g., fluorine atom), 2) a pyrazolyl group (e.g., 4-pyrazolyl) which may be substituted with 1 to 3 substituents selected from a $C_{1-3}$ alkyl group (e.g., methyl) and a halogen atom (e.g., a chlorine atom), 3) a $C_{3-6}$ cycloalkyl group (e.g., cyclopropyl), 4) an amino group di-substituted with a $C_{1-3}$ alkyl group (e.g., methyl), or 5) a phenyl group which may be substituted with 1 to 3 halogen atoms (e.g., chlorine atom).

$R_3$ is preferably a $C_{1-6}$ alkyl group (e.g., ethyl, isopropyl) which may be substituted with 1 to 3 $C_{1-3}$ alkoxy groups (e.g., methoxy).

$R_4$ and $R_6$ represent 1) a hydrogen atom, 2) a halogen atom (e.g., chlorine atom), 3) a Cl-3 alkyl group (e.g., methyl, ethyl) which may be substituted with 1 to 3 substituents selected from a) a hydroxyl group, b) a $C_{1-3}$ alkoxy group (e.g., methoxy) which may be substituted with a 4-methoxyphenyl group and c) a halogen atom (e.g., fluorine atom), or 4) a $C_{1-3}$ alkoxy group (e.g., methoxy, ethoxy) which may be substituted with 1 to 3 halogen atoms (e.g., fluorine atom).

$R_4$ is preferably 1) a halogen atom (e.g., chlorine atom) or 2) a $C_{1-3}$ alkyl group (e.g., methyl).

$R_6$ is preferably 1) a hydrogen atom, 2) a halogen atom (e.g., chlorine atom), 3) a $C_{1-3}$ alkyl group (e.g., methyl) or 4) a $C_{1-3}$ alkoxy group (e.g., methoxy).

$R_5$, $R_7$ and $R_9$ represent 1) a $C_{1-6}$ alkyl group (e.g., ethyl, isopropyl) which may be substituted with 1 to 3 $C_{1-3}$ alkoxy groups (e.g., methoxy, ethoxy) or 2) a phenyl group which may be substituted with 1 to 3 halogen atoms (e.g., chlorine atom).

$R_5$ is preferably a $C_{1-6}$ alkyl group (e.g., ethyl) which may be substituted with 1 to 3 $C_{1-3}$ alkoxy groups (e.g., methoxy).

$R_7$ is preferably 1) a $C_{1-6}$ alkyl group (e.g., ethyl, isopropyl) which may be substituted with 1 to 3 $C_{1-3}$ alkoxy groups (e.g., methoxy) or 2) a phenyl group which may be substituted with 1 to 3 halogen atoms (e.g., chlorine atom).

$R_9$ is preferably a $C_{1-3}$ alkyl group (e.g., ethyl) which may be substituted with 1 to 3 $C_{1-3}$ alkoxy groups (e.g., methoxy).

$R_8$ represents a $C_{1-3}$ alkyl group (e.g., methyl).

B represents
1) a phenyl group which may be substituted with 1 to 3 substituents selected from a) a halogen atom (e.g., fluorine atom, chlorine atom), b) a cyano group, c) a $C_{1-3}$ alkoxy group (e.g., methoxy) which may be substituted with 1 to 3 halogen atoms (e.g., fluorine atom), and d) a triazolyl group,
2) a $C_{3-6}$ cycloalkyl group (e.g., cyclohexyl) which may be substituted with 1 to 3 substituents selected from a) a $C_{1-3}$ alkyl group (e.g., methyl) which may be substituted with 1 to 3 halogen atoms (e.g., fluorine atom) and b) a halogen atom (e.g., fluorine atom),
3) a pyridyl group which may be substituted with 1 to 3 substituents selected from a) a halogen atom (e.g., fluorine atom, chlorine atom, bromine atom), b) a cyano group, c) a $C_{1-3}$ alkyl group (e.g., methyl) which may be substituted with 1 to 3 halogen atoms (e.g., fluorine atom), d) a $C_{1-3}$ alkoxy group (e.g., methoxy, ethoxy) which may be substituted with 1 to 3 substituents selected from a halogen atom (e.g., fluorine atom) and a $C_{1-3}$ alkoxy group (e.g., methoxy), e) a pyrazolyl group which may be substituted with 1 to 3 $C_{1-3}$ alkyl groups (e.g., methyl), f) an imidazolyl group which may be substituted with 1 to 3 $C_{1-3}$ alkyl groups (e.g., methyl), g) a triazolyl group which may be substituted with 1 to 3 $C_{1-3}$ alkyl groups (e.g., methyl) which may be substituted with 1 to 3 substituents selected from a $C_{1-3}$ alkoxy group (e.g., methoxy) and a halogen atom (e.g., fluorine atom), h) an azetidinyl group, i) a pyrolidonyl group, j) a tetrazolyl group which may be substituted with 1 to 3 $C_{1-3}$ alkyl groups (e.g., methyl), k) a pyrimidinyl group, and l) an oxazolyl group,
4) a pyrazolyl group which may be substituted with 1 to 3 substituents selected from a) a $C_{1-3}$ alkyl group (e.g., methyl, ethyl, isopropyl) which may be substituted with 1 to 3 halogen atoms (e.g., fluorine atom), b) a $C_{1-3}$ alkoxy group (e.g., methoxy) which may be substituted with 1 to 3 halogen atoms (e.g., fluorine atom), c) a cyano group, and d) a halogen atom (e.g., chlorine atom), or
5) an imidazopyridyl group which may be substituted with 1 to 3 halogen atoms (e.g., chlorine atom).

B is preferably a pyridyl group which may be substituted with 1 to 3 substituents selected from a) a halogen atom (e.g., chlorine atom), b) a cyano group, c) a $C_{1-3}$ alkyl group (e.g., methyl) which may be substituted with 1 to 3 halogen atoms (e.g., fluorine atom), d) a $C_{1-3}$ alkoxy group (e.g., methoxy) which may be substituted with 1 to 3 halogen atoms (e.g., fluorine atom), and e) a triazolyl group.

Suitable examples of the compound (I) include the following compounds.

[Compound I-1]

The compound (I), wherein A is

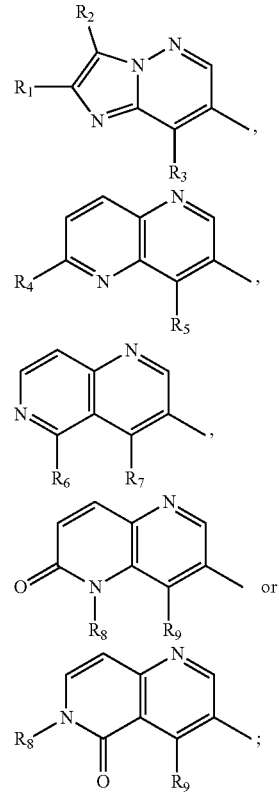

$R_1$ is 1) a hydrogen atom, 2) a halogen atom (e.g., chlorine atom, bromine atom), 3) a cyano group, 4) a $C_{1-3}$ alkyl group (e.g., methyl) which may be substituted with 1 to 3 halogen atoms (e.g., fluorine atom), 5) a $C_{1-3}$ alkoxy group (e.g., methoxy), 6) a $C_{3-6}$ cycloalkyl group (e.g., cyclopropyl), or 7) a phenyl group;

$R_2$ is 1) a hydrogen atom or 2) a halogen atom (e.g., fluorine atom, chlorine atom);

$R_3$ is 1) a $C_{1-6}$ alkyl group (e.g., ethyl, isopropyl, sec-butyl) which may be substituted with 1 to 3 substituents selected from a $C_{1-3}$ alkoxy group (e.g., methoxy), a hydroxyl group and a halogen atom (e.g., fluorine atom), 2) a pyrazolyl group (e.g., 4-pyrazolyl) which may be substituted with 1 to 3 substituents selected from a $C_{1-3}$ alkyl group (e.g., methyl) and a halogen atom (e.g., a chlorine atom), 3) a $C_{3-6}$ cycloalkyl group (e.g., cyclopropyl), 4) an amino group di-substituted with a $C_{1-3}$ alkyl group (e.g., methyl), or 5) a phenyl group which may be substituted with 1 to 3 halogen atoms (e.g., chlorine atom);

$R_4$ is 1) a hydrogen atom, 2) a halogen atom (e.g., chlorine atom), 3) a $C_{1-3}$ alkyl group (e.g., methyl, ethyl) which may be substituted with 1 to 3 substituents selected from a) a hydroxyl group, b) a $C_{1-3}$ alkoxy group (e.g., methoxy) which may be substituted with a 4-methoxyphenyl group and c) a halogen atom (e.g., fluorine atom), or 4) a $C_{1-3}$ alkoxy group (e.g., methoxy, ethoxy) which may be substituted with 1 to 3 halogen atoms (e.g., fluorine atom);

$R_5$ is 1) a $C_{1-6}$ alkyl group (e.g., ethyl, isopropyl) which may be substituted with 1 to 3 $C_{1-3}$ alkoxy groups (e.g., methoxy, ethoxy) or 2) a phenyl group which may be substituted with 1 to 3 halogen atoms (e.g., chlorine atom);

$R_6$ is 1) a hydrogen atom, 2) a halogen atom (e.g., chlorine atom), 3) a $C_{1-3}$ alkyl group (e.g., methyl) or 4) a $C_{1-3}$ alkoxy group (e.g., ethoxy);

$R_7$ is 1) a $C_{1-6}$ alkyl group (ethyl, isopropyl) which may be substituted with 1 to 3 $C_{1-3}$ alkoxy groups (e.g., methoxy) or 2) a phenyl group which may be substituted with 1 to 3 halogen atoms (e.g., chlorine atom);

$R_8$ is a $C_{1-3}$ alkyl group (e.g., methyl);

$R_9$ is a $C_{1-3}$ alkyl group (e.g., ethyl) which may be substituted with 1 to 3 $C_{1-3}$ alkoxy groups (e.g., methoxy); and B is 1) a phenyl group which may be substituted with 1 to 3 substituents selected from a) a halogen atom (e.g., fluorine atom, chlorine atom), b) a cyano group, c) a $C_{1-3}$ alkoxy group (e.g., methoxy) which may be substituted with 1 to 3 halogen atoms (e.g., fluorine atom), and d) a triazolyl group, 2) a $C_{3-6}$ cycloalkyl group (e.g., cyclohexyl) which may be substituted with 1 to 3 substituents selected from a) a $C_{1-3}$ alkyl group (e.g., methyl) which may be substituted with 1 to 3 halogen atoms (e.g., fluorine atom) and b) a halogen atom (e.g., fluorine atom), 3) a pyridyl group which may be substituted with 1 to 3 substituents selected from a) a halogen atom (e.g., fluorine atom, chlorine atom, bromine atom), b) a cyano group, c) a $C_{1-3}$ alkyl group (e.g., methyl) which may be substituted with 1 to 3 halogen atoms (e.g., fluorine atom), d) a $C_{1-3}$ alkoxy group (e.g., methoxy, ethoxy) which may be substituted with 1 to 3 substituents selected from a halogen atom (e.g., fluorine atom) and a $C_{1-3}$ alkoxy group (e.g., methoxy), e) a pyrazolyl group which may be substituted with 1 to 3 $C_{1-3}$ alkyl groups (e.g., methyl), f) an imidazolyl group which may be substituted with 1 to 3 $C_{1-3}$ alkyl groups (e.g., methyl), g) a triazolyl group which may be substituted with 1 to 3 $C_{1-3}$ alkyl groups (e.g., methyl) which may be substituted with 1 to 3 substituents selected from a $C_{1-3}$ alkoxy group (e.g., methoxy) and a halogen atom (e.g., fluorine atom), h) an azetidinyl group, i) a pyrrolidonyl group, j) a tetrazolyl group which may be substituted with 1 to 3 $C_{1-3}$ alkyl groups (e.g., methyl), k) a pyrimidinyl group, and l) an oxazolyl group, 4) a pyrazolyl group which may be substituted with 1 to 3 substituents selected from a) a $C_{1-3}$ alkyl group (e.g., methyl, ethyl, isopropyl) which may be substituted with 1 to 3 halogen atoms (e.g., fluorine atom), b) a $C_{1-3}$ alkoxy group (e.g., methoxy) which may be substituted with 1 to 3 halogen atoms (e.g., fluorine atom), c) a cyano group, and d) a halogen atom (e.g., chlorine atom), or 5) an imidazopyridyl group which may be substituted with 1 to 3 halogen atoms (e.g., chlorine atom).

[Compound I-2]

The compound (I), wherein A is

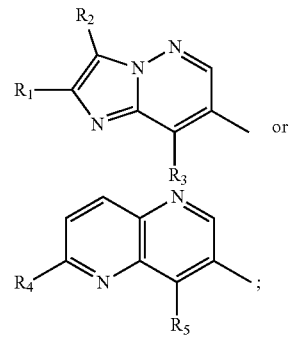

or $R_1$ is 1) a halogen atom (e.g., chlorine atom) or 2) a $C_{1-3}$ alkyl group (e.g., methyl);

$R_2$ is a hydrogen atom;

$R_3$ is a $C_{1-6}$ alkyl group (e.g., ethyl, isopropyl) which may be substituted with 1 to 3 $C_{1-3}$ alkoxy groups (e.g., methoxy);

$R_4$ is 1) a halogen atom (e.g., chlorine atom) or 2) a $C_{1-3}$ alkyl group (e.g., methyl);

$R_5$ is a $C_{1-6}$ alkyl group (e.g., ethyl) which may be substituted with 1 to 3 $C_{1-3}$ alkoxy groups (e.g., methoxy); and B is a pyridyl group which may be substituted with 1 to 3 substituents selected from a) a halogen atom (e.g., chlorine atom), b) a cyano group, c) a $C_{1-3}$ alkyl group (e.g., methyl) which may be substituted with 1 to 3 halogen atoms (e.g., fluorine atom), d) a $C_{1-3}$ alkoxy group (e.g., methoxy) which may be substituted with 1 to 3 halogen atoms (e.g., fluorine atom), and e) a triazolyl group.

[Compound I-3]

The compound (I), wherein A is

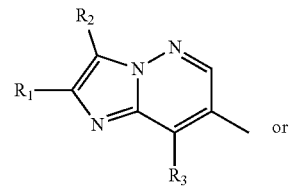

or

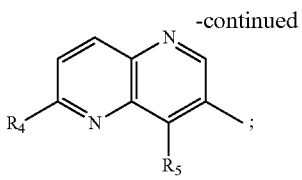

R₁ is a C₁₋₃ alkyl group (e.g., methyl);
R₂ is a hydrogen atom;
R₃ is a C₁₋₆ alkyl group (e.g., ethyl, isopropyl) which is substituted with 1 to 3 C₁₋₃ alkoxy groups (e.g., methoxy);
R₄ is 1) a halogen atom (e.g., chlorine atom) or 2) a C₁₋₃ alkyl group (e.g., methyl);
R₅ is a C₁₋₆ alkyl group (e.g., ethyl) which may be substituted with 1 to 3 C₁₋₃ alkoxy groups (e.g., methoxy); and
B is a pyridyl group which may be substituted with 1 to 3 substituents selected from a) a halogen atom (e.g., chlorine atom), b) a C₁₋₃ alkyl group (e.g., methyl) which may be substituted with 1 to 3 halogen atoms (e.g., fluorine atom), c) a C₁₋₃ alkoxy group (e.g., methoxy) which may be substituted with 1 to 3 halogen atoms (e.g., fluorine atom), and d) a triazolyl group.

[Compound I-4]
The compound (I), wherein A is

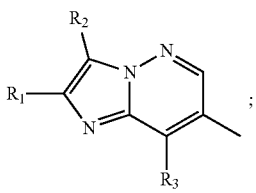

R₁ is 1) a hydrogen atom, 2) a halogen atom (e.g., chlorine atom, bromine atom), 3) a cyano group, 4) a C₁₋₃ alkyl group (e.g., methyl) which may be substituted with 1 to 3 halogen atoms (e.g., fluorine atom), 5) a C₁₋₃ alkoxy group (e.g., methoxy), 6) a C₃₋₆ cycloalkyl group (e.g., cyclopropyl), or 7) a phenyl group;
R₂ is 1) a hydrogen atom or 2) a halogen atom (e.g., fluorine atom, chlorine atom);
R₃ is 1) a C₁₋₆ alkyl group (e.g., ethyl, isopropyl, sec-butyl) which may be substituted with 1 to 3 substituents selected from a C₁₋₃ alkoxy group (e.g., methoxy), a hydroxyl group and a halogen atom (e.g., fluorine atom), 2) a pyrazolyl group (e.g., 4-pyrazolyl) which may be substituted with 1 to 3 substituents selected from a C₁₋₃ alkyl group (e.g., methyl) and a halogen atom (e.g., a chlorine atom), 3) a C₃₋₆ cycloalkyl group (e.g., cyclopropyl), 4) an amino group di-substituted with a C₁₋₃ alkyl group (e.g., methyl), or 5) a phenyl group which may be substituted with 1 to 3 halogen atoms (e.g., chlorine atom); and
B is
1) a phenyl group which may be substituted with 1 to 3 substituents selected from a) a halogen atom (e.g., fluorine atom, chlorine atom), b) a cyano group, c) a C₁₋₃ alkoxy group (e.g., methoxy) which may be substituted with 1 to 3 halogen atoms (e.g., fluorine atom), and d) a triazolyl group,
2) a pyridyl group which may be substituted with 1 to 3 substituents selected from a) a halogen atom (e.g., chlorine atom, bromine atom), b) a cyano group, c) a C₁₋₃ alkyl group (e.g., methyl) which may be substituted with 1 to 3 halogen atoms (e.g., fluorine atom), d) a C₁₋₃ alkoxy group (e.g., methoxy) which may be substituted with 1 to 3 halogen atoms (e.g., fluorine atom), e) a pyrazolyl group which may be substituted with 1 to 3 C₁₋₃ alkyl groups (e.g., methyl), f) an imidazolyl group which may be substituted with 1 to 3 C₁₋₃ alkyl groups (e.g., methyl), g) a triazolyl group which may be substituted with 1-3 C₁₋₃ alkyl groups (e.g., methyl) which may be substituted with 1 to 3 substituents selected from a C₁₋₃ alkoxy group (e.g., methoxy) and a halogen atom (e.g., fluorine atom), and
h) an oxazolyl group,
3) a pyrazolyl group which may be substituted with 1 to 3 substituents selected from a) a C₁₋₃ alkyl group (e.g., methyl) which may be substituted with 1 to 3 halogen atoms (e.g., fluorine atom), b) a C₁₋₃ alkoxy group (e.g., methoxy) which may be substituted with 1 to 3 halogen atoms (e.g., fluorine atom), c) a cyano group, and d) a halogen atom (e.g., chlorine atom), or
4) an imidazopyridyl group which may be substituted with 1 to 3 halogen atoms (e.g., chlorine atom).

[Compound I-5]
The compound (I), wherein A is

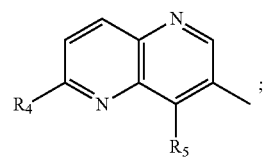

R₄ is 1) a hydrogen atom, 2) a halogen atom (e.g., chlorine atom), 3) a C₁₋₃ alkyl group (e.g., methyl, ethyl) which may be substituted with 1 to 3 substituents selected from a) a hydroxyl group, b) a C₁₋₃ alkoxy group (e.g., methoxy) which may be substituted with a 4-methoxyphenyl group and c) a halogen atom (e.g., fluorine atom), or 4) a C₁₋₃ alkoxy group (e.g., methoxy, ethoxy) which may be substituted with 1 to 3 halogen atoms (e.g., fluorine atom);
R₅ is 1) a C₁₋₆ alkyl group (e.g., ethyl, isopropyl) which may be substituted with 1 to 3 C₁₋₃ alkoxy groups (e.g., methoxy, ethoxy) or 2) a phenyl group which may be substituted with 1 to 3 halogen atoms (e.g., chlorine atom); and
B is
1) a phenyl group which may be substituted with 1 to 3 halogen atoms (e.g., fluorine atom),
2) a C₃₋₆ cycloalkyl group (e.g., cyclohexyl) which may be substituted with 1 to 3 substituents selected from a) a C₁₋₃ alkyl group (e.g., methyl) which may be substituted with 1 to 3 halogen atoms (e.g., fluorine atom) and b) a halogen atom (e.g., fluorine atom),
3) a pyridyl group which may be substituted with 1 to 3 substituents selected from a) a halogen atom (e.g., fluorine atom, chlorine atom, bromine atom), b) a cyano group, c) a C₁₋₃ alkyl group (e.g., methyl) which may be substituted with 1 to 3 halogen atoms (e.g., fluorine atom), d) a C₁₋₃ alkoxy group (e.g., methoxy, ethoxy) which may be substituted with 1 to 3 substituents selected from a halogen atom (e.g., fluorine atom) and a C₁₋₃ alkoxy group (e.g., methoxy), e) a triazolyl group which may be substituted with 1 to 3 C₁₋₃ alkyl groups (e.g., methyl) which may be substituted with 1 to 3 substituents selected from a $C_{1-3}$ alkoxy group (e.g., methoxy) and a halogen atom (e.g., fluorine atom), f) an azetidinyl group, g) a pyrrolidonyl group, h) a tetrazolyl group which may be substituted with 1 to 3 substituents selected from a $C_{1-3}$ alkyl group (e.g., methyl), i) a pyrimidinyl group, and j) an oxazolyl group, or 4) a pyrazolyl group which may be substituted with 1 to 3 $C_{1-3}$ alkyl groups (e.g., methyl, ethyl, isopropyl) which may be substituted with 1 to 3 halogen atoms (e.g., fluorine atom).

[Compound I-6]

The compound (I), wherein A is

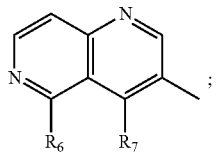

$R_6$ is 1) a hydrogen atom, 2) a halogen atom (e.g., chlorine atom), 3) a $C_{1-3}$ alkyl group (e.g., methyl) or 4) a $C_{1-3}$ alkoxy group (e.g., ethoxy);

$R_7$ is 1) a $C_{1-6}$ alkyl group (ethyl, isopropyl) which may be substituted with 1 to 3 $C_{1-3}$ alkoxy groups (e.g., methoxy) or 2) a phenyl group which may be substituted with 1 to 3 halogen atoms (e.g., chlorine atom); and B is 1) a phenyl group which may be substituted with 1 to 3 halogen atoms (e.g., fluorine atom), or 2) a pyridyl group which may be substituted with 1 to 3 substituents selected from a) a halogen atom (e.g., chlorine atom), b) a cyano group, c) a $C_{1-3}$ alkyl group (e.g., methyl) which may be substituted with 1 to 3 halogen atoms (e.g., fluorine atom), d) a $C_{1-3}$ alkoxy group (e.g., methoxy) which may be substituted with 1 to 3 halogen atoms (e.g., fluorine atom), and e) a triazolyl group.

[Compound I-7]

The compound (I), wherein A is

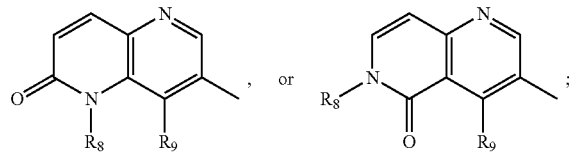

$R_8$ is a $C_{1-3}$ alkyl group (e.g., methyl);

$R_9$ is a $C_{1-3}$ alkyl group (e.g., ethyl) which may be substituted with 1 to 3 $C_{1-3}$ alkoxy groups (e.g., methoxy); and B is a pyridyl group which may be substituted with 1 to 3 substituents selected from a) a halogen atom (e.g., chlorine atom), b) a $C_{1-3}$ alkyl group (e.g., methyl) which may be substituted with 1 to 3 halogen atoms (e.g., fluorine atom), c) a $C_{1-3}$ alkoxy group (e.g., methoxy), and d) a triazolyl group.

[Compound I-8]

(S)-N-(5-chloro-6-(difluoromethoxy)pyridin-3-yl)-N'-(8-(1-methoxyethyl)-2-methylimidazo[1,2-b]pyridazin-7-yl)urea, (S)-N-(6-chloro-4-(1-methoxyethyl)-1,5-naphthyridin-3-yl)-N'-(6-(2H-1,2,3-triazol-2-yl)-5-(trifluoromethyl)pyridin-3-yl)urea, (S)-N-(4-(1-methoxyethyl)-6-methyl-1,5-naphthyridin-3-yl)-N'-(6-(2H-1,2,3-triazol-2-yl)-5-(trifluoromethyl)pyridin-3-yl)urea, (S)-N-(5-chloro-6-(2H-1,2,3-triazol-2-yl)pyridin-3-yl)-N'-(8-(1-methoxyethyl)-2-methylimidazo[1,2-b]pyridazin-7-yl)urea, (S)-N-(5-cyano-6-(difluoromethoxy)pyridin-3-yl)-N'-(8-(1-methoxyethyl)-2-methylimidazo[1,2-b]pyridazin-7-yl)urea, (S)-N-(8-(1-methoxyethyl)-2-methylimidazo[1,2-b]pyridazin-7-yl)-N'-(6-(2H-1,2,3-triazol-2-yl)-5-(trifluoromethyl)pyridin-3-yl)urea, N-(5-chloro-6-(2H-1,2,3-triazol-2-yl)pyridin-3-yl)-N'-(8-(2-methoxypropan-2-yl)-2-methylimidazo[1,2-b]pyridazin-7-yl)urea, N-(5-chloro-6-(difluoromethoxy)pyridin-3-yl)-N'-(2-chloro-8-(propan-2-yl)imidazo[1,2-b]pyridazin-7-yl)urea, or N-(5-chloro-6-(2H-1,2,3-triazol-2-yl)pyridin-3-yl)-N'-(2-methyl-8-(propan-2-yl)imidazo[1,2-b]pyridazin-7-yl)urea.

[Compound I-9]

(S)-N-(5-chloro-6-(difluoromethoxy)pyridin-3-yl)-N'-(8-(1-methoxyethyl)-2-methylimidazo[1,2-b]pyridazin-7-yl)urea, or (S)-N-(6-chloro-4-(1-methoxyethyl)-1,5-naphthyridin-3-yl)-N'-(6-(2H-1,2,3-triazol-2-yl)-5-(trifluoromethyl)pyridin-3-yl)urea.

The salt of the compound represented by the formula (I) is preferably a pharmacologically acceptable salt. Examples of such a salt include salts with inorganic bases, salts with organic bases, salts with inorganic acids, salts with organic acids, and salts with basic or acidic amino acids.

Suitable examples of the salts with inorganic bases include alkali metal salts such as sodium salt and potassium salt; alkaline earth metal salts such as calcium salt and magnesium salt; aluminum salt; and ammonium salt.

Suitable examples of the salts with organic bases include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine and N,N-dibenzylethylenediamine.

Suitable examples of the salts with inorganic acids include salts with hydrogen chloride, hydrogen bromide, nitric acid, sulfuric acid and phosphoric acid.

Suitable examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid and p-toluenesulfonic acid.

Suitable examples of the salts with basic amino acids include salts with arginine, lysine and ornithine.

Suitable examples of the salts with acidic amino acids include salts with aspartic acid and glutamic acid.

Hereinafter, a description is made of the method for producing the compound of the present invention.

The raw materials and reagents used in each step in the following producing methods, and the obtained compounds may each form a salt. Examples of such a salt include those similar to the above-mentioned salts of the compound of the present invention.

When the compound obtained in each step is a free compound, it can be converted into a desired salt by a method known per se. On the contrary, when the compound obtained in each step is a salt, it can be converted into a free form or another desired kind of salt by a method known per se.

The compound obtained in each step as a reaction solution or as a crude product can be used in the next reaction. Alternatively, the compound obtained in each step can be isolated and/or purified from the reaction mixture by a separation means such as concentration, crystallization, recrystallization, distillation, solvent extraction, fractional distillation or chromatography according to a conventional method.

When the raw material or reagent compound for each step is commercially available, the commercially available product can be used as it is.

In the reaction of each step, the reaction time may vary depending on the reagent or solvent used, but unless otherwise specified, it is usually 1 minute to 48 hours, preferably 10 minutes to 24 hours.

In the reaction of each step, the reaction temperature may vary depending on the reagent or solvent used, but unless otherwise specified, it is usually −78° C. to 300° C., preferably −78° C. to 150° C.

In the reaction of each step, the pressure may vary depending on the reagent or solvent used, but unless otherwise specified, it is usually 1 atm to 20 atm, preferably 1 atm to 3 atm.

In the reaction of each step, for example, a microwave synthesizer such as Initiator manufactured by Biotage may be used. The reaction temperature may vary depending on the reagent or solvent used, but unless otherwise specified, it is usually room temperature to 300° C., preferably 50° C. to 250° C. The reaction time may vary depending on the reagent or solvent used, but unless otherwise specified, it is usually 1 minute to 48 hours, preferably 1 minute to 8 hours.

In the reaction of each step, the reagent is used in an amount of 0.5 equivalents to 20 equivalents, preferably 0.8 equivalents to 5 equivalents, relative to the substrate, unless otherwise specified. When the reagent is used as a catalyst, the reagent is used in an amount of 0.001 equivalents to 1 equivalent, preferably 0.01 equivalents to 0.2 equivalents, relative to the substrate. When the reagent also serves as a reaction solvent, the amount of the reagent used is the amount of solvent.

Unless otherwise specified in the reaction of each step, the reactions are carried out without solvent or through dissolution or suspension in a suitable solvent. Specific examples of the solvent include solvents described in the Examples, or the followings.

Alcohols: methanol, ethanol, tert-butyl alcohol, 2-methoxyethanol, etc.;
Ethers: diethyl ether, diphenyl ether, tetrahydrofuran, 1,2-dimethoxyethane, etc.;
Aromatic hydrocarbons: chlorobenzene, toluene, xylene, etc.;
Saturated hydrocarbons: cyclohexane, hexane, etc.;
Amides: N,N-dimethylformamide, N-methylpyrrolidone, etc.;
Halogenated hydrocarbons: dichloromethane, carbon tetrachloride, etc.;
Nitriles: acetonitrile, etc.;
Sulfoxides: dimethyl sulfoxide, etc.;
Aromatic organic bases: pyridine etc.;
Acid anhydrides: acetic anhydride, etc.;
Organic acids: formic acid, acetic acid, trifluoroacetic acid, etc.;
Inorganic acids: hydrochloric acid, sulfuric acid, etc.;
Esters: ethyl acetate, etc.;
Ketones: acetone, methyl ethyl ketone, etc.;
Water.

As the solvent, two or more kinds may be mixed for use in an appropriate ratio.

When a base is used in the reaction of each step, for example, the base shown below or the base described in the Examples is used.

Inorganic bases: sodium hydroxide, magnesium hydroxide, sodium carbonate, calcium carbonate, sodium hydrogen carbonate, etc.;
Organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, etc.;
Metal alkoxides: sodium ethoxide, potassium tert-butoxide, etc.;
Alkali metal hydrides: sodium hydride, etc.;
Metal amides: sodium amide, lithium diisopropylamide, lithium hexamethyldisilazide, etc.;
Organolithiums: n-butyllithium, etc.

When an acid or an acidic catalyst is used in the reaction of each step, for example, the acid or acidic catalyst shown below, or the acid or acidic catalyst described in the Examples is used.

Inorganic acids: hydrochloric acid, sulfuric acid, nitric acid, hydrobromic acid, phosphoric acid, etc.;
Organic acids: acetic acid, trifluoroacetic acid, citric acid, p-toluenesulfonic acid, 10-camphorsulfonic acid, etc.;
Lewis acids: boron trifluoride diethyl ether complex, zinc iodide, anhydrous aluminum chloride, anhydrous zinc chloride, anhydrous iron chloride, etc.

Unless otherwise specified, the reaction of each step is carried out according to the method known per se, described in, for example, The fifth series of experimental chemistry, Volumes 13 to 19 (Edited by Chemical Society of Japan); New experimental chemistry, Volumes 14 to 15 (Edited by Chemical Society of Japan); Precise Organic Chemistry, Revised 2nd Edition (L. F. Tietze, Th. Eicher, Nankodo Co., Ltd.); Revised Organic Name Reactions; The Reaction Mechanism and Essence (written by Hideo Togo, Kodansha, Ltd.); ORGANIC SYNTHESES Collective Volume I to VII (John Wiley & Sons Inc); Modem Organic Synthesis in the Laboratory A Collection of Standard Experimental Procedures (written by Jie Jack Li, published by OXFORD UNIVERSITY); Comprehensive Heterocyclic Chemistry III, Vol. 1 to Vol. 14 (Elsevier Japan); Strategic applications of named reactions in organic synthesis (the translation supervised by Kiyoshi Tomioka, published by Kagaku-Dojin Publishing Company, Inc.); Comprehensive Organic Transformations (VCH Publishers Inc.) published in 1989, etc., or the method described in the Examples.

In each step, the protecting or deprotecting reaction of the functional group is carried out according to the method known per se, described in, for example, "Protective Groups in Organic Synthesis, 4th Ed." (written by Theodora W. Greene, Peter G. M. Wuts), published by Wiley-Interscience in 2007; "Protecting Groups 3rd Ed." (written by P. J. Kocienski), published by Thieme in 2004, etc., or the method described in the Examples.

Examples of the protecting group for the hydroxyl group of alcohol and phenolic hydroxyl group and the like include ether-type protecting groups such as methoxymethyl ether, benzyl ether, tert-butyldimethylsilyl ether, tetrahydropyranyl ether; carboxylate ester-type protecting groups such as acetate ester; sulfonate ester-type protecting groups such as methanesulfonate ester; and carbonate ester-type protecting groups such as tert-butylcarbonate.

Examples of the protecting group for the carbonyl group of aldehyde include acetal-type protecting groups such as dimethyl acetal; and cyclic acetal-type protecting groups such as 1,3-dioxane.

Examples of the protecting group for the carbonyl group of ketone include ketal-type protecting groups such as dimethyl ketal; cyclic ketal-type protecting groups such as 1,3-dioxane; oxime-type protecting groups such as O-methyloxime; and hydrazone-type protecting groups such as N,N-dimethyl hydrazone.

Examples of the protecting group for a carboxyl group include ester-type protecting groups such as methyl ester; and amide-type protecting groups such as N,N-dimethylamide.

Examples of the protecting group for thiol include ether-type protecting groups such as benzylthioether; and ester-type protecting groups such as thioacetic acid ester, thiocarbonate and thiocarbamate.

Examples of the protecting group for an amino group and an aromatic heterocycle such as imidazole, pyrrole or indole include carbamate-type protecting groups such as benzyl carbamate; amide-type protecting groups such as acetamide; alkylamine-type protecting groups such as N-triphenylmethylamine, and sulfonamide-type protecting groups such as methanesulfonamide.

Removal of the protecting group can be carried out by using a method known per se, for example, methods using acid, base, ultraviolet light, hydrazine, phenylhydrazine, sodium N-methyldithiocarbamate, tetrabutylammonium fluoride, palladium acetate or trialkylsilyl halides (e.g., trimethylsilyl iodide, trimethylsilyl bromide), or a reduction method.

In each step, when carrying out a reduction reaction, the reducing agent used includes metal hydrides such as lithium aluminum hydride, sodium triacetoxyborohydride, sodium cyanoborohydride, diisobutylaluminum hydride (DIBAL-H), sodium borohydride and tetramethylammonium triacetoxyborohydride; boranes such as borane tetrahydrofuran complex; Raney nickel; Raney cobalt; hydrogen; formic acid; and triethylsilane. When reducing a carbon-carbon double bond or triple bond, a method is used in which a catalyst such as a palladium-carbon or Lindlar catalyst is used.

In each step, when carrying out an oxidation reaction, the oxidizing agent used includes peracids such as m-chloroperbenzoic acid (mCPBA), hydrogen peroxide and tert-butyl hydroperoxide; perchlorates such as tetrabutylammonium perchlorate; chlorates such as sodium chlorate; chlorites such as sodium chlorite; periodic acids such as sodium periodate; high-valence iodine reagents such as iodosylbenzene; reagents having manganese such as manganese dioxide and potassium permanganate; leads such as lead tetraacetate; reagents having chromium such as pyridinium chlorochromate (PCC), pyridinium dichromate (PDC) and a Jones reagent; halogen compounds such as N-Bromosuccinimide (NBS); oxygen; ozone; sulfur trioxide-pyridine complex; osmium tetroxide; selenium dioxide; and 2,3-dichloro-5,6-dicyano-1,4-benzoquinone (DDQ).

In each step, when carrying out a radical cyclization reaction, the radical initiator used includes azo compounds such as azobisisobutyronitrile (AIBN); water-soluble radical initiators such as 4-4'-azobis-4-cyanopentanoic acid (ACPA); triethylboron in the presence of air or oxygen; and benzoyl peroxide. In addition, the radical reaction reagent used includes tributylstannane, tristrimethylsilylsilane, 1,1,2,2-tetraphenyldisilane, diphenylsilane and samarium iodide.

In each step, when carrying out the Wittig reaction, the Wittig reagent used includes alkylidene phosphoranes. The alkylidene phosphoranes can be prepared by a method known per se, for example, by reacting a phosphonium salt with a strong base.

In each step, when carrying out the Horner-Emmons reaction, the reagents used include phosphonoacetate esters such as methyl dimethylphosphonoacetate and ethyl diethylphosphonoacetate; and bases such as alkali metal hydrides and organolithiums.

In each step, when carrying out the Friedel-Crafts reaction, the reagents used include a combination of a Lewis acid and an acid chloride, or a combination of a Lewis acid and an alkylating agent (e.g., alkyl halides, alcohols, olefins, etc.). Alternatively, an organic acid or an inorganic acid can be used instead of a Lewis acid, and an acid anhydride such as acetic anhydride can be used instead of an acid chloride.

In each step, when carrying out an aromatic nucleophilic substitution reaction, a nucleophilic reagent (e.g., amines, imidazole, etc.) and a base (e.g., organic bases, etc.) are used as the reagents.

In each step, when carrying out a nucleophilic addition reaction with a carbanion, a nucleophilic 1,4-addition reaction (Michael addition reaction) with a carbanion, or a nucleophilic substitution reaction with a carbanion, the base used to generate the carbanion includes organolithiums, metal alkoxides, inorganic bases and organic bases.

In each step, when carrying out the Grignard reaction, the Grignard reagent includes arylmagnesium halides such as phenylmagnesium bromide; and alkylmagnesium halides such as methylmagnesium bromide. The Grignard reagent can be prepared by a method known per se, for example, by reacting an alkyl halide or an aryl halide with metallic magnesium using ether or tetrahydrofuran as a solvent.

In each step, when carrying out the Knoevenagel condensation reaction, an active methylene compound located between two electron-attracting groups (e.g., malonic acid, diethyl malonate, malononitrile, etc.) and bases (e.g., organic bases, metal alkoxides, inorganic bases) are used as the reagents.

In each step, when carrying out the Vilsmeier-Haack reaction, phosphoryl chloride and an amide derivative (e.g., N,N-dimethylformamide, etc.) are used as the reagents.

In each step, when carrying out an azide reaction of alcohols, alkyl halides and sulfonate esters, the azidizing agent used include diphenylphosphoryl azide (DPPA), trimethylsilyl azide and sodium azide. For example, when azidizing alcohols, a method using diphenylphosphoryl azide (DPPA) and 1,8-diazabicyclo[5.4.0]undec-7-ene (DBU), a method using trimethylsilyl azide and a Lewis acid, and the like are used.

In each step, when carrying out a reductive amination reaction, the reducing agent used includes sodium triacetoxyborohydride, sodium cyanoborohydride, hydrogen and formic acid. When the substrate is an amine compound, the carbonyl compound used include aldehydes such as paraformaldehyde and acetaldehyde, and ketones such as cyclohexanone. When the substrate is a carbonyl compound, the amines used include ammonia; primary amines such as methylamine; and secondary amines such as dimethylamine.

In each step, when carrying out the Mitsunobu reaction, azodicarboxylate esters (e.g., diethyl azodicarboxylate (DEAD), diisopropyl azodicarboxylate (DIAD)) and triphenylphosphine are used as the reagents.

In each step, when carrying out an esterification reaction, an amidation reaction or a urea-formation reaction, the reagent used includes acyl halides such as acid chloride and acid bromide; and activated carboxylic acids such as acid anhydrides, active esters and sulfate esters. An activator for carboxylic acid includes carbodiimide-based condensing agents such as 1-ethyl-3-(3-dimethylaminopropyl)carbodiimide hydrochloride (WSCD); triazine-based condensing agents such as 4-(4,6-dimethoxy-1,3,5-triazin-2-yl)-4-methylmorpholinium chloride-n-hydrate (DMT-MM); carbonate ester-based condensing agents such as 1,1-carbonyldiimidazole (CDI); diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl halo formate such as ethyl chloroformate; O-(7-azabenzotriazol-1-yl)-N,N,N',N'-tetramethyluronium hexafluorophosphate (HATU); sulfuric acid; or a combination thereof. When the carbodiimide-based condensing agent is used, an additive such as 1-hydroxybenzotriazole (HOBt), N-hydroxysuccinimide (HOSu) or 4-dimethylaminopyridine (DMAP) may be further added to the reaction.

In each step, when carrying out a coupling reaction, the metal catalyst used include palladium compounds such as palladium acetate(II), tetrakis(triphenylphosphine)palladium(0), dichlorobis(triphenylphosphine)palladium(II), dichlorobis(triethylphosphine)palladium(II), tris(dibenzylideneacetone)dipalladium(0), and 1,1'-bis(diphenylphosphino)ferrocene palladium(II) chloride; nickel compounds such as tetrakis(triphenylphosphine)nickel(0); rhodium compounds such as tris(triphenylphosphine)rhodium(III) chloride; cobalt compounds; copper compounds such as copper oxide and copper(I) iodide; and platinum compounds. Furthermore, a base may be added to the reaction, and such a base includes inorganic bases.

In each step, when carrying out a thiocarbonylation reaction, diphosphorus pentasulfide is typically used as the thiocarbonylating agent. In addition to the diphosphorus pentasulfide, reagents having a 1,3,2,4-dithiadiphosphetane-2,4-disulfide structure such as 2,4-bis(4-methoxyphenyl)-1,3,2,4-dithiadiphosphetane-2,4-disulfide (Lawesson's reagent) may be used.

In each step, when carrying out the Wohl-Ziegler reaction, the halogenating agent used include N-iodosuccinimide, N-bromosuccinimide (NBS), N-chlorosuccinimide (NCS), bromine and sulfuryl chloride. Furthermore, the reaction can be accelerated by adding a radical initiator such as heat, light, benzoyl peroxide or azobisisobutyronitrile to the reaction.

In each step, when carrying out a halogenation reaction of the hydroxy group, the halogenating agent used includes acid halides of hydrohalic acids and inorganic acids, specifically hydrochloric acid, thionyl chloride and phosphorus oxychloride for chlorination, and 48% hydrobromic acid for bromination. In addition, a method may be used for preparing an alkyl halide from an alcohol by the action of triphenylphosphine with carbon tetrachloride, carbon tetrabromide or the like. Alternatively, a method may be used for synthesizing an alkyl halide through a two-step reaction including converting an alcohol to a sulfonate ester, followed by reaction with lithium bromide, lithium chloride or sodium iodide.

In each step, when carrying out the Arbuzov reaction, the reagent used includes alkyl halides such as ethyl bromoacetate; and phosphites such as triethyl phosphite and tri(isopropyl)phosphite.

In each step, when carrying out a sulfonate esterification reaction, the sulfonylating agent used includes methanesulfonyl chloride, p-toluenesulfonyl chloride, methanesulfonic acid anhydride and p-toluenesulfonic acid anhydride.

In each step, when carrying out a hydrolysis reaction, an acid or a base is used as the reagent. In addition, when carrying out an acid hydrolysis reaction of tert-butyl ester, formic acid, triethylsilane or the like may be added in order to reductively trap the by-product tert-butyl cation.

In each step, when carrying out a dehydration reaction, the dehydrating agent used includes sulfuric acid, diphosphorus pentoxide, phosphorus oxychloride, N,N'-dicyclohexylcarbodiimide, alumina and polyphosphoric acid.

When the compound obtained in each step has amino groups, imidazoles, pyrroles, aromatic heterocycles such as indole, carboxyl groups, hydroxyl group and the like as substituents, these groups may be protected with a protecting group such as those listed above. In this case, the target compound can be obtained by removing the protecting group at a desired stage. The introduction or removal of these protecting groups is carried out in the same manner as described above.

Furthermore, in each step, the above-mentioned reaction and the like may be optionally incorporated.

Hereinafter, a description is made of the method for producing the compound (I).

Unless otherwise specified, each symbol in the following reaction formula has the same meaning as described above. The raw material compound can be easily obtained on the market, or can be produced by a method known per se or a similar method, unless a specific producing method is described.

The compound (I) can be produced from the compound (II) by the following method.

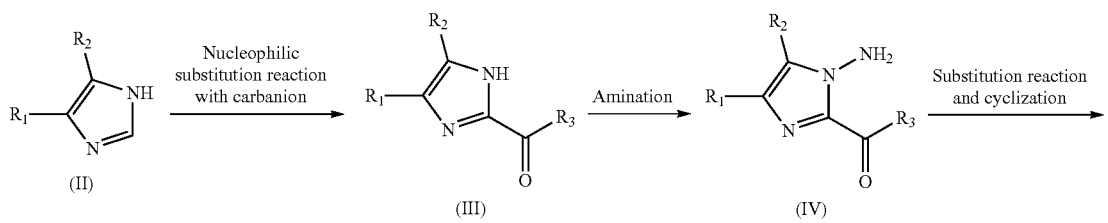

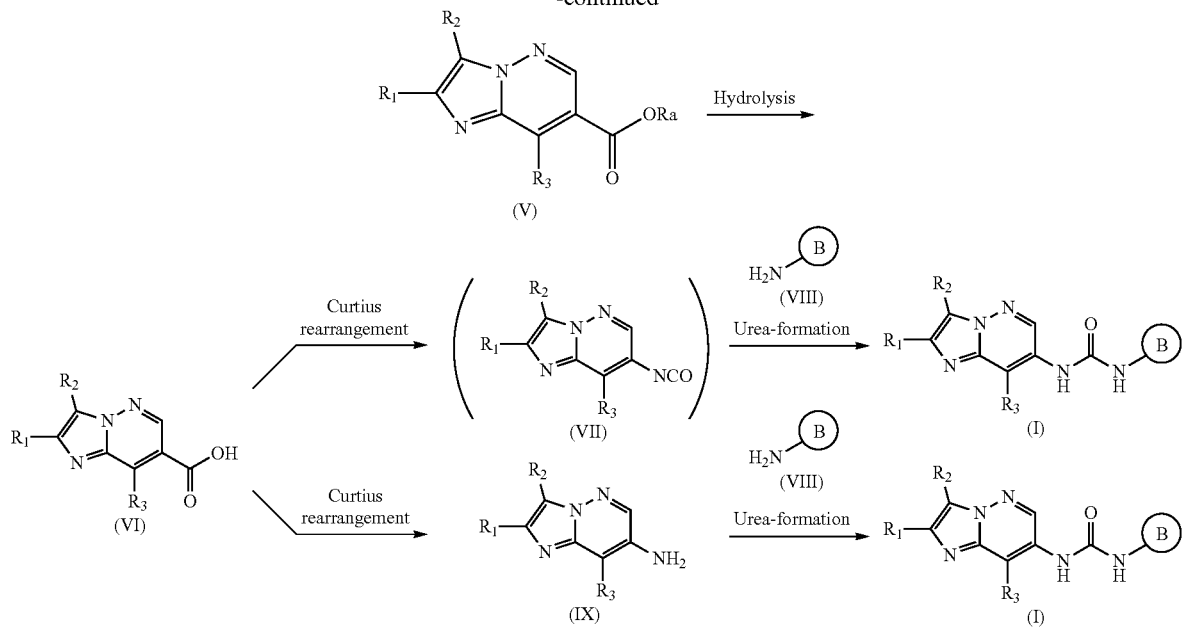

The compound (II) can be a commercially available product or be produced by using a method known per se.

The compound (IV) can be produced by an amination reaction of the compound (III) with a hydroxylamine derivative in the presence of a base or an acid. The hydroxylamine derivative includes O-(4-nitrobenzoyl)hydroxylamine, hydroxylamine-O-sulfonic acid and O-diphenylphosphinyl hydroxylamine.

The compound (V) can be produced by reacting the compound (IV) with an acrylate ester under an oxygen atmosphere in the presence of a palladium catalyst and an inorganic salt such as lithium bromide. The palladium catalyst includes palladium(II) acetate, and the acrylate ester includes methyl acrylate and ethyl acrylate. Alternatively, the compound (V) can also be produced by reacting the compound (IV) with methyl 3,3-dimethoxypropanoate in the presence of an acid, followed by intramolecular cyclization in the presence of a base.

The compound (VIII) can be a commercially available product as it is, or be produced by using a method known per se or a similar method.

The compound (I) can be produced by reacting the compound (VIII) with the compound (VII) obtained by reacting the compound (VI) under a coexistence of diphenylphosphoryl azide (DPPA), optionally a base, using the Curtius rearrangement. The solvent used includes 2-methyltetrahydrofuran, in addition to the above.

The compound (IX) can be produced by reacting the compound (VI) under a coexistence of diphenylphosphoryl azide (DPPA), optionally a base, using the Curtius rearrangement. The solvent used includes 2-methyltetrahydrofuran, in addition to the above.

The compound (I) can be produced by a urea-formation under a coexistence of the compound (IX), compound (VIII), an activator, and optionally a base. The activator includes chloroformate ester derivatives such as 2,2,2-trichloroethyl chloroformate, phenyl chloroformate or p-nitrophenyl chloroformate, triphosgene, phosgene, N,N'-carbonyldiimidazole, or N,N'-disuccinimidyl carbonate. Among them, triphosgene and 2,2,2-trichloroethyl chloroformate are preferable.

In the above step, the substituents $R_1$ and $R_2$ can be converted to other types of substituents by an electrophilic substitution reaction, a coupling reaction or a method known per se at a desired stage. For example, the compound (IV) in which $R_1$ is a halogen atom can be produced by carrying out an electrophilic substitution reaction on the compound (IV) in which $R_1$ is a hydrogen atom. The electrophile used in this reaction include N-iodosuccinimide, N-bromosuccinimide (NBS), N-chlorosuccinimide (NCS), bromine and sulfuryl chloride. In addition, the compound (V) in which $R_1$ is a $C_{1-3}$ alkyl group (e.g., a methyl group) can be produced by allowing the compound (V) in which $R_1$ is a leaving group (e.g., a halogen atom) to act with an organic boronic acid or an organic boronate ester reagent (e.g., 2,4,6-trimethylboroxin). This reaction can be carried out in the presence of a base or inorganic salt (e.g., tripotassium phosphate), the above-mentioned metal complex such as palladium, or in the presence of a phosphine ligand. Examples of the phosphine ligand include 2-dicyclohexylphosphino-2',6'-dimethoxybiphenyl (SPhos).

The compound (V) can also be produced by the following method.

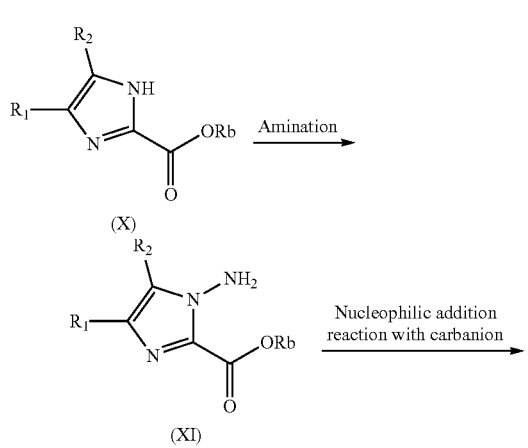

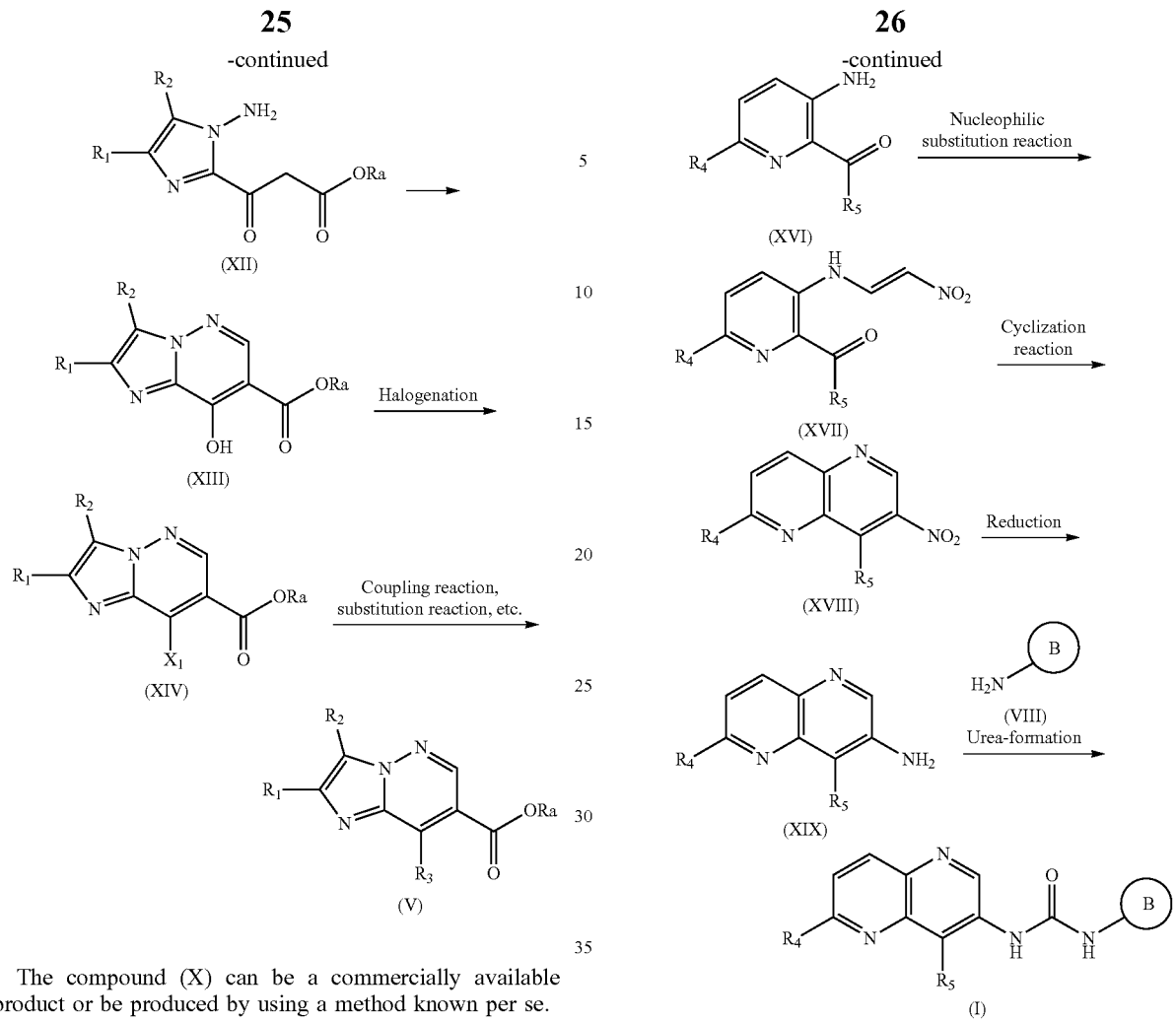

The compound (X) can be a commercially available product or be produced by using a method known per se.

The compound (XI) can be produced by an amination reaction of the compound (X). The amination method includes the same method as the method for producing the compound (IV) from the compound (III).

The compound (XIII) can be produced by reacting the compound (XII) in the presence of N,N-dimethylformamide dimethyl acetal.

$X_1$ of the compound (XIV) represents a halogen atom. The halogenating agent used in the halogenation reaction in the production of the compound (XIV) includes phosphorus oxybromide in addition to the above.

The compound (V) can be produced from the compound (XIV) by incorporating a coupling reaction, a substitution reaction or a method known per se.

In the above step, the substituents $R_1$ and $R_2$ can be converted to other types of substituents by an electrophilic substitution reaction or a method known per se at a desired stage.

The compound (I) can also be produced by the following method.

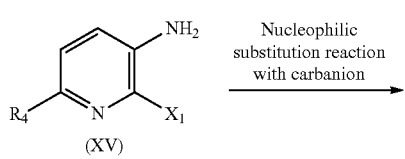

The compound (XV) can be a commercially available product or be produced by using a method known per se. $X_1$ represents a halogen atom.

The compound (XVII) can be produced by subjecting the compound (XVI) and a nitroenamine derivative to a nucleophilic substitution reaction in the presence of an acid. The nitroenamine derivative includes (E)-4-(2-nitrovinyl)morpholine.

The compound (XVIII) can be produced by an intramolecular cyclization reaction of the compound (XVII). This reaction can be optionally carried out in the presence of a base.

The compound (XIX) can be produced by reducing the compound (XVIII). In addition to the above, the reducing agent includes iron, tin(II) chloride and tin(II) chloride dihydrate.

The compound (I) can be produced by a urea-formation under a coexistence of the compound (XIX), compound (VIII), an activator, and optionally a base. The activator includes chloroformate ester derivatives such as 2,2,2-trichloroethyl chloroformate, phenyl chloroformate or p-nitrophenyl chloroformate, triphosgene, phosgene, N,N'-carbonyldiimidazole, or N,N'-disuccinimidyl carbonate. Among them, triphosgene and 2,2,2-trichloroethyl chloroformate are preferable.

In the above steps, the substituents $R_4$ and $R_5$ can be converted by incorporating a coupling reaction, a substitution reaction, or a method known per se at a desired stage.

The compound (I) can also be produced by the following method.

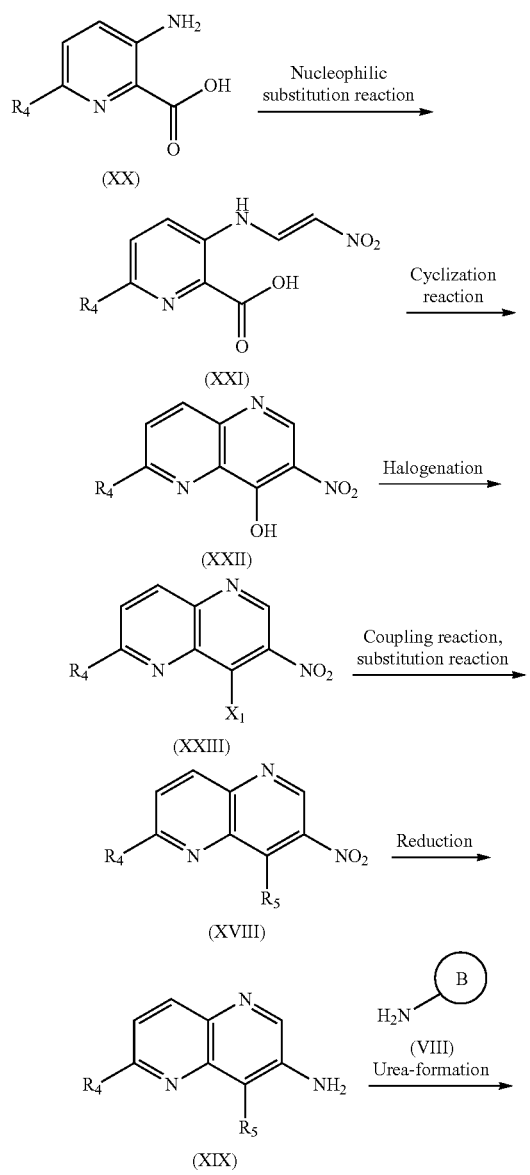

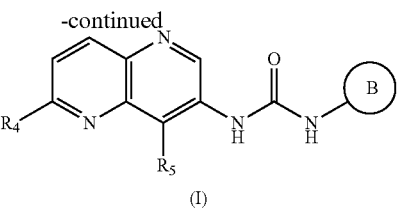

The compound (XX) can be a commercially available product or be produced by using a method known per se.

The compound (XXI) can be produced by subjecting the compound (XX) and a nitroenamine derivative to a nucleophilic substitution reaction in the presence of an acid. The nitroenamine derivative includes (E)-4-(2-nitrovinyl)morpholine.

The compound (XXII) can be produced by an intramolecular cyclization reaction of the compound (XXI). This reaction can be optionally carried out in the presence of a base.

$X_1$ of the compound (XXIII) represents a halogen atom. The halogenating agent used in the halogenation reaction in the production of the compound (XXIII) includes phosphorus tribromide in addition to the above.

The compound (XVIII) can be produced from the compound (XXIII) by incorporating a coupling reaction, a substitution reaction or a several step method known per se. The catalyst used in the coupling reaction in the production of the compound (XVIII) includes $PdCl_2$ $(Amphos)_2$ in addition to the above.

The compound (XIX) can be produced by reducing the compound (XVIII). In addition to the above, the reducing agent includes iron, tin(II) chloride and tin(II) chloride dihydrate.

The compound (I) can be produced by a urea-formation under a coexistence of the compound (XIX), compound (VIII), an activator, and optionally a base. The activator includes chloroformate ester derivatives such as 2,2,2-trichloroethyl chloroformate, phenyl chloroformate or p-nitrophenyl chloroformate, triphosgene, phosgene, N,N'-carbonyldiimidazole, or N,N'-disuccinimidyl carbonate. Among them, triphosgene and 2,2,2-trichloroethyl chloroformate are preferable.

In the above steps, the substituents $R_4$ and $R_5$ can be converted by incorporating a coupling reaction, a nucleophilic substitution reaction, or a method known per se at a desired stage.

The compound (I) can also be produced by the following method.

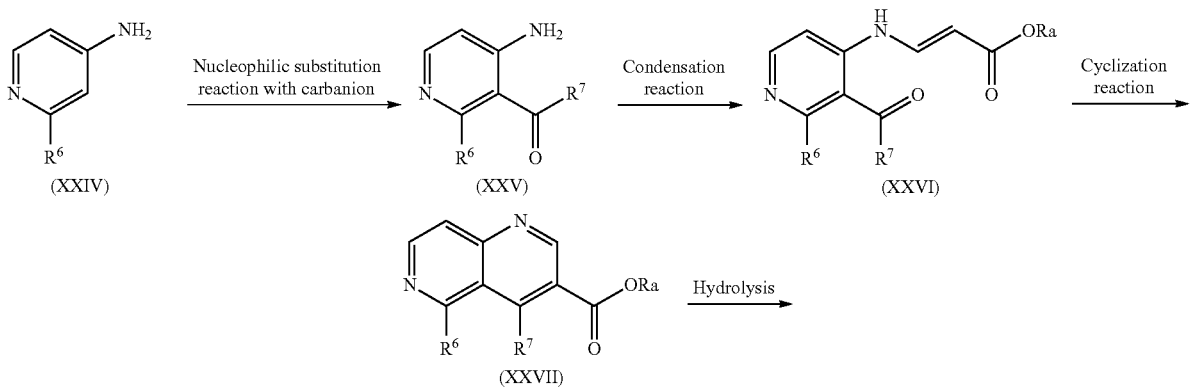

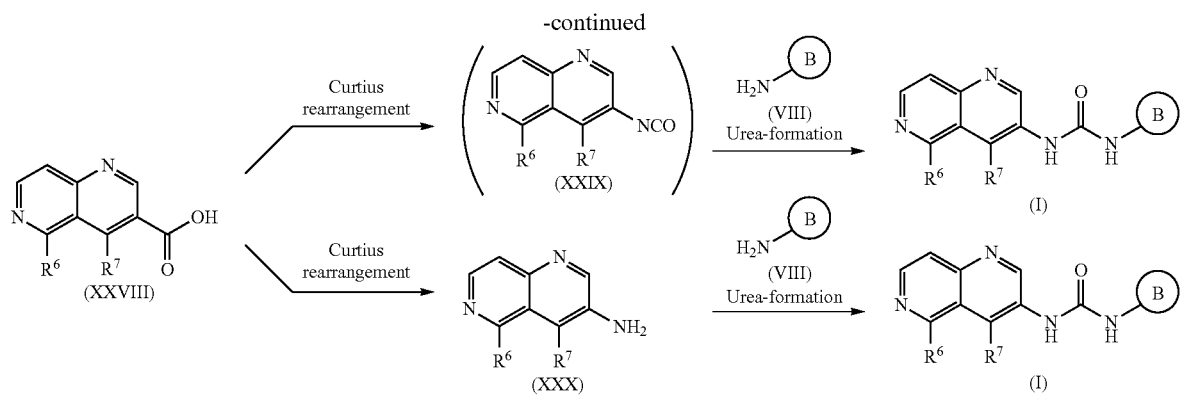

The compound (XXIV) can be a commercially available product or be produced by using a method known per se.

The compound (XXVI) can be produced by subjecting the compound (XXV) and a 3-oxopropanoic acid derivative to a nucleophilic substitution reaction in the presence of an acid. The 3-oxopropanoic acid derivative includes methyl 3,3-dimethoxypropanoate.

The compound (XXVII) can be produced by an intramolecular cyclization reaction of the compound (XXVI). This reaction can be optionally carried out in the presence of a base.

The compound (I) can be produced by reacting the compound (VIII) with the compound (XXIX) obtained by reacting the compound (XXVIII) under a coexistence of diphenylphosphoryl azide (DPPA), optionally a base, using the Curtius rearrangement. The solvent used includes 2-methyltetrahydrofuran, in addition to the above.

The compound (XXX) can be produced by reacting the compound (XXVIII) under a coexistence of diphenylphosphoryl azide (DPPA), optionally a base, using the Curtius rearrangement. The solvent used includes 2-methyltetrahydrofuran, in addition to the above.

The compound (I) can be produced by a urea-formation under a coexistence of the compound (XXX), compound (VIII), an activator, and optionally a base. The activator includes chloroformate ester derivatives such as 2,2,2-trichloroethyl chloroformate, phenyl chloroformate or p-nitrophenyl chloroformate, triphosgene, phosgene, N,N'-carbonyldiimidazole, or N,N'-disuccinimidyl carbonate. Among them, triphosgene and 2,2,2-trichloroethyl chloroformate are preferable.

In the above steps, the substituents $R_6$ and $R_7$ can be converted by incorporating a coupling reaction, a substitution reaction, or a method known per se at a desired stage.

The compound (I) can also be produced by the following method.

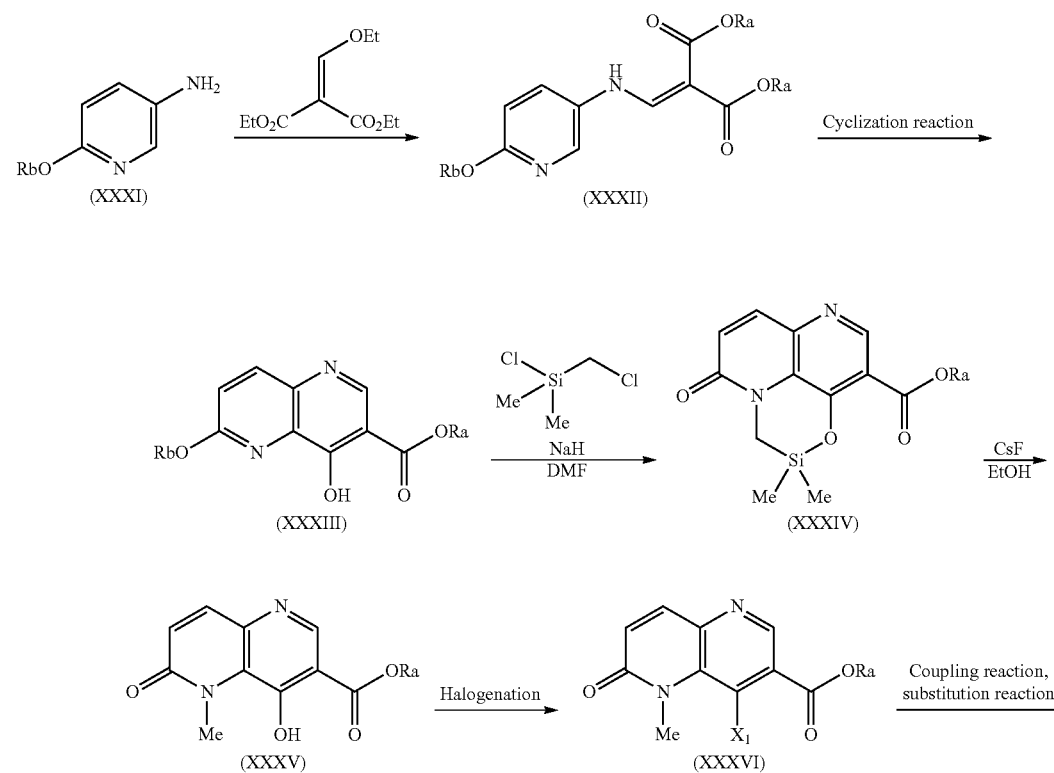

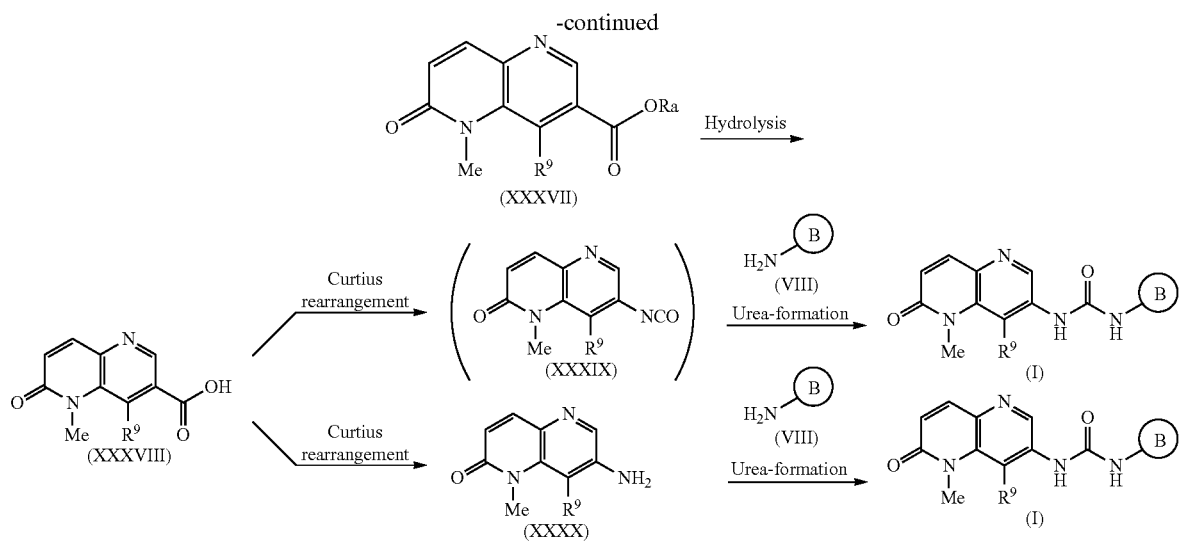

The compound (XXXI) can be a commercially available product or be produced by using a method known per se.

The compound (XXXII) can be produced by subjecting the compound (XXXI) and an alkoxymethylene malonic acid derivative to a nucleophilic substitution reaction in the presence of an acid. The alkoxymethylene malonic acid derivative includes diethyl ethoxymethylene malonate.

The compound (XXXIII) can be produced by an intramolecular cyclization reaction of the compound (XXXII).

The compound (XXXIV) can be produced by reacting the compound (XXXIII) with chloro(chloromethyl)dimethylsilane in the presence of a base.

The compound (XXXV) can be produced by reacting the compound (XXXIV) with cesium fluoride.

$X_1$ of the compound (XXXVI) represents a halogen atom. The halogenating agent used in the halogenation reaction in the production of the compound (XXXVI) includes phosphorus tribromide in addition to the above.

The compound (I) can be produced by reacting the compound (VIII) with the compound (XXXIX) obtained by reacting the compound (XXXVIII) under a coexistence of diphenylphosphoryl azide (DPPA), optionally a base, using the Curtius rearrangement. The solvent used includes 2-methyltetrahydrofuran, in addition to the above.

The compound (XXXX) can be produced by reacting the compound (XXXVIII) under a coexistence of diphenylphosphoryl azide (DPPA), optionally a base, using the Curtius rearrangement. The solvent used includes 2-methyltetrahydrofuran, in addition to the above.

The compound (I) can be produced by a urea-formation under a coexistence of the compound (XXXX), compound (VIII), an activator, and optionally a base. The activator includes chloroformate ester derivatives such as 2,2,2-trichloroethyl chloroformate, phenyl chloroformate or p-nitrophenyl chloroformate, triphosgene, phosgene, N,N'-carbonyldiimidazole, or N,N'-disuccinimidyl carbonate. Among them, triphosgene and 2,2,2-trichloroethyl chloroformate are preferable.

In the above steps, the substituent $R_9$ can be converted by incorporating a coupling reaction, a substitution reaction, or a method known per se at a desired stage.

The compound (I) can also be produced by the following method.

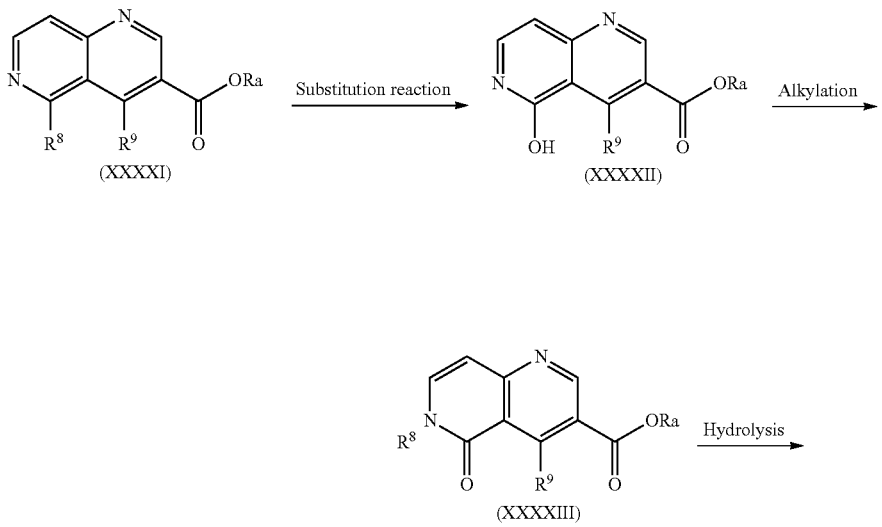

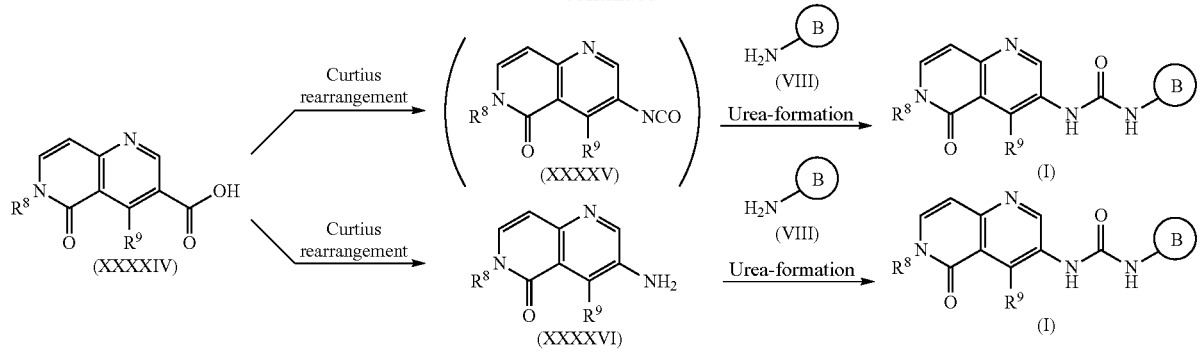

The compound (XXXXI) can be a commercially available product, or produced by using a method known per se or the same method as that for the compound (XXVII).

The compound (XXXXIII) can be produced by alkylating the compound (XXXXII) in the presence of a base. The base includes lithium hydroxide in addition to the above.

The compound (I) can be produced by reacting the compound (VIII) with the compound (XXXXV) obtained by reacting the compound (XXXXIV) under a coexistence of diphenylphosphoryl azide (DPPA), optionally a base, using the Curtius rearrangement. The solvent used includes 2-methyltetrahydrofuran, in addition to the above.

The compound (XXXXVI) can be produced by reacting the compound (XXXXIV) under a coexistence of diphenylphosphoryl azide (DPPA), optionally a base, using the Curtius rearrangement. The solvent used includes 2-methyltetrahydrofuran, in addition to the above.

The compound (I) can be produced by a urea-formation under a coexistence of the compound (XXXXVI), compound (VIII), an activator, and optionally a base. The activator includes chloroformate ester derivatives such as 2,2,2-trichloroethyl chloroformate, phenyl chloroformate or p-nitrophenyl chloroformate, triphosgene, phosgene, N,N'-carbonyldiimidazole, or N,N'-disuccinimidyl carbonate. Among them, triphosgene and 2,2,2-trichloroethyl chloroformate are preferable.

In the above steps, the substituents $R_8$ and $R_9$ can be converted by incorporating a coupling reaction, a substitution reaction, or a method known per se at a desired stage.

Conversion of the substituent of the obtained compound (I) by applying a means known per se (that is, introduction of a substituent or conversion of a functional group) can also produce another compound or a salt thereof included in the compound (I).

As the method for introduction of a substituent or conversion of a functional group, known general methods are used. Examples of them include conversion of a halogen atom (e.g., fluorine, chlorine, bromine, iodine) or a $C_{1-6}$ alkylsulfonyl-oxy group which may be halogenated [e.g., methanesulfonyloxy, ethanesulfonyloxy, trichloromethanesulfonyloxy, trifluoromethanesulfonyloxy (triflate)] to a methyl group, a cyclopropyl group, a vinyl group, a cyano group, a formyl group, a carbonyl group, a carboxyl group, a hydroxyl group, an amino group or a boryl group, conversion of a formyl group to an ethynyl group by the Seyferth-Gilbert homologation, conversion of an ester to a carboxy group by hydrolysis, conversion of a carboxy group to a carbamoyl group by amidation, conversion of a carboxy group to a hydroxymethyl group by reduction, conversion of a carbonyl group to alcohol by reduction or alkylation, reductive amination of a carbonyl group, oxime-formation of a carbonyl group, acylation of an amino group, urea-formation of an amino group, sulfonylation of an amino group, alkylation of an amino group, substitution or amination of an active halogen with an amine, alkylation of a hydroxy group, and substitution or amination of a hydroxy group.

In the case where there is a reactive site by which a reaction other than the intended one occurs when the introduction of a substituent or conversion of a functional group is carried out, the compound included in the scope of the present invention can also be produced by introducing a protecting group into the reactive site in advance by a means known per se, and removing the protecting group by a means known per se after completion of the desired reaction, as needed.

For example, when the raw material compound or intermediate has an amino group, a carboxyl group or a hydroxyl group as a substituent, these groups may be protected with a protecting group commonly used in peptide chemistry and the like. In this case, the target compound can be obtained by removing the protecting group after the reaction, as needed.

The compound (I) obtained by the above-mentioned producing method can be isolated and purified by a known means such as solvent extraction, pH change of solution, transfer dissolution, crystallization, recrystallization and chromatography.

When the compound (I) contains optical isomers, steric isomers, positional isomers and rotational isomers, these isomers are also included as the compound (1), and can be each obtained as a single product by a synthesis technique and a separating technique known per se. For example, when the compound (I) has an optical isomer, the optical isomer separated from the compound is also included in the compound (I).

Here, the optical isomer can be produced by a method known per se.

The compound (I) may be crystalline.

The crystal of the compound (I) (hereinafter, sometimes abbreviated as "crystal of the present invention") can be produced by applying a crystallization method known per se to the compound (I) to crystallize the same.

The crystal of the present invention is expected to have excellent physicochemical properties (e.g., melting point, solubility, stability) and biological properties (e.g., in vivo kinetics (absorption, distribution, metabolism, excretion), efficacy of medicine) and be useful as a medicine.

The compound (I) may be a pharmaceutically acceptable co-crystal or co-crystal salt. Here, the co-crystal or cocrystal salt means a crystalline substance composed of two or more unique solids at room temperature, which solids are different in physical property (e.g., structure, melting point, heat of fusion, hygroscopicity, solubility and stability) from each other. The co-crystal or co-crystal salt can be produced according to a co-crystallization method known per se.

The compound (I) may be a hydrate, a non-hydrate, a non-solvate or a solvate.

Furthermore, a deuterium-converted compound in which $^1$H has been converted to $^2$H (D) is also included in the compound (I).

The compound (I) may be labeled with an isotope (e.g., $^3$H, $^{13}$C, $^{14}$C, $^{18}$F, $^{35}$S, $^{125}$I) or the like. The isotope-labeled or substituted compound (I) can be used, for example, as a tracer (PET (positron emission tomography) tracer) used in PET, and is expected as useful in fields such as medical diagnosis.

The compound (I) may be used as a prodrug.

The prodrug of the compound (I) is a compound that is converted to the compound (I) by a reaction with an enzyme, gastric acid or the like under physiological conditions in the living body, that is, a compound that enzymatically undergoes oxidation, reduction, hydrolysis etc. to change to the compound (I), or a compound that undergoes hydrolysis or the like due to gastric acid or the like to change to the compound (I).

The prodrug of the compound (I) includes a compound having the amino group of the compound (I) acylated, alkylated or phosphorylated (e.g., a compound having the amino group of the compound (I) eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated); a compound having the hydroxy group of the compound (I) acylated, alkylated, phosphorylated or borated (e.g., a compound having the hydroxy group of the compound (I) acetylated, palmitoylated, propanoylated, pivaloylated, succinylated, fumarylated, alanylated, or dimethylaminomethylcarbonylated); a compound having the carboxy group of the compound (I) esterified or amidated (e.g., a compound having the carboxy group of the compound (I) ethyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, or methylamidated). These compounds can be produced from the compound (I) by a method known per se.

In addition, the prodrug of the compound (I) may be one changing to the compound (I) under physiological conditions, as described in Molecular Design, pp. 163 to 198 in "Pharmaceutical research and development", Vol. 7, by Hirokawa Shoten in 1990.

In the description, the prodrug may form a salt. Such a salt includes those exemplified as the salt of the compound represented by the above formula (I).

The compound (I) or a prodrug thereof (hereinafter, sometimes simply abbreviated as "compound of the present invention") can have MALT1 inhibitory activity, and may be useful as a prophylactic or therapeutic drug for cancer, an inhibitor for cancer growth, and an inhibitor for metastasis of cancer.

The compound of the present invention can be useful as a medicine, because the compound of the present invention exhibits selective inhibitory activity against MALT1, and is also excellent in efficacy of medicine, pharmacokinetics (e.g., absorbability, distribution, metabolism, excretion), solubility (e.g., water solubility), interaction with other pharmaceutical products (e.g., an effect of inhibiting a drug-metabolizing enzyme), safety (e.g., acute toxicity, chronic toxicity, genetic toxicity, reproductive toxicity, cardiotoxicity, carcinogenicity, central toxicity), and stability (e.g., chemical stability, stability against enzyme).

Accordingly, the compound of the present invention can be used to inhibit an excessive (abnormal) MALT1 effect in mammals (e.g., mouse, rat, hamster, rabbit, cat, dog, cattle, sheep, monkey, human).

The compound of the present invention can be orally or parenterally administered to a mammal (preferably human) as a medicine, either as it is or in combination with a pharmacologically acceptable carrier.

Hereinafter, a detailed description is made of a medicine containing the compound of the present invention (sometimes abbreviated as "medicine of the present invention"). Examples of the dosage form of the medicine of the present invention include oral preparations such as tablets (e.g., a sugar-coated tablet, a film-coated tablet, a sublingual tablet, a buccal tablet, an orally fast-disintegrating tablet), pills, granules, powders, capsules (e.g., a soft capsule, a microcapsule), syrups, emulsions, suspensions and film preparations (e.g., an orally disintegrating film, an oral mucosa sticking film). In addition, examples of the dosage forms of the medicine of the present invention include parenteral preparations such as injections, infusions, transdermal agents (e.g., an iontophoresis transdermal agent), suppositories, ointments, nasal agents, transpulmonary agents and eye drops. Furthermore, the medicine of the present invention may be release-controlled preparations such as quick-release preparations and sustained-release preparations (e.g., a sustained-release microcapsule).

The medicine of the present invention can be produced by a known producing method generally used in the pharmaceutical field (e.g., the method described in the Japanese Pharmacopoeia). In addition, the medicine of the present invention can contain an additive such as an excipient, a binder, a disintegrant, a lubricant, a sweetener, a surfactant, a suspending agent, an emulsifier, a colorant, a preservative, an aromatic substance, a flavoring agent, a stabilizer or a thickener commonly used in the pharmaceutical field, in an appropriate amount, if needed.

The pharmacologically acceptable carrier described above includes these additives.

For example, the tablets can be produced using an excipient, a binder, a disintegrant, a lubricant and the like, and the pills and granules can be produced using an excipient, a binder, a disintegrant and the like. In addition, the powders and capsules can be produced using an excipient and the like, the syrups can be produced using a sweetener and the like, and the emulsions or suspensions can be produced using a suspending agent, a surfactant, am emulsifier and the like.

Examples of the excipient include lactose, sucrose, glucose, starch, sucrose, microcrystalline cellulose, powdered glycyrrhiza, mannitol, sodium hydrogen carbonate, calcium phosphate and calcium sulfate.

Examples of the binder include 5 to 10% by weight starch paste, 10 to 20% by weight gum arabic solution or gelatin solution, 1 to 5% by weight tragacanth solution, carboxymethyl cellulose solution, sodium alginate solution or glycerin.

Examples of the disintegrant include starch and calcium carbonate.

Examples of the lubricant include magnesium stearate, stearic acid, calcium stearate and purified talc.

Examples of the sweetener include glucose, fructose, inverted sugar, sorbitol, xylitol, glycerin and simple syrup.

Examples of the surfactant include sodium lauryl sulfate, Polysorbate 80, sorbitan monofatty acid ester and Polyoxyl 40 stearate.

Examples of the suspending agent include gum arabic, sodium alginate, sodium carboxymethyl cellulose, methyl cellulose and bentonite.

Examples of the emulsifier include gum arabic, tragacanth, gelatin and Polysorbate 80.

For example, in the case where the medicine of the present invention is a tablet, the tablet can be produced by adding to the compound of the present invention, for example, an excipient (e.g., lactose, sucrose, starch), a disintegrant (e.g., starch, calcium carbonate), a binder (e.g., starch, gum arabic, carboxymethyl cellulose, polyvinylpyrrolidone, hydroxypropyl cellulose), or a lubricant (e.g., talc, magnesium stearate, Polyethylene glycol 6000), followed by compression-molding, according to a method known per se, and then optionally performing taste masking, enteric or persistent coating in a manner known per se. As the coating agent used for coating include hydroxypropylmethyl cellulose, for example, ethyl cellulose, hydroxymethyl cellulose, hydroxypropyl cellulose, polyoxyethylene glycol, Tween 80, Pluronic F68, cellulose acetate phthalate, hydroxypropyl methyl cellulose phthalate, hydroxymethyl cellulose acetate succinate, Eudragit (manufactured by ROHM, Germany, methacrylic acid/acrylic acid copolymer) and dyes (e.g., red iron oxide, titanium dioxide) can be used.

The injections include an intravenous injection, a subcutaneous injection, an intradermal injection, an intramuscular injection, an intraperitoneal injection and a drip injection.

Such injections are prepared by a method known per se, that is, by dissolving, suspending or emulsifying the compound of the invention in a sterile aqueous or oily liquid. The aqueous liquid includes saline, and isotonic solutions containing glucose or other adjuvants (e.g., D-sorbitol, D-mannitol, sodium chloride). The aqueous liquid may contain a suitable solubilizer such as alcohol (e.g., ethanol), polyalcohol (e.g., propylene glycol, polyethylene glycol), or a nonionic surfactant (e.g., Polysorbate 80, HCO-50). The oily liquid includes a sesame oil and a soybean oil. The oily liquid may contain a suitable solubilizer. The solubilizer includes benzyl benzoate and benzyl alcohol. In addition, into the injection, a buffer (e.g., a phosphate buffer, a sodium acetate buffer), a soothing agent (e.g., benzalkonium chloride, procaine hydrochloride), a stabilizer (e.g., human serum albumin, polyethylene glycol), a preservative (e.g., benzyl alcohol, phenol) or the like may be blended. The prepared injection solution may be usually filled in an ampoule.

The content of the compound of the present invention in the medicine of the present invention varies depending on the form of the preparation, but is usually about 0.01 to about 100% by weight, preferably about 2 to about 85% by weight, more preferably about 5 to about 70% by weight, relative to the whole preparation.

The content of the additive in the medicine of the present invention varies depending on the form of the preparation, but is usually about 1 to about 99.9% by weight, preferably about 10 to about 90% by weight, relative to the whole preparation.

The compound of the present invention is stable, has low toxicity, and can be used safely. The daily dose of the compound of the present invention varies depending on the patient's condition and weight, the type of compound, the route of administration, etc. For example, when orally administered to a patient for the purpose of treating cancer, the daily dose for an adult (body weight about 60 kg) is about 1 to about 1000 mg, preferably about 3 to about 300 mg, more preferably about 10 to about 200 mg of the compound of the present invention. The daily dose may be administered in a single dose or in 2 to 3 divided doses.

When the compound of the present invention is administered parenterally, it is usually administered in the form of a liquid preparation (e.g., injection). The single dose of the compound of the present invention varies depending on the administration target, target organ, symptom, administration method, etc. For example, usually, it is preferable to administer about 0.01 to about 100 mg, preferably about 0.01 to about 50 mg, more preferably about 0.01 to about 20 mg of the compound of the present invention per kg of body weight by intravenous injection.

The compound of the present invention can be used in combination with other drugs. Specifically, the compound of the present invention can be used in combination with drugs such as a hormonal therapeutic agent, a chemotherapeutic agent, an immunotherapeutic agent or a drug that inhibits the effect of a cell growth factor and its receptor. Hereinafter, a drug that can be used in combination with the compound of the present invention is abbreviated as "concomitant drug".

As the "hormonal therapeutic agent", for example, fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, antiestrogens (e.g., tamoxifen citrate, toremifene citrate), pills, mepitiostane, testololactone, aminoglutethimide, LH-RH agonists (e.g., goserelin acetate, buserelin, leuprorelin acetate), droloxifene, epitiostanol, ethinyl estradiol sulfonate, aromatase inhibitors (e.g., fadrozole hydrochloride, anastrozole, letrozole, exemestane, vorozole, formestane), anti-androgens (e.g., flutamide, bicalutamide, nilutamide, enzalutamide), 5α-reductase inhibitors (e.g., finasteride, epristeride, dutasteride), adrenocortical hormonal drugs (e.g., dexamethasone, prednisolone, betamethasone, triamcinolone), androgen synthesis inhibitors (e.g., abiraterone), retinoid and drugs that slows the metabolism of retinoid (e.g., liarozole), thyroid hormone, and their Drug Delivery System (DDS) preparations can be used.

As the "chemotherapeutic agent", for example, alkylating agents, antimetabolites, anticancer antibiotics, and plant-derived anticancer agents can be used.

As the "alkylating agents", for example, nitrogen mustard, nitrogen mustard N-oxide hydrochloride, chlorambucil, cyclophosphamide, ifosfamide, thiotepa, carbocon, improsulfan tosylate, busulfan, nimustine hydrochloride, mitobronitol, melphalan, dacarbazine, ranimustine, estramustine sodium phosphate, triethylene melamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulfan, trophosphamide, zinostatin stimalamer, adozelesin, cystemustine, bizelesin, and their DDS preparations can be used.

As the "antimetabolites", for example, mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, galocitabine, emitefur, capecitabine), aminopterin, nelarabine, leucovorin calcium, tabloid, butocin, calcium folinate, levofolinate calcium, cladribine, emitefur, fludarabine, gemcitabine, hydroxycarbamide, pentostatin, piritrexim, idoxuridine, mitoguazone, tiazofurin, ambamustine, bendamustine, and their DDS preparations can be used.

As the "anticancer antibiotics", for example, actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride, and their DDS preparations (e.g., a doxorubicin-encapsulating PEG ribosome) can be used.

As the "plant-derived anticancer agents", for example, etoposide, etoposide phosphate, vinblastine sulfate, vincristine sulfate, vindesine sulfate, teniposide, paclitaxel, docetaxel, cabazitaxel, vinorelbine and their DDS preparations can be used.

As the "immunotherapeutic agent", for, example, picibanil, krestin, schizophyllan, lentinan, ubenimex, interferon, interleukin, macrophage colony stimulating factors, granulocyte colony stimulating factors, erythropoietin, lymphotoxin, BCG vaccine, *Corynebacterium parvum*, levamisole, polysaccharide K, procodazole, anti-CTLA4 antibodies (e.g., ipilimumab, tremelimumab), anti-PD-1 antibodies (e.g., nivolumab, pembrolizumab) and anti-PD-L1 antibodies can be used.

The "cell growth factor" in the "drug that inhibits the effect of a cell growth factor and its receptor" may be any substance that promotes cell growth, and usually includes factors that are peptides having a molecular weight of 20,000 or less, and exert their effects at a low concentration by binding to a receptor. Specifically, (1) EGF (epidermal growth factor) or substances having substantially the same activity [e.g., TGFα], (2) insulin or substances having substantially the same activity [e.g., insulin, IGF (insulin-like growth factor)-1, IGF-2], (3) FGF (fibroblast growth factor) or substances having substantially the same activity [e.g., acidic FGF, basic FGF, KGF (keratinocyte growth factor), FGF-10], and (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascularendothelial growth factor), heregulin and angiopoietin] can be used.

The "receptor for a cell growth factor" may be any receptor having the ability to bind to the above-mentioned cell growth factor. Specifically, EGF receptor, heregulin receptor (e.g., HER3), insulin receptor, IGF receptor-1, IGF receptor-2, FGF receptor-1 or FGF receptor-2, VEGF receptor, angiopoietin receptor (e.g., Tie2), PDGF receptor, and the like can be used.

As the "drug that inhibits the effect of a cell growth factor and its receptor", EGF inhibitors, TGFα inhibitors, heregulin inhibitors, insulin inhibitors, IGF inhibitors, FGF inhibitors, KGF inhibitors, CSF inhibitors, EPO inhibitors, IL-2 inhibitors, NGF inhibitors, PDGF inhibitors, TGFβ inhibitors, HGF inhibitors, VEGF inhibitors, angiopoietin inhibitors, EGF receptor inhibitors, HER2 inhibitors, HER4 inhibitors, insulin receptor inhibitors, IGF-1 receptor inhibitors, IGF-2 receptor inhibitors, FGF receptor-1 inhibitors, FGF receptor-2 inhibitors, FGF receptor-3 inhibitors, FGF receptor-4 inhibitors, VEGF receptor inhibitors, Tie-2 inhibitors, PDGF receptor inhibitors, TLR receptor inhibitors, Abl inhibitors, Raf inhibitors, FLT3 inhibitors, c-Kit inhibitors, Src inhibitors, PLC inhibitors, PKC inhibitors, Smo inhibitors, ALK inhibitors, RORI inhibitors, Trk inhibitors, Ret inhibitors, mTOR inhibitors, Aurora inhibitors, PLK inhibitors, MEK (MEK1/2) inhibitors, MET inhibitors, CDK inhibitors, Akt inhibitors, ERK inhibitors, P13K inhibitors, IKK inhibitors, BTK inhibitors, IRAK inhibitors, HDAC inhibitors, TAKI inhibitors, TBK1 inhibitors, ZAP inhibitors, SYK inhibitors, LCK inhibitors, TYK2 inhibitors, SYK inhibitors, JAK inhibitors, FAK inhibitors, LYN inhibitors and the like can be used. More specifically, anti-VEGF antibodies (e.g., bevacizumab, ramucurumab), anti-HER2 antibodies (e.g., trastuzumab, pertuzumab), anti-EGFR antibodies (e.g., cetuximab, panitumumab, matuzumab, nimotuzumab), anti-HGF antibodies, imatinib, erlotinib, gefitinib, sorafenib, sunitinib, dasatinib, lapatinib, vatalanib, ibrutinib, bosutinib, cabozantinib, crizotinib, alectinib, vismodegib, axitinib, motesanib, nilotinib, 6-[4-(4-ethylpiperazin-1-ylmethyl)phenyl]-N-[1(R)-phenylethyl]-7H-pyrrolo[2,3-d]pyrimidine-4-amine (AEE-788), vandetanib, temsirolimus, everolimus, enzastaurin, tozasertib, 2-[N-[3-[4-[5-[N-(3-fluorophenyl)carbamoylmethyl]-1H-pyrazole-3-ylamino]quinazolin-7-yloxy]propyl]-N-ethylamino]ethyl phosphate ester (AZD-1152), 4-[9-chloro-7-(2,6-difluorophenyl)-5H-pyrimid[5,4-d][2]benzazepin-2-ylamino]benzoic acid, N-[2-methoxy-5-[(E)-2-(2,4,6-trimethoxyphenyl)vinylsulfonylmethyl]phenyl]glycine sodium salt (ON-1910Na), volasertib, selumetinib, trametinib, N-[2(R),3-dihydroxypropoxy]-3,4-difluoro-2-(2-fluoro-4-iodophenylamino)benzamide (PD-0325901), bosutinib, regorafenib, afatinib, idelalisib, ceritinib, dabrafenib and the like can be used.

In addition to the above drugs, asparaginase, aceglatone, procarbazine hydrochloride, protoporphyrin-cobalt complex salt, mercury hematoporphyrin-sodium, topoisomerase I inhibitors (e.g., irinotecan, topotecan, indotecan, indimitecan), topoisomerase II inhibitors (e.g., sobuzoxane), differentiation inducers (e.g., retinoids, vitamin Ds), other angiogenesis inhibitors (e.g., fumagillin, shark extract, COX-2 inhibitors), α-blockers (e.g., tamsulosin hydrochloride), bisphosphonic acid (e.g., pamidronate, zoledronate), thalidomide, lenalidomide, pomalidomide, 5 azacitidine, decitabine, proteasome inhibitors (e.g., bortezomib, carfilzomib, ixazomib), NEDD8 inhibitors (e.g., pevonedistat), UAE inhibitors, PARP inhibitors (e.g., olaparib, niraparib, veliparib), BCL2 inhibitors (e.g., venetoclax, obatoclax, oblimersen), anti-neoplastic antibodies such as an anti-CD20 antibody (e.g., rituximab, obinutuzumab) and an anti-CCR4 antibody (e.g., mogamulizumab), antibody-drug conjugates (e.g., trastuzumab emtansine, brentuximab vedotin), gene-modified T cell therapies using chimeric antigen receptors (CARs) (CAR-T therapies) (e.g., tisagenlecleucel, axicabtagene ciloleucel) and the like can also be used as concomitant medicines.

Combination of the compound of the present invention with a concomitant drug can provide excellent effects. For example, (1) the dose can be reduced as compared with the case where the compound of the present invention or the concomitant drug is administered alone, (2) a drug to be used in combination with the compound of the present invention can be selected depending on the patient's symptom (mild, severe, etc.), (3) the duration of treatment can be set longer, (4) the therapeutic effect can be sustained, and (5) a synergistic effect can be achieved by using the compound of the present invention in combination with the concomitant drug.

Hereinafter, the case where the compound of the present invention is used in combination with a concomitant drug is referred to as "concomitant drug of the present invention".

When using the concomitant drug of the present invention, the timing of administration of the compound of the present invention and a concomitant drug is not limited, but the compound of the present invention and a concomitant drug may be administered to the subject to be administered at the same time, or with a time lag. When administered with a time lag, the time lag will vary depending on the administered active ingredient, dosage form, and administration method. For example, when a concomitant drug is administered first, the compound of the present invention may be administered within 1 minute to 3 days, preferably within 10 minutes to 1 day, more preferably within 15 minutes to 1 hour after the concomitant drug is administered. When the compound of the present invention is administered first, a concomitant drug may be administered within 1 minute to 1 day, preferably within 10 minutes to 6 hours, more preferably within 15 minutes to 1 hour after the compound of the present invention is administered. The dose of a concomitant drug may be based on the clinically used dose, and may be appropriately selected depending on the subject to be administered, administration route, disease, combination and the like.

Examples of the administration form when the compound of the present invention and a concomitant drug are used in combination include (1) administration of a single preparation obtained by simultaneously formulating the compound of the present invention and the concomitant drug, (2) simultaneous administration of two preparations obtained by separately formulating the compound of the present invention and the concomitant drug through the same route of administration, (3) administration of two preparations obtained by separately formulating the compound of the present invention and the concomitant drug through the same route of administration with a time lag, (4) simultaneous administration of two preparations obtained by separately formulating the compound of the present invention and the concomitant drug through different routes of administration, and (5) administration of two preparations obtained by separately formulating the compound of the present invention and the concomitant drug through different routes of administration with a time lag (for example, administration in the order of the compound of the present invention and concomitant drug, or administration in the reverse order).

The dose of a concomitant drug can be appropriately selected based on the clinically used dose. In addition, the blending ratio of the compound of the present invention and a concomitant drug can be appropriately selected depending on the subject to be administered, administration route, target disease, symptom, combination and the like. For example, when the subject to be administered is a human, 0.01 to 100 parts by weight of a concomitant drug may be used with respect to 1 part by weight of the compound of the present invention.

Furthermore, the compound of the present invention or the concomitant drug of the present invention can be used in combination with non-drug therapies. Specifically, the compound of the present invention or the concomitant drug of the present invention can be combined with a non-drug therapy, for example, (1) surgery, (2) induced hypertension chemotherapy using angiotensin II or the like, (3) gene therapy, (4) thermotherapy, (5) cryotherapy, (6) laser ablation, and (7) radiation therapy.

For example, by using the compound of the present invention or the concomitant drug of the present invention before or after the surgery or the like, or before or after treatment of a combination of these two or three, effects such as inhibition of development of resistance, prolongation of disease-free survival, suppression of cancer metastasis or recurrence, and prolongation of life can be achieved.

In addition, treatment with the compound of the present invention or the concomitant drug of the present invention, and supportive therapy [(i) administration of an antibiotic (e.g., β-lactams such as pansporin, macrolides such as clarithromycin) against the complications of various infectious diseases, (ii) administration of a high-calorie infusion, an amino acid preparation, and a multivitamin for improving nutrition disorders, (iii) administration of morphine for pain relief, (iv) administration of a drug that improves side effects such as nausea, vomiting, loss of appetite, diarrhea, leukopenia, thrombocytopenia, decreased hemoglobin concentration, hair loss, liver damage, kidney damage, DIC and fever, and (v) administration of a drug for suppressing multidrug resistance of cancer, etc.] can be combined.

EXAMPLES

A detailed description is further made of the present invention with reference to the following Examples, Preparation Examples and Test Examples, but the present invention is not limited thereto. The present invention may be modified without departing from the scope of the present invention.

"Room temperature" in the following Examples usually indicates about 10° C. to about 35° C. The ratio represented in a mixed solvent represents the volume ratio unless otherwise specified. Percent (%) indicates the weight % unless otherwise specified.

In silica gel column chromatography, aminopropylsilane-bonded silica gel was used when described as NH, 3-(2,3-dihydroxypropoxy)propylsilane-bonded silica gel was done when described as Diol, and N-(2-aminoethyl)-3-aminopropylsilane-bonded silica gel was done when described as DiNI. When described as C18 in HPLC (high performance liquid chromatography), octadecyl-bonded silica gel was used. The ratio of the elution solvent represents the volume ratio unless otherwise specified.

The Following Abbreviations are Used in the Following Examples

Boc$_2$O: Di-tert-butyl dicarbonate
CDCl$_3$: Deuterated chloroform
DMSO-d$_6$: Deuterated dimethyl sulfoxide
$^1$H NMR: Proton nuclear magnetic resonance
LC/MS: Liquid chromatograph mass spectrometer
ESI: Electrospray ionization
APCI: Atmospheric pressure chemical ionization
DBU: 1,8-Diazabicyclo[5.4.0]undeca-7-en
DIEA: Diisopropylethylamine
DMAP: 4-Dimethylaminopyridine
DMF: N,N-dimethylformamide
mp: Melting point
DPPA: Diphenylphosphoryl azide
MS: Mass spectrum
[M+H]$^+$, [M−H]$^−$: Molecular ion peak
M: Molarity
N: Normality
Pd(OAc)$_2$: Palladium acetate (II)
SPhos: 2-Dicyclohexylphosphino-2',6'-dimethoxybiphenyl
TEA: Triethylamine
TFA: Trifluoroacetic acid
THF: Tetrahydrofuran ¹H NMR was measured by Fourier transform NMR. ACD/SpecManager (trade name) and the like were used for the analysis. A description is not made of a peak of very loose protons, for example, those for hydroxyl groups and amino groups.

MS was measured by LC/MS. As the ionization method, the ESI method or the APCI method was used. The described data are the measured (found) values. Usually, a molecular ion peak ([M+H]$^+$, [M−H]$^−$, etc.) is observed, but in the case of a compound having a tert-butoxycarbonyl group, as a fragment ion, a peak of an eliminated tert-butoxycarbonyl group or tert-butyl group may be observed. In addition, in the case of a compound having a hydroxyl group, as a fragment ion, a peak of detached H$_2$O may be observed. In the case of salts, free molecular ion peaks or fragment ion peaks are usually observed.

Reference Example 1

5-Chloro-6-(difluoromethoxy)pyridine-3-amine

A) 3-Chloro-2-(difluoromethoxy)-5-nitropyridine

To a mixture of 3-chloro-5-nitropyridine-2-ol (10 g) and acetonitrile (300 mL) were added 2,2-difluoro-2-(fluorosulfonyl)acetic acid (11.86 mL) and sodium sulfate (3.26 g) at room temperature, followed by stirring at the same temperature overnight. To the resultant reaction mixture were further added 2,2-difluoro-2-(fluorosulfonyl)acetic acid (11.86 mL) and sodium sulfate (3.26 g) at room temperature, followed by stirring at the same temperature for 3 days. A saturated aqueous sodium hydrogen carbonate solution was added to the reaction mixture to make it basic, followed by concentration under reduced pressure. The aqueous layer was extracted with ethyl acetate, the organic layer was washed with water and saturated saline, and then dried over anhydrous sodium sulfate, and the solvent was distilled off under reduced pressure. The residue was purified by silica gel column chromatography (NH, ethyl acetate/hexane) to yield the title compound (4.31 g).

¹H NMR (300 MHz, DMSO-d$_6$) δ 7.84 (1H, t, J=70.8 Hz), 8.97 (1H, d, J=2.6 Hz), 9.11 (1H, d, J=2.3 Hz).

B) 5-Chloro-6-(difluoromethoxy)pyridine-3-amine

A mixture of 3-chloro-2-(difluoromethoxy)-5-nitropyridine (2.57 g), tin(II) chloride dihydrate (12.91 g) and ethanol (100 mL) was stirred at 70° C. overnight. The resultant reaction mixture was diluted with ethyl acetate and a saturated aqueous sodium hydrogen carbonate solution, and then the insoluble material was filtered off. The aqueous layer of the filtrate was extracted with ethyl acetate, the organic layer was washed with water and saturated saline, and then dried over anhydrous sodium sulfate, and the solvent was distilled off under reduced pressure. The residue was purified by silica gel column chromatography (ethyl acetate/hexane) to yield the title compound (2.17 g).

MS: [M+H]$^+$ 194.9.

Reference Example 2

6-(2H-1,2,3-triazol-2-yl)-5-(trifluoromethyl)pyridine-3-amine

A) 5-Nitro-2-(2H-1,2,3-triazol-2-yl)-3-(trifluoromethyl)pyridine

To a mixture of 2-chloro-5-nitro-3-(trifluoromethyl)pyridine (3.0 g) and THF (15 mL) was added 2H-1,2,3-triazole (0.921 mL) at room temperature. The resultant reaction mixture was stirred at the same temperature for 2 hours. The reaction mixture was diluted with water, and then the aqueous layer was extracted with ethyl acetate. The organic layer was washed with water and saturated saline, and then dried over anhydrous sodium sulfate, and the solvent was distilled off under reduced pressure. The residue was purified by silica gel column chromatography (ethyl acetate/hexane) to yield the title compound (2.75 g).

MS: [M+H]$^+$ 259.9.

B) 6-(2H-1,2,3-triazol-2-yl)-5-(trifluoromethyl)pyridine-3-amine

To a mixture of 5-nitro-2-(2H-1,2,3-triazol-2-yl)-3-(trifluoromethyl)pyridine (3.54 g), a 10% hydrochloric acid/methanol solution (101 mL) and methanol (100 mL) was added tin(II) chloride (12.95 g) at room temperature, and the resultant reaction mixture was stirred at the same temperature for 2 hours. The solvent was distilled off under reduced pressure, ethyl acetate was added to the residue, and a 2 N aqueous sodium hydroxide solution was added to the mixture for neutralization. The precipitate was filtered off, and then the aqueous layer of the filtrate was extracted with ethyl acetate. The organic layer was washed with water and saturated saline, and then dried over anhydrous sodium sulfate, and the solvent was distilled off under reduced pressure. The residue was purified by silica gel column chromatography (ethyl acetate/hexane) to yield the title compound (2.95 g).

MS: [M+H]$^+$ 229.9.

Reference Example 3

5-Chloro-6-(2H-1,2,3-triazol-2-yl)pyridine-3-amine
A) 3-Chloro-5-nitro-2-(2H-1,2,3-triazol-2-yl)pyridine A mixture of 2,3-dichloro-5-nitropyridine (5.0 g), 2H-1,2,3-triazole (1.7 mL), potassium carbonate (4.3 g) and DMF (25 mL) was stirred at room temperature for 3 hours. The resultant reaction mixture was poured into ice water, followed by twice extraction with ethyl acetate. The organic layer was washed twice with water, and with saturated saline, and then dried over sodium sulfate, followed by concentration under reduced pressure. The residue was purified by silica gel column chromatography (ethyl acetate/hexane) to yield the title compound (3.5 g).

MS: [M+H]$^+$ 225.9.

B) 5-Chloro-6-(2H-1,2,3-triazol-2-yl)pyridine-3-amine

A mixture of 3-chloro-5-nitro-2-(2H-1,2,3-triazol-2-yl)pyridine (3.3 g), tin(II) chloride dihydrate (16.3 g) and ethanol (100 mL) was stirred at 70° C. overnight. The reaction mixture was diluted with ethyl acetate, a saturated aqueous sodium hydrogen carbonate solution was added, and then the insoluble material was filtered off. The organic layer was separated, washed with water and saturated saline, dried over sodium sulfate, and then concentrated under reduced pressure. The residue was purified by silica gel column chromatography (ethyl acetate/hexane) to yield the title compound (2.4 g).

MS: [M+H]$^+$ 195.9.

Reference Example 4

5-Amino-2-(difluoromethoxy)nicotinonitrile

A mixture of 5-chloro-6-(difluoromethoxy)pyridine-3-amine (319 mg), Tris(dibenzylideneacetone)dipalladium (0)

(300 mg), Sphos (269 mg), zinc cyanide (1.54 g) and DMF (10 mL) was stirred at 120° C. for 1 hour under irradiation with microwave. The resultant reaction mixture was poured into a 10% aqueous ammonia solution, followed by extraction with ethyl acetate. The organic layer was washed with a 10% aqueous ammonia solution, water, followed by saturated saline, dried over magnesium sulfate, and then concentrated under reduced pressure. The residue was purified by silica gel column chromatography (ethyl acetate/hexane) to yield the title compound (205 mg).

MS: [M+H]$^+$ 185.9.

Example 1

(S)-N-(5-Chloro-6-(difluoromethoxy)pyridin-3-yl)-N'-(8-(1-methoxyethyl)-2-methylimidazo[1,2-b]pyridazin-7-yl)urea

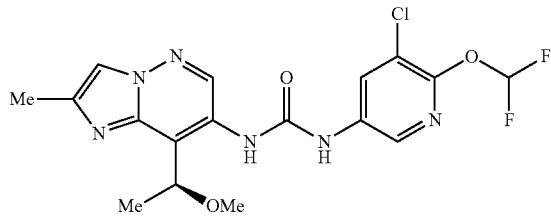

A) 2-Methoxy-1-(1-(triphenylmethyl)-1H-imidazol-2-yl)propan-1-one

To a mixture of 1-(triphenylmethyl)-1H-imidazole (50 g) and THF (600 mL) was added dropwise 1.6 M n-butyl-lithium/hexane solution (100 mL) at −10° C., followed by temperature rising to 0° C. Then, the resultant reaction mixture was stirred at the same temperature for 30 minutes. The reaction mixture was cooled to −78° C., followed by dropwise addition of methyl 2-methoxypropanoate (20.94 g). The resultant reaction mixture was stirred at the same temperature for 1 hour, followed by temperature rising to room temperature for 3 hours. To the reaction mixture was added a saturated aqueous ammonium chloride solution (10 mL), followed by extraction of the aqueous layer with ethyl acetate. The organic layer was washed with water and saturated saline, and then dried over anhydrous sodium sulfate, and the solvent was distilled off under reduced pressure. Hexane was added to the residue, and the precipitate was collected by filtration to yield the title compound (50 g).

$^1$H NMR (400 MHz, DMSO-d$_6$) δ 0.90 (3H, d, J=6.8 Hz), 2.83 (3H, s), 4.88-4.93 (1H, m), 6.89-7.43 (17H, m).

B) 1-(1 H-Imidazol-2-yl)-2-methoxypropan-1-one

A mixture of 2-methoxy-1-(1-(triphenylmethyl)-1H-imidazol-2-yl)propan-1-one (150 g) and a 5% acetic acid/methanol solution (500 mL) was heated to reflux for 16 hours. After cooling the resultant reaction mixture to room temperature, the solvent was distilled off under reduced pressure. The residue was purified by silica gel column chromatography (ethyl acetate/hexane) to yield the title compound (44 g).

MS: [M+H]$^+$ 154.8.

C) 1-(1-Amino-1H-imidazol-2-yl)-2-methoxypropan-1-one

To a mixture of 1-(1H-imidazol-2-yl)-2-methoxypropan-1-one (20 g) and DMF (100 mL) was added a solution of 1 M potassium tert-butoxide in THF (143 mL) at room temperature. Then, the resultant reaction mixture was stirred at the same temperature for 30 minutes. To the reaction mixture was added O-(4-nitrobenzoyl)hydroxylamine (26 g) at room temperature, followed by stirring at the same temperature for 16 hours. Ice-cooled water (40 mL) was added to the reaction mixture, and the solvent was distilled off under reduced pressure. Ethyl acetate (200 mL) was added to the residue, the insoluble material was filtered off, and the filtrate was concentrated under reduced pressure. The residue was purified by silica gel column chromatography (ethyl acetate/hexane) to yield the title compound (17 g).

$^1$H-NMR (400 MHz, DMSO-d$_6$) δ 1.32 (3H, d, J=6.8 Hz), 3.24 (3H, s), 4.94-4.99 (1H, m), 6.86 (2H, brs), 7.06 (1H, s), 7.47 (1H, s).

D) tert-Butyl(2-(2-methoxypropanoyl)-1H-imidazol-1-yl)carbamate

To the mixture of 1-(1-amino-1H-imidazol-2-yl)-2-methoxypropan-1-one (17 g) and DMF (50 mL) was added DMAP (6.1 g) at room temperature, followed by addition of Boc$_2$O (22.3 mL) at the same temperature. The resultant reaction mixture was stirred at 80° C. for 1 hour and then cooled to room temperature. The solvent was distilled off under reduced pressure, and the residue was purified by silica gel column chromatography (ethyl acetate/hexane) to yield the title compound (13 g).

MS: [M+H]$^+$ 270.1.

E) tert-Butyl(4-bromo-2-(2-methoxypropanoyl)-1H-imidazol-1-yl)carbamate

To a mixture of tert-butyl (2-(2-methoxypropanoyl)-1H-imidazol-1-yl)carbamate (8.0 g) and DMF (40 mL) was added dropwise a solution of N-bromosuccinimide (5.2 g) in DMF (10 mL) at room temperature. Then, the resultant reaction mixture was stirred at the same temperature for 16 hours. The reaction mixture was diluted with water (80 mL), followed by extraction of the aqueous layer with ethyl acetate. The organic layer was washed with water and saturated saline, and then dried over anhydrous sodium sulfate, and the solvent was distilled off under reduced pressure. The residue was purified by silica gel column chromatography (ethyl acetate/hexane) to yield the title compound (5.5 g).

$^1$H-NMR (400 MHz, DMSO-d$_6$) δ 1.28 (3H, d, J=6.8 Hz), 1.46 (9H, s), 3.21 (3H, s), 4.83-4.85 (1H, m), 7.93 (1H, s), 10.80 (1H, s).

F) 1-(1-Amino-4-bromo-1H-imidazol-2-yl)-2-methoxypropan-1-one

To a mixture of tert-butyl(4-bromo-2-(2-methoxypropanoyl)-1H-imidazol-1-yl)carbamate (10 g) and dichloromethane (100 mL) was added TFA (20 mL) at 0° C. Then, the resultant reaction mixture was stirred at room temperature for 1 hour. The reaction mixture was concentrated under reduced pressure, and a saturated aqueous sodium hydrogen carbonate solution (50 mL) was added to the residue. The aqueous layer was extracted with ethyl acetate, the organic layer was washed with water and saturated saline, and then

G) Methyl 2-bromo-8-(1-methoxyethyl)imidazo[1,2-b]pyridazine-7-carboxylate

To a mixture of 1-(1-amino-4-bromo-IH-imidazol-2-yl)-2-methoxypropan-1-one (7.0 g) and THF (50 mL) were added methyl acrylate (5.1 mL) and Lithium bromide (9.71 g) at room temperature. The resultant reaction mixture was degassed with oxygen, and then Pd(OAc)$_2$ (1.27 g) was added to the reaction mixture at the same temperature, followed by stirring at 50° C. for 16 hours under an oxygen atmosphere. The reaction mixture was diluted with ice-cooled water (50 mL), followed by extraction of the aqueous layer with ethyl acetate. The organic layer was washed with water and saturated saline, and then dried over anhydrous sodium sulfate, and the solvent was distilled off under reduced pressure. The residue was purified by silica gel column chromatography (ethyl acetate/hexane) to yield the title compound (5.0 g).

MS: [M+H]$^+$ 314.0.

H) Methyl 8-(1-methoxyethyl)-2-methylimidazo[1,2-b]pyridazine-7-carboxylate

After a mixture of methyl 2-bromo-8-(1-methoxyethyl)imidazo[1,2-b]pyridazine-7-carboxylate (8.0 g), toluene (70 mL) and water (10 mL) was degassed with nitrogen, tripotassium phosphate (17.6 g) and 2,4,6-trimethylboroxin (7.12 mL) were added at room temperature. After further degassing the mixture with nitrogen, Pd(OAc)$_2$ (571 mg) and SPhos (1.57 g) were added at room temperature, followed by stirring at 80° C. for 3 hours. The resultant reaction mixture was diluted with a saturated aqueous sodium hydrogen carbonate solution (50 mL), followed by extraction of the aqueous layer with ethyl acetate. The organic layer was washed with water and saturated saline, and then dried over anhydrous sodium sulfate, and the solvent was distilled off under reduced pressure. The residue was purified by silica gel column chromatography (ethyl acetate/hexane) to yield the title compound (4.0 g).

MS: [M+H]$^+$ 250.2

I) (S)-Methyl 8-(1-methoxyethyl)-2-methylimidazo[1,2-b]pyridazine-7-carboxylate Methyl 8-(1-methoxyethyl)-2-methylimidazo[1,2-b]pyridazine-7-carboxylate (4.36 g) was fractioned by HPLC (CHIRALCEL OD-H (VJ002), 20 mm ID×250 mm L, mobile phase: hexane/2-propanol=950/50). The fraction with a shorter retention time containing the target product was concentrated under reduced pressure to yield the title compound (2034 mg).

Optical purity: 99.9% ee, retention time: 6.845 minutes (CHIRALCEL OD-H (VK069), 4.6 mm ID×250 mm L, mobile phase: hexane/2-propanol=950/50)

MS: [M+H]$^+$ 250.0.

The absolute configuration was determined using a single crystal X-ray diffractometer.

J) (S)-8-(1-Methoxyethyl)-2-methylimidazo[1,2-b]pyridazine-7-carboxylic acid trifluoroacetate To a mixture of (S)-methyl 8-(1-methoxyethyl)-2-methylimidazo[1,2-b]pyridazine-7-carboxylate (1.71 g) and acetic acid (17 mL) was added a 6 N hydrochloric acid solution (17.15 mL) at room temperature, followed by stirring at 100° C. overnight. The resultant reaction mixture was concentrated under reduced pressure, the residue was fractioned by HPLC (C18, mobile phase: water/acetonitrile (containing 0.1% TFA)). The obtained fraction was concentrated under reduced pressure, and then dried under reduced pressure to yield the title compound (2.6 g).

MS: [M+H]$^+$ 236.0.

K) (S)-8-(1-Methoxyethyl)-2-methylimidazo[1,2-b]pyridazine-7-amine

To a mixture of (S)-8-(1-methoxyethyl)-2-methylimidazo[1,2-b]pyridazine-7-carboxylic acid trifluoroacetate (2.6 g), TEA (5.3 mL) and toluene (150 mL) was added DPPA (4.9 mL) at room temperature, followed by stirring at the same temperature for 2 hours. Acetic acid (50 mL) and water (50 mL) were added to the resultant reaction mixture, followed by stirring at 80° C. overnight. After the reaction mixture was concentrated under reduced pressure, the residue was diluted with a saturated aqueous sodium hydrogen carbonate solution, followed by extraction of the aqueous layer with ethyl acetate. The organic layer was washed with saturated saline, and then dried over anhydrous magnesium sulfate, and the solvent was distilled off under reduced pressure. The residue was purified by silica gel column chromatography (NH, ethyl acetate/hexane) to yield the title compound (1.38 g).

MS: [M+H]$^+$ 207.0.

L) (S)-N-(5-Chloro-6-(difluoromethoxy)pyridin-3-yl)-N'-(8-(1-methoxyethyl)-2-methylimidazo[1,2-b]pyridazin-7-yl)urea To a mixture of (S)-8-(1-methoxyethyl)-2-methylimidazo[1,2-b]pyridazine-7-amine (1180 mg), DIEA (3.49 mL) and THF (10 mL) was added triphosgene (679.1 mg) at 0° C., followed by stirring at room temperature for 1 hr. To the resultant reaction mixture was added 5-chloro-6-(difluoromethoxy)pyridine-3-amine (1.17 g) obtained in Reference Example 1 at room temperature, followed by stirring at 60° C. for 2 hours. A saturated aqueous sodium hydrogen carbonate solution was added to the reaction mixture, the aqueous layer was extracted with ethyl acetate, the organic layer was washed with saturated saline, and then dried over anhydrous magnesium sulfate, and the solvent was distilled off under reduced pressure. The residue was purified by silica gel column chromatography (NH, ethyl acetate/hexane), followed by silica gel column chromatography (methanol/ethyl acetate) to yield the title compound (1.83 g).

$^1$H NMR (300 MHz, DMSO-d$_6$) δ 1.52 (3H, d, J=6.8 Hz), 2.35 (3H, d, J=0.8 Hz), 3.30 (3H, s), 5.26 (1H, q, J=6.8 Hz), 7.40-7.91 (11H, m), 7.92 (1H, d, J=0.8 Hz), 8.21 (1H, d, J=2.3 Hz), 8.33 (1H, d, J=2.3 Hz), 8.69 (1H, br s), 9.01 (1H, s), 10.27 (1H, br s).

MS: [M+H]$^+$ 427.0.

The absolute configuration was determined using a single crystal X-ray diffractometer.

--- dried over anhydrous sodium sulfate, and the solvent was distilled off under reduced pressure. n-Pentane was added to the residue, and the precipitate was collected by filtration to yield the title compound (7.0 g).

MS: [M+H]$^+$ 248.2.

Example 2

(S)-N-(6-Chloro-4-(1-methoxyethyl)-1,5-naphthyridin-3-yl)-N'-(6-(2H-1,2,3-triazol-2-yl)-5-(trifluoromethyl)pyridin-3-yl)urea

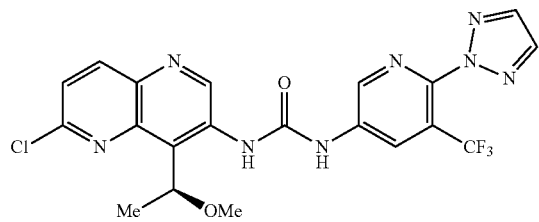 [SMILES: CO[C@@H](C)c1c(NC(=O)Nc2cnc(-n3nccn3)c(C(F)(F)F)c2)cnc2ccc(Cl)nc12]

A) tert-Butyl(6-chloro-2-(2-methoxypropanoyl)pyridin-3-yl)carbamate

To a mixture of tert-butyl(2-bromo-6-chloropyridin-3-yl)carbamate (20.0 g) and THF (160 mL) was added a 1.08 M methyllithium/diethyl ether solution (72.3 mL) at −78° C., followed by stirring at the same temperature for 15 minutes. A 1.6 M n-butyllithium/hexane solution (52.8 mL) was added to the resultant reaction mixture at −78° C., followed by stirring at the same temperature for 15 minutes. To the reaction mixture was added a solution of 2-methoxy-1-morpholinopropan-1-one (16.9 g) in THF (60 mL) at −78° C., followed by stirring for 2 hours with temperature rising to room temperature. A solution of acetic acid (15 mL) in water (150 mL) was added to the reaction mixture at room temperature, followed by extraction of the aqueous layer with ethyl acetate. The organic layer was washed with a saturated aqueous sodium hydrogen carbonate solution and saturated saline, and then dried over anhydrous magnesium sulfate, and the solvent was distilled off under reduced pressure. The residue was purified by silica gel column chromatography (ethyl acetate/hexane) to yield the title compound (15.81 g).

MS: $[M+H-tBu]^+$ 258.9.

B) 1-(6-Chloro-3-((2-nitrovinyl)amino)pyridin-2-yl)-2-methoxypropan-1-one

To a mixture of tert-butyl(6-chloro-2-(2-methoxypropanoyl)pyridin-3-yl)carbamate (15.7 g) and ethyl acetate (100 mL) was added a solution of 4 N hydrogen chloride in cyclopentyl methyl ether (200 mL) at room temperature, followed by stirring at the same temperature for 2 hours. To the resultant reaction mixture was further added a solution of 4 N hydrogen chloride in cyclopentyl methyl ether (100 mL) at room temperature, followed by stirring overnight at the same temperature, and the solvent was distilled off under reduced pressure. A mixture of the obtained residue, (E)-4-(2-nitrovinyl)morpholine (9.47 g), a 6 N hydrochloric acid solution (36 mL) and acetone (120 mL) was stirred at room temperature for 3 hours. The reaction mixture was diluted with water (240 mL), followed by stirring at 0° C. for 1 hour. The precipitate was collected by filtration and washed with water, and the obtained solid was dried under reduced pressure to yield the title compound (12.55 g).

MS: $[M+H]^+$ 286.0.

C) 2-Chloro-8-(1-methoxyethyl)-7-nitro-1,5-naphthyridine

To a mixture of DBU (6.62 mL) and THF (120 mL) was added a solution of 1-(6-chloro-3-((2-nitrovinyl)amino)pyridin-2-yl)-2-methoxypropan-1-one (12.55 g) in THF (280 mL) at room temperature, followed by stirring at the same temperature for 1 hour. After adjusting the pH to weakly acidic by adding a 2 N hydrochloric acid solution to the resultant reaction mixture, the mixture was diluted with water, followed by extraction of the aqueous layer with ethyl acetate. The organic layer was washed with saturated saline, and then dried over anhydrous magnesium sulfate, and the solvent was distilled off under reduced pressure. The residue was purified by silica gel column chromatography (ethyl acetate/hexane) to yield the title compound (9.82 g).

MS: $[M+H]^+$ 267.9.

D) 6-Chloro-4-(1-methoxyethyl)-1,5-naphthyridine-3-amine

A mixture of 2-chloro-8-(1-methoxyethyl)-7-nitro-1,5-naphthyridine (5.00 g), tin(II) chloride dihydrate (21.1 g) and ethyl acetate (150 mL) was stirred at 60° C. for 2 hours, and subsequently stirred at room temperature overnight. The resultant reaction mixture was diluted with ethyl acetate, and the mixture was neutralized with a 2 M aqueous potassium carbonate solution. The precipitate was filtered off, and then the aqueous layer of the filtrate was extracted with ethyl acetate. The organic layer was washed with saturated saline, and then dried over anhydrous magnesium sulfate, and the solvent was distilled off under reduced pressure. The residue was purified by silica gel column chromatography (NH, ethyl acetate/hexane) to yield the title compound (3.91 g).

MS: $[M+H]^+$ 238.0.

E) (S)-6-Chloro-4-(1-methoxyethyl)-1,5-naphthyridine-3-amine

6-Chloro-4-(1-methoxyethyl)-1,5-naphthyridine-3-amine (3.84 g) was fractioned by HPLC (CHIRALPAK IG (VJ003), 20 mm ID×250 mm L, mobile phase: hexane/ethanol=900/100). The fraction with a longer retention time containing the target product was concentrated under reduced pressure to yield the title compound (1865 mg).

Optical purity: 99.9% ee, retention time: 7.359 minutes (CHIRALPAK AD-H (VJ019), 4.6 mm ID×250 mm L, mobile phase: hexane/2-propanol=850/150)

MS: $[M+H]^+$ 238.0.

The absolute configuration was determined using a single crystal X-ray diffractometer.

F) (S)-N-(6-Chloro-4-(1-methoxyethyl)-1,5-naphthyridin-3-yl)-N'-(6-(2H-1,2,3-triazol-2-yl)-5-(trifluoromethyl)pyridin-3-yl)urea The reaction was carried out in the following 4 divided steps.

Reaction mixture 1: To a mixture of triphosgene (62 mg) and THF (5 mL) was added a solution of (S)-6-chloro-4-(1-methoxyethyl)-1,5-naphthyridine-3-amine (100 mg) and DIEA (0.220 mL) in THF (2 mL) at 0° C., followed by stirring at the same temperature for 1 hour. To the resultant reaction mixture was added 6-(2H-1,2,3-triazol-2-yl)-5-(trifluoromethyl)pyridine-3-amine (106 mg) obtained in Reference Example 2 at 0° C., followed by stirring at 60° C. overnight.

Reaction mixture 2: To a mixture of triphosgene (187 mg) and THF (12 mL) was added a solution of (S)-6-chloro-4-(1-methoxyethyl)-1,5-naphthyridine-3-amine (300 mg) and DIEA (0.660 mL) in THF (6 mL) at 0° C., followed by stirring at the same temperature for 1 hour. To the resultant reaction mixture was added 6-(2H-1,2,3-triazol-2-yl)-5-(trifluoromethyl)pyridine-3-amine (318 mg) obtained in Reference Example 2 at 0° C., followed by stirring at 60° C. for 2 hours. To the reaction mixture was added 6-(2H-1,2,3-triazol-2-yl)-5-(trifluoromethyl)pyridine-3-amine (29 mg) at the same temperature, followed by stirring overnight.

Reaction mixture 3: To a mixture of triphosgene (375 mg) and THF (24 mL) was added a solution of (S)-6-chloro-4-(1-methoxyethyl)-1,5-naphthyridine-3-amine (600 mg) and DIEA (1.32 mL) in THF (12 mL) at 0° C., followed by stirring at the same temperature for 1 hour. To the resultant reaction mixture was added 6-(2H-1,2,3-triazol-2-yl)-5-(trifluoromethyl)pyridine-3-amine (636 mg) obtained in Reference Example 2 at 0° C., followed by stirring at 60° C. for 2 hours. To the reaction mixture was added 6-(2H-1,2,3-triazol-2-yl)-5-(trifluoromethyl)pyridine-3-amine (116 mg) at the same temperature, followed by stirring overnight.

Reaction mixture 4: To a mixture of triphosgene (531 mg) and THF (34 mL) was added a solution of (S)-6-chloro-4-(1-methoxyethyl)-1,5-naphthyridine-3-amine (850 mg) and DIEA (1.87 mL) in THF (17 mL) at 0° C., followed by stirring at the same temperature for 1 hour. To the resultant reaction mixture was added 6-(2H-1,2,3-triazol-2-yl)-5-(trifluoromethyl)pyridine-3-amine (901 mg) obtained in Reference Example 2 at 0° C., followed by stirring at 60° C. for 2 hours. To the reaction mixture was added 6-(2H-1,2,3-triazol-2-yl)-5-(trifluoromethyl)pyridine-3-amine (164 mg) at the same temperature, followed by stirring overnight.

The reaction mixtures 1 to 4 were combined, and the combined mixture was diluted with a saturated aqueous sodium hydrogen carbonate solution, followed by extraction of the aqueous layer with ethyl acetate. The organic layer was washed with saturated saline, and then dried over anhydrous magnesium sulfate, and the solvent was distilled off under reduced pressure. THF and ethyl acetate were added to the residue, the insoluble material was filtered off, and the filtrate was concentrated under reduced pressure. The residue was purified by silica gel column chromatography (NH, ethyl acetate/hexane) to yield a crude crystal (3.46 g). The obtained crude crystal was dissolved in ethyl acetate (20 mL) at 80° C., and n-heptane (180 mL) was added dropwise to the mixed solution at the same temperature. The mixed solution was stirred at the same temperature for 1 hour, and then cooled to room temperature, followed by stirring at the same temperature overnight. The precipitate was collected by filtration, washed with a mixed solution of ethyl acetate and n-heptane, and then dried under reduced pressure to yield the title compound (3.35 g).

$^1$H NMR (300 MHz, DMSO-$d_6$) δ 1.56 (3H, d, J=6.4 Hz), 3.36 (3H, s), 5.85 (1H, q, J=6.7 Hz), 7.77 (1H, d, J=8.7 Hz), 8.18 (2H, s), 8.46 (1H, d, J=9.1 Hz), 8.74 (1H, d, J=2.6 Hz), 8.89 (1H, d, J=2.3 Hz), 9.24 (1H, s), 9.68 (1H, s), 10.89 (1H, s).

MS: [M−H]⁻ 491.1.

The absolute configuration was determined using a single crystal X-ray diffractometer.

Example 3

(S)-N-(4-(1-Methoxyethyl)-6-methyl-1,5-naphthyridin-3-yl)-N'-(6-(2H-1,2,3-triazol-2-yl)-5-(trifluoromethyl)pyridin-3-yl)urea

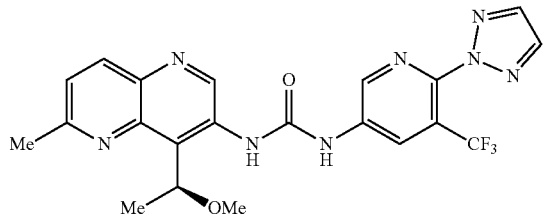 [SMILES: CO[C@@H](C)c1c(NC(=O)Nc2cnc(-n3nccn3)c(C(F)(F)F)c2)cnc2ccc(C)nc12]

A) 8-(1-Methoxyethyl)-2-methyl-7-nitro-1,5-naphthylene

A mixture of 2-chloro-8-(1-methoxyethyl)-7-nitro-1,5-naphthyridine (500 mg), 2,4,6-trimethylboroxin (0.39 mL), Pd(dppf)Cl$_2$/CH$_2$Cl$_2$ (153 mg), tripotassium phosphate (793 mg) and 1,2-dimethoxyethane (20 mL) was heated at 100° C. for 1.5 hours under irradiation with microwave. The resultant reaction mixture was diluted with ethyl acetate. The insoluble material was filtered off through Celite and washed with ethyl acetate. The filtrate was concentrated under reduced pressure. The residue was purified by silica gel column chromatography (ethyl acetate/hexane) to yield the title compound (439 mg).

MS: [M+H]⁺ 247.9.

B) 4-(1-Methoxyethyl)-6-methyl-1,5-naphthyridine-3-amine

A mixture of 8-(1-methoxyethyl)-2-methyl-7-nitro-1,5-naphthyridine (470 mg), tin(II) chloride dihydrate (2.57 g), THF (3 mL) and ethanol (12 mL) was stirred at room temperature overnight at 60° C. for 7 hours. The resultant reaction mixture was diluted with ethyl acetate, and neutralized with a saturated aqueous sodium hydrogen carbonate solution. The insoluble material was filtered off and washed with ethyl acetate. The filtrate was extracted twice with ethyl acetate. The organic layer was washed with saturated saline, and then dried over anhydrous magnesium sulfate, and the solvent was distilled off under reduced pressure. The residue was purified by silica gel column chromatography (ethyl acetate/hexane), followed by silica gel column chromatography (NH, ethyl acetate/hexane) to yield the title compound (306 mg).

MS: [M+H]⁺ 217.9.

C) N-(4-(1-Methoxyethyl)-6-methyl-1,5-naphthyridin-3-yl)-N'-(6-(2H-1,2,3-triazol-2-yl)-5-(trifluoromethyl)pyridin-3-yl)urea To a solution of 4-(1-methoxyethyl)-6-methyl-1,5-naphthyridine-3-amine (80 mg), 6-(2H-1,2,3-triazol-2-yl)-5-(trifluoromethyl)pyridine-3-amine (101 mg) obtained in Reference Example 2 and pyridine (0.089 mL) in THF (5 mL) was added a solution of triphosgene (54.6 mg) in THF (1 mL) at 0° C. The resultant reaction mixture was stirred at 0° C. for 30 minutes, and at room temperature for 30 minutes. Pyridine (0.089 mL) was added at 0° C., followed by a solution of triphosgene (54.6 mg) in THF (1 mL). The resultant reaction mixture was stirred at 0° C. for 30 minutes, and at room temperature for 4 hours. The mixture was poured into a saturated aqueous sodium hydrogen carbonate solution, followed by twice extraction with ethyl acetate. The organic layer was washed with saturated saline, and then dried over anhydrous magnesium sulfate, and the solvent was distilled off under reduced pressure. The residue was purified by silica gel column chromatography (NH, ethyl acetate/hexane) to yield the title compound (127 mg).

MS: [M+H]$^+$ 473.1.

D) (S)-N-(4-(1-Methoxyethyl)-6-methyl-1,5-naphthyridin-3-yl)-N'-(6-(2H-1,2,3-triazol-2-yl)-5-(trifluoromethyl)pyridin-3-yl)urea N-(4-(1-methoxyethyl)-6-methyl-1,5-naphthyridine-3-yl)-N'-(6-(2H-1,2,3-triazol-2-yl)-5-(trifluoromethyl)pyridin-3-yl)urea (119.8 mg) was fractioned by HPLC (CHIRALPAK AD-H (VA001), 20 mm ID×250 mm L, mobile phase: hexane/ethanol=700/300). The fraction with a shorter retention time containing the target product was concentrated under reduced pressure to yield the title compound (55.6 mg).

MS: [M+H]$^+$ 473.1.

Example 4

(S)-N-(5-Chloro-6-(2H-1,2,3-triazol-2-yl)pyridin-3-yl)-N'-(8-(1-methoxyethyl)-2-methylimidazo[1,2-b]pyridazin-7-yl)urea

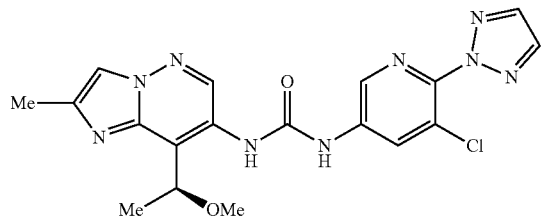 [SMILES: CO[C@@H](C)c1c(NC(=O)Nc2cnc(-n3nccn3)c(Cl)c2)cnn2cc(C)nc12]

To a solution of (S)-methyl 8-(1-methoxyethyl)-2-methylimidazo[1,2-b]pyridazine-7-carboxylate (743 mg) in THF (30 mL) was added an 8 M aqueous sodium hydroxide solution (4 mL) at room temperature. The resultant reaction mixture was stirred for 2 days. The reaction mixture was concentrated under reduced pressure, and then the residue was extracted with ethyl acetate. The aqueous layer was adjusted to pH 4 with a 6 N hydrochloric acid solution, and concentrated under reduced pressure. The residue was suspended in ethanol, the insoluble material was filtered off, and the filtrate was concentrated under reduced pressure. To a solution of the residue (848 mg) and triethylamine (1.51 mL) in toluene (50 mL) was added DPPA (1.16 mL) at room temperature. After the mixture was stirred at room temperature for 40 minutes, 5-chloro-6-(2H-1,2,3-triazol-2-yl)pyridine-3-amine (705 mg) obtained in Reference Example 3 was added. The resultant reaction mixture was stirred at 100° C. for 2 hours, and then poured into a saturated aqueous sodium hydrogen carbonate solution, followed by extraction with ethyl acetate. The organic layer was separated and washed with saturated saline, and then dried over anhydrous magnesium sulfate, and the solvent was distilled off under reduced pressure. The residue was purified by silica gel column chromatography (NH, methanol/ethyl acetate) and silica gel column chromatography (ethyl acetate/hexane) to yield the title compound (488 mg).

$^1$H NMR (300 MHz, DMSO-d$_6$) δ 1.54 (3H, d, J=6.4 Hz), 2.37 (3H, s), 3.33 (3H, s), 5.29 (1lH, q, J=6.8 Hz), 7.96 (1H, d, J=0.8 Hz), 8.16 (2H, s), 8.47-8.52 (1H, m), 8.54 (1lH, d,J=2.3 Hz), 8.75 (1H, brs), 9.04 (1H, s), 10.59 (1H, brs).

MS: [M+H]$^+$ 428.0.

Example 5

(S)-N-(5-Cyano-6-(difluoromethoxy)pyridin-3-yl)-N'-(8-(I-methoxyethyl)-2-methylimidazo[1,2-b]pyridazin-7-yl)urea

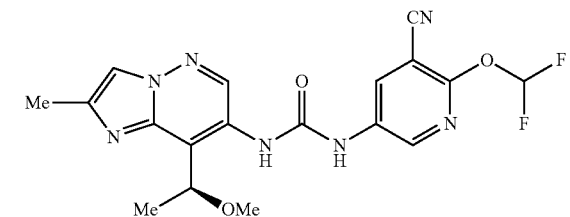 [SMILES: CO[C@@H](C)c1c(NC(=O)Nc2cnc(OC(F)F)c(C#N)c2)cnn2cc(C)nc12]

To a mixture of(S)-8-(1-methoxyethyl)-2-methylimidazo[1,2-b]pyridazine-7-carboxylic acid trifluoroacetate (80 mg), TEA (0.17 mL) and toluene (5 mL) was added DPPA (0.12 mL) at room temperature, followed by stirring of the resultant reaction mixture at the same temperature for 30 minutes. Furthermore, DPPA (0.12 mL) was added at room temperature, followed by stirring of the reaction mixture at the same temperature for 30 minutes. 5-Amino-2-(difluoromethoxy)nicotinonitrile (57.9 mg) obtained in Reference Example 4 was added, followed by stirring of the reaction mixture at 110° C. for 3 hours. To the reaction mixture was added a saturated aqueous sodium hydrogen carbonate solution, followed by extraction with ethyl acetate. The organic layer was washed with saturated saline, and then dried over anhydrous magnesium sulfate, and the solvent was distilled off under reduced pressure. The residue was purified by silica gel column chromatography (NH, ethyl acetate/hexane), and suspended in and washed with ethyl acetate/hexane to yield the title compound (65 mg).

$^1$H NMR (300 MHz, DMSO-d$_6$) δ 1.53 (3H, d, J=6.8 Hz), 2.36 (3H, s), 3.31 (3H, s), 5.22-5.31 (1H, m), 7.47-7.98 (1H, m), 7.93 (1H, d, J=0.8 Hz), 8.51-8.57 (2H, m), 8.68 (1H, brs), 9.01 (1H, s), 10.33 (1H, brs).

MS: [M+H]$^+$ 418.1.

Example 6

(S)-N-(8-(1-Methoxyethyl)-2-methylimidazo[1,2-b]pyridazin-7-yl)-N'-(6-(2H-1,2,3-triazol-2-yl)-5-(trifluoromethyl)pyridin-3-yl)urea

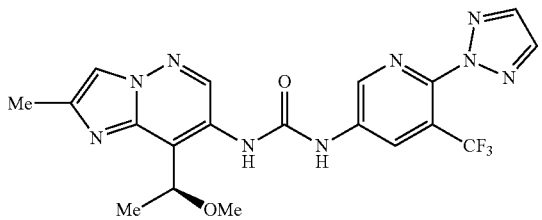 [SMILES: CO[C@@H](C)c1c(NC(=O)Nc2cnc(-n3nccn3)c(C(F)(F)F)c2)cnn2cc(C)nc12]

A) 8-(1-Methoxyethyl)-2-methylimidazo[1,2-b]pyridazine-7-carboxylic acid

To a solution of methyl 8-(1-methoxyethyl)-2-methylimidazo[1,2-b]pyridazine-7-carboxylate (262 mg) in methanol was added an 8 M aqueous sodium hydroxide solution (0.53 mL) at room temperature, followed by stirring at the same temperature for 5 hours. The resultant reaction mixture was neutralized with a 2 N hydrochloric acid solution, and concentrated under reduced pressure. The residue was suspended in ethyl acetate, and the insoluble material was filtered off. The filtrate was concentrated under reduced pressure to yield the title compound (256 mg).

MS: [M+H]+ 235.9.

B) N-(8-(1-Methoxyethyl)-2-methylimidazo[1,2-b]pyridazin-7-yl)-N'-(6-(2H-1,2,3-triazol-2-yl)-5-(trifluoromethyl)pyridin-3-yl)urea To a solution of 8-(1-methoxyethyl)-2-methylimidazo[1,2-b]pyridazine-7-carboxylic acid (166 mg) and triethylamine (0.30 mL) in toluene (10 mL) was added DPPA (0.18 mL) at room temperature. After the mixture was stirred at room temperature for 40 minutes, 6-(2H-1,2,3-triazol-2-yl)-5-(trifluoromethyl)pyridine-3-amine (162 mg) obtained in Reference Example 2 was added. The resultant reaction mixture was stirred at 100° C. for 2 hours, and then poured into a saturated aqueous sodium hydrogen carbonate solution, followed by extraction with ethyl acetate. The organic layer was separated and washed with saturated saline, and then dried over anhydrous magnesium sulfate, and the solvent was distilled off under reduced pressure. The residue was purified by silica gel column chromatography (NH, methanol/ethyl acetate), and suspended in and washed with ethyl acetate/hexane to yield the title compound (183 mg).

MS: [M+H]+ 462.1.

C) (S)-N-(8-(1-Methoxyethyl)-2-methylimidazo[1,2-b]pyridazin-7-yl)-N'-(6-(2H-1,2,3-triazol-2-yl)-5-(trifluoromethyl)pyridin-3-yl)urea N-(8-(1-Methoxyethyl)-2-methylimidazo(1,2-b]pyridazin-7-yl)-N'-(6-(2H-1,2,3-triazol-2-yl)-5-(trifluoromethyl)pyridin-3-yl)urea (183 mg) was fractionated by HPLC (CHIRALPAK IC (VB004), 20 mm ID×250 mm L, mobile phase: hexane/2-propanol=300/700). The fraction with a shorter retention time containing the target product was concentrated under reduced pressure. The concentrate was washed with ethyl acetate/hexane to yield the title compound (62 mg).

1H NMR (300 MHz, DMSO-d6) δ 1.55 (3H, d, J=6.8 Hz), 2.37 (3H, d, J=0.8 Hz), 3.33 (3H, s), 5.24-5.34 (1H, m), 7.96 (1H, d, J=0.8 Hz), 8.17 (2H, s), 8.72 (1H, d, J=2.3 Hz), 8.80 (1H, brs), 8.83 (1H, d, J=2.3 Hz), 9.06 (1H, s), 10.75 (1H, brs).

MS: [M+H]+ 462.1.

Example 7

N-(5-Chloro-6-(2H-1,2,3-triazol-2-yl)pyridin-3-yl)-N'-(8-(2-methoxypropan-2-yl)-2-methylimidazo[1,2-b]pyridazin-7-yl)urea

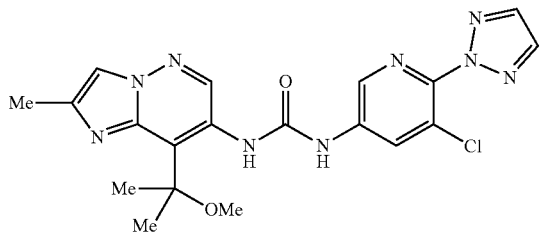 [SMILES: COC(C)(C)c1c(NC(=O)Nc2cnc(-n3nccn3)c(Cl)c2)cnn2cc(C)nc12]

A) 1-(Triphenylmethyl)-1H-imidazole

To a solution of imidazole (25 g) in methylene chloride (300 mL) was added TEA (77 mL) at 0° C. After the mixture was stirred for 5 minutes, triphenylmethyl chloride (102 g) was added little by little at the same temperature. The resultant reaction mixture was stirred at room temperature for 12 hours. The reaction mixture was diluted with water, and then extracted twice with methylene chloride. The organic layer was washed with water, followed by saturated saline, dried over sodium sulfate, and then concentrated under reduced pressure. The residue was washed with hexane to yield the title compound (110 g).

1H NMR (300 MHz, CDCl3) δ 6.82 (1H, s), 7.06 (1H, s), 7.08-7.15 (6H, m), 7.26-7.34 (9H, m), 7.45 (1 H, s).

B) 2-Methoxy-2-methyl-1-(1-(triphenylmethyl)-1H-imidazol-2-yl)propan-1-one

To a solution of 1-(triphenylmethyl)-1H-imidazole (1.0 g) in THF (15 mL) was added dropwise a solution of 1.4 M n-butyllithium/hexane (2.3 mL) at −10° C., followed by stirring at 0° C. for 30 minutes. After the resultant reaction mixture was cooled to −78° C., methyl 2-methoxy-2-methylpropionate (0.5 g) was added dropwise, followed by stirring at the same temperature for 1 hour and then at room temperature for 3 hours. To the reaction mixture was added a saturated aqueous ammonium chloride solution, followed by twice extraction with ethyl acetate. The organic layer was washed with water, followed by saturated saline, dried over magnesium sulfate, and then concentrated under reduced pressure. The residue was suspended in and washed with hexane to yield the title compound (650 mg).

1H NMR (300 MHz, CDCl3) δ 1.38 (6H, s), 2.67 (3H, s), 7.02-7.15 (12H, m), 7.25-7.35 (5H, m).

C) 1-(1 H-Imidazol-2-yl)-2-methoxy-2-methylpropan-1-one

A mixture of 2-methoxy-2-methyl-1-(1-(triphenylmethyl)-1H-imidazol-2-yl)propan-1-one (4.2 g) and a 5% acetic acid-methanol solution (50 mL) was refluxed for 16 hours. The resultant reaction mixture was cooled to room temperature, and then concentrated under reduced pressure. The residue was purified by silica gel column chromatography (ethyl acetate/hexane) to yield the title compound (1.2 g).

MS: [M+H]+ 169.2.

D) 1-(1-Amino-1H-imidazol-2-yl)-2-methoxy-2-methylpropan-1-one

To a solution of 1-(1H-imidazol-2-yl)-2-methoxy-2-methylpropan-1-one (1.4 g) in DMF (15 mL) was added a solution of 1 M potassium tert-butoxide in THF (9.2 mL), followed by stirring at the same temperature for 30 minutes. To the obtained mixture was added O-(4-nitrobenzoyl)hydroxylamine (1.7 g) at room temperature, followed by stirring at the same temperature for 16 hours. To the reaction mixture was added cold water, followed by concentration under reduced pressure. The residue was diluted with ethyl acetate, and the insoluble material was filtered off. The filtrate was concentrated under reduced pressure, and the residue was purified by silica gel column chromatography (ethyl acetate/hexane) to yield the title compound (1.0 g).
MS: [M+H]$^+$ 184.1.

E) N-(2-(2-(2-Methoxy-2-methylpropanoyl)-1H-imidazol-1-yl)(tert-butoxy)formamide To a solution of 1-(1-amino-1H-imidazol-2-yl)-2-methoxy-2-methylpropan-I-one (1.0 g) in DMF (10 mL) was added DMAP (0.34 g), followed by Boc$_2$0 (1.2 mL) at room temperature. The resultant reaction mixture was stirred at 80° C. for 1 hour, then cooled to room temperature, and concentrated under reduced pressure. The residue was purified by silica gel column chromatography (ethyl acetate/hexane) to yield the title compound (1.1 g).
MS: [M+H]$^+$ 284.2.

F) N-(4-Bromo-2-(2-(2-methoxy-2-methylpropanoyl)-1H-imidazol-1-yl)(tert-butoxy)formamide To a solution of N-(2-(2-(2-methoxy-2-methylpropanoyl)-1H-imidazol-1-yl)(tert-butoxy)formamide (1.0 g) in DMF (10 mL) was added dropwise a solution of N-bromosuccinimide (0.82 g) in DMF (5 mL), followed by stirring at room temperature for 16 hours. To the reaction mixture was added a saturated aqueous sodium carbonate solution, followed by concentration under reduced pressure. The residue was extracted twice with ethyl acetate, and the organic layer was washed with water, followed by saturated saline, dried over sodium sulfate, and then concentrated under reduced pressure. The residue was purified by silica gel column chromatography (ethyl acetate/hexane) to yield the title compound (700 mg).
MS: [M+H]$^+$ 362.0.

G) 1-(1-Amino-4-bromo-1H-imidazol-2-yl)-2-methoxy-2-methylpropan-1-one

To a solution of N-(4-bromo-2-(2-(2-methoxy-2-methylpropanoyl)-1H-imidazol-1-yl)(tert-butoxy)formamide (700 mg) in methylene chloride (10 mL) was added trifluoroacetic acid (3 mL) at 0° C., followed by stirring at room temperature for 1 hour. The resultant reaction mixture was concentrated under reduced pressure, and the residue was neutralized with a saturated aqueous sodium hydrogen carbonate solution. The mixture was extracted twice with ethyl acetate. The organic layer was washed with water, followed by saturated saline, washed with sodium sulfate, and then concentrated under reduced pressure. The residue was washed with pentane to yield the title compound (450 mg).
MS: [M+H]$^+$ 262.0.

H) Methyl 2-bromo-8-(2-methoxypropan-2-yl)imidazo[1,2-b]pyridazine-7-carboxylate To a solution of 1-(1-amino-4-bromo-1H-imidazol-2-yl)-2-methoxy-2-methylpropan-1-one (400 mg) in THF (5 mL) were added methyl acrylate (0.3 mL) and lithium bromide (531 mg) at room temperature. The mixture was placed in an oxygen atmosphere, Pd(OAc)$_2$ (69 mg) was added, and the mixture was stirred under an oxygen atmosphere at 50° C. for 16 hours. The resultant reaction mixture was poured into water, followed by twice extraction with ethyl acetate. The organic layer was washed with water, followed by saturated saline. The organic layer was dried over sodium sulfate, and then concentrated under reduced pressure. The residue was purified by silica gel column chromatography (ethyl acetate/hexane) to yield the title compound (250 mg).
MS: [M+H]$^+$ 328.1.

I) Methyl 2-methyl-8-(2-methoxypropan-2-yl)imidazo[I,2-b]pyridazine-7-carboxylate To a solution of methyl 2-bromo-8-(2-methoxypropan-2-yl)imidazo[1,2-b]pyridazine-7-carboxylate (200 mg) in toluene (6 mL) and water (0.4 mL) were added 2,4,6-trimethylboroxin (0.15 mL) and tripotassium phosphate (390 mg). Then, the mixture was placed in a nitrogen atmosphere. Pd(OAc)$_2$ (28 mg) and SPhos (101 mg) were added, and the mixture was stirred at 80° C. for 3 hours. The resultant reaction mixture was poured into an aqueous sodium hydrogen carbonate solution, followed by twice extraction with ethyl acetate. The organic layer was washed with water and saturated saline, dried over sodium sulfate, and then concentrated under reduced pressure. The residue was purified by silica gel column chromatography (ethyl acetate/hexane) to yield the title compound (120 mg).
MS: [M+H]$^+$ 264.0.

J) Methyl 2-methyl-8-(2-methoxypropan-2-yl)imidazo[1,2-b]pyridazine-7-carboxylic acid To a solution of methyl 2-methyl-8-(2-methoxypropan-2-yl)imidazo[1,2-b]pyridazine-7-carboxylate (300 mg) in ethanol (10 mL) was added an 8 M aqueous sodium hydroxide solution (0.72 mL), followed by stirring of the resultant reaction mixture at 60° C. overnight. An 8 M aqueous sodium hydrogen solution (1.44 mL) was added, followed by stirring at 80° C. overnight. 6 M Hydrochloric acid was added to the reaction mixture to make it acidic at pH 4, followed by concentration under reduced pressure. The residue was suspended in ethanol, and the insoluble material was filtered off and washed with ethanol. The filtrate was concentrated under reduced pressure while being azeotropically boiled with toluene to yield the title compound (406 mg).
MS: [M+H]$^+$ 250.0.

K) N-(5-Chloro-6-(2H-1,2,3-triazol-2-yl)pyridin-3-yl)-N'-(8-(2-methoxypropan-2-yl)-2-methylimidazo[1,2-b]pyridazin-7-yl)urea To a mixture of methyl 2-methyl-8-(2-methoxypropan-2-yl)imidazo[1,2-b]pyridazine-7-carboxylic acid (50 mg) and triethylamine (0.04 mL) in DMF (5 mL) was added DPPA (0.05 mL), followed by stirring at room temperature for 2 hours. To the reaction mixture was added a saturated aqueous sodium hydrogen carbonate solution, followed by extraction with ethyl acetate. The organic layer was washed with saturated saline, dried over magnesium sulfate, and then concentrated under reduced pressure. To the residue were added toluene (5 mL), triethylamine (0.04 mL) and 5-chloro-6-(2H-1,2,3-triazol-2-yl)pyridine-3-amine (27.5 mg) obtained in Reference Example 3, followed by stirring at 110° C. for 3 hours. To the reaction mixture was added a saturated aqueous sodium hydrogen carbonate solution, followed by extraction with ethyl acetate. The organic layer was washed with saturated saline, dried over magnesium sulfate, and then concentrated under reduced pressure. The residue was purified by HPLC to yield the title compound (2 mg).

$^1$H NMR (300 MHz, CDCl$_3$) δ 1.95 (6H, s), 2.44 (3H, d, J=0.8 Hz), 3.29 (3H, s), 7.64 (1H, d, J=0.8 Hz), 7.70 (1H, s), 7.88-7.99 (2H, m), 8.38 (1H, d, J=2.6 Hz), 8.57 (1H, d, J=2.6 Hz), 9.17 (1 H, s), 9.58 (11H, s).

MS: [M+H]$^+$ 442.1.

Example 8

N-(5-Chloro-6-(difluoromethoxy)pyridin-3-yl)-N'-(2-chloro-8-(propan-2-yl)imidazo[1,2-b]pyridazin-7-yl)urea

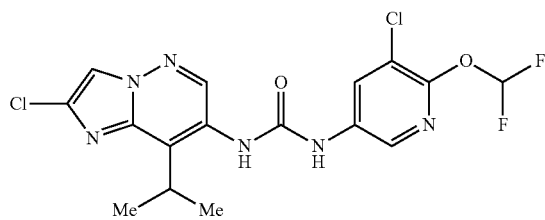 [SMILES: CC(C)c1c(NC(=O)Nc2cnc(OC(F)F)c(Cl)c2)cnn2cc(Cl)nc12]

A) Ethyl 1-amino-1H-imidazole-2-carboxylate

A solution of 1 M lithium hexamethyldisilazide in THF (171 mL) was added dropwise to a solution of ethyl imidazole-2-carboxylate (20 g) in anhydrous DMF (400 mL) at −10° C. under a nitrogen atmosphere, followed by stirring at the same temperature for 30 minutes. A solution of O-diphenylphosphinyl hydroxylamine (39.9 g) in anhydrous DMF (1000 mL) was added at 0° C. The resultant reaction mixture was stirred at room temperature for 16 hours, and then concentrated under reduced pressure. To the residue was added water, followed by 4 times extraction with methylene chloride. The extract was washed twice with saturated saline, then dried over anhydrous sodium sulfate, and concentrated under reduced pressure to yield the title compound (23.0 g).

$^1$H NMR (400 MHz, DMSO-d$_6$) δ 1.31 (3H, t, J=7.2 Hz), 4.30 (2H, q, J=7.2 Hz), 6.59 (2H, brs), 6.98 (11H, d, J=0.8 Hz), 7.39 (1H, d, J=0.8 Hz).

B) Ethyl 1-((tert-butoxycarbonyl)amino)-1H-imidazole-2-carboxylate

To a solution of ethyl 1-amino-1H-imidazole-2-carboxylate (23.0 g) and DMAP (8.72 g) in anhydrous DMF (250 mL) was added dropwise Boc$_2$O (28.0 g). The mixture was stirred under a nitrogen atmosphere at 80 to 85° C. for 4 hours, and then concentrated under reduced pressure. The residue was diluted with methylene chloride, and washed with a saturated aqueous citric acid solution, followed by saturated saline. The drying was carried out over anhydrous sodium sulfate, followed by concentration under reduced pressure. The residue was purified by silica gel column chromatography (ethyl acetate/methylene chloride) to yield the title compound (26.6 g).

$^1$H NMR (400 MHz, MeOD) δ 1.40 (3H, t, J=7.2 Hz), 1.52 (9H, s), 4.39 (2H, q, J=7.2 Hz), 7.15 (1H, d, J=1.2 Hz), 7.39 (11H, d, J=1.2 Hz).

C) Ethyl 1-((tert-butoxycarbonyl)amino)-4-chloro-1H-imidazole-2-carboxylate

To a solution of ethyl 1-((tert-butoxycarbonyl)amino)-1H-imidazole-2-carboxylate (80.0 g) in anhydrous DMF (800 mL) was added N-chlorosuccinimide (50.2 g) little by little, followed by stirring at room temperature for 16 hours under a nitrogen atmosphere. The resultant reaction mixture was diluted with water and extracted 3 times with ethyl acetate. The organic layer was washed twice with water and twice with saturated saline, dried over anhydrous sodium sulfate, and then concentrated under reduced pressure. The residue was purified by silica gel column chromatography (ethyl acetate/petroleum ether) to yield the title compound (16.8 g).

$^1$H NMR (400 MHz, CDCl$_3$) δ 1.39 (3H, t, J=7.2 Hz), 1.49 (9H, s), 4.39 (2H, q, J=7.2 Hz), 7.16 (11H, s), 8.07 (11H, brs).

D) Ethyl 3-(1-((tert-butoxycarbonyl)amino)-4-chloro-1H-imidazol-2-yl)-3-oxopropanate To a solution of ethyl 1-((tert-butoxycarbonyl)amino)-4-chloro-1H-imidazol-2-carboxylate (22.0 g) and ethyl acetate (33.5 g) in anhydrous THF (250 mL) was added dropwise a solution of 1 M lithium hexamethyldisilazide in THF (266 mL) at −10° C. under a nitrogen atmosphere. The resultant reaction mixture was stirred at the same temperature for 30 minutes, and then at room temperature for 4.5 hours. After the reaction mixture was cooled to 0° C., acetic acid was added to adjust the pH to 5, and then the pH was adjusted to 8 with a saturated aqueous sodium hydrogen carbonate solution. After extraction with ethyl acetate three times, the organic layer was washed twice with saturated saline, dried over sodium sulfate, and then concentrated under reduced pressure. The residue was purified by silica gel column chromatography (ethyl acetate/methylene chloride) to yield the title compound (19.7 g).

$^1$H NMR (400 MHz, CDCl$_3$) δ 1.26 (3H, t, J=7.2 Hz), 1.50 (9H, s), 4.05 (2H, s), 4.19 (2H, q, J=6.8 Hz), 7.25 (1H, s), 8.31 (1H, brs).

E) Ethyl 2-chloro-8-hydroxyimidazo[1,2-b]pyridazine-7-carboxylate

To a solution of ethyl 3-(1-((tert-butoxycarbonyl)amino)-4-chloro-1H-imidazol-2-yl)-3-oxopropanate (31.0 g) in anhydrous methylene chloride (400 mL) was added N,N-dimethylformamide dimethyl acetal (13.4 g). The resultant reaction mixture was stirred at room temperature for 16 hours, and then concentrated under reduced pressure. The residue was purified by silica gel column chromatography (methanol/methylene chloride) to yield the title compound (16.0 g).

MS: [M+H]$^+$ 241.9.

F) Ethyl 8-bromo-2-chloroimidazo[1,2-b]pyridazine-7-carboxylate

To a solution of ethyl 2-chloro-8-hydroxyimidazo[1,2-b]pyridazine-7-carboxylate (16.0 g) in acetonitrile (150 mL) was added phosphorus oxybromide (30.4 g), followed by stirring of the resultant reaction mixture at 80 to 90° C. for 2 hours under a nitrogen atmosphere. After the mixture was cooled to room temperature, ice water was added, followed by neutralization with a saturated aqueous sodium hydrogen carbonate solution. The mixture was extracted 3 times with ethyl acetate. The organic layer was washed twice with water and twice with saturated saline, dried over sodium sulfate, and then concentrated under reduced pressure. The residue was purified by silica gel column chromatography (ethyl acetate/petroleum ether) to yield the title compound (8.24 g).

$^1$H NMR (400 MHz, CDCl$_3$) δ 1.45 (3H, t, J=7.2 Hz), 4.47 (2H, q, J=7.2 Hz), 8.03 (1H, s), 8.71 (1H, s).

G) Ethyl 2-chloro-8-(propen-2-yl)imidazo[1,2-b]pyridazine-7-carboxylate

A mixture of ethyl 8-bromo-2-chloroimidazo[1,2-b]pyridazine-7-carboxylate (1.0 g), potassium isopropenyltrifluoroborate (534 mg), tripotassium phosphate (2.09 g), 1,1'-bis(diphenylphosphino)ferrocene palladium(II) chloride (240 mg), anhydrous DMF (5 mL) and anhydrous 1,4-dioxane (15 mL) was stirred at 80 to 85° C. for 16 hours under a nitrogen atmosphere. The resultant reaction mixture was cooled to room temperature, and then diluted with ethyl acetate. The organic layer was washed twice with water, and with saturated saline, dried over sodium sulfate, and then concentrated under reduced pressure. The residue was purified by silica gel column chromatography (ethyl acetate/petroleum ether) to yield the title compound (715 mg).

MS: [M+H]$^+$ 265.9.

H) Ethyl 2-chloro-8-(propan-2-yl)imidazo[1,2-b]pyridazine-7-carboxylate

A mixture of ethyl 2-chloro-8-(propen-2-yl)imidazo[1,2-b]pyridazine-7-carboxylate (1.20 g) and tris(triphenylphosphine)rhodium(I) chloride (418 mg) in anhydrous ethanol (30 mL) was stirred at 10 to 15° C. for 40 hours under a hydrogen atmosphere. The mixture was concentrated under reduced pressure. The residue was purified by silica gel column chromatography (ethyl acetate/petroleum ether) to yield the title compound (955 mg).

$^1$H NMR (400 MHz, CDCl$_3$) δ 1.43 (3H, t, J=7.2 Hz), 1.59 (6H, d, J=7.2 Hz), 4.09-4.22 (1H, m), 4.43 (2H, q, J=7.2 Hz), 7.88 (1H, s), 8.59 (1H, s).

I) 2-Chloro-8-(propan-2-yl)imidazo[1,2-b]pyridazine-7-carboxylic acid

To a solution of ethyl 2-chloro-8-(propan-2-yl)imidazo[1,2-b]pyridazine-7-carboxylate (955 mg) in methanol (10 mL), THF (10 mL) and water (10 mL) was added sodium hydroxide (571 mg), followed by stirring of the mixture at 10° C. for 1 hour under a nitrogen atmosphere. After a 2 N hydrochloric acid solution was added to the resultant reaction mixture to adjust the pH to 5, the mixture was extracted 3 times with ethyl acetate. The organic layer was washed twice with saturated saline, dried over sodium sulfate, and then concentrated under reduced pressure. The residue was washed with ethyl acetate/petroleum ether to yield the title compound (800 mg).

$^1$H NMR (400 MHz, DMSO-d$_6$) δ 1.49 (6H, d, J=6.8 Hz), 4.09-4.24 (1H, m), 8.57 (1H, s), 8.72 (1H, s), 13.97 (1H, brs).

J) N-(5-Chloro-6-(difluoromethoxy)pyridin-3-yl)-N'-(2-chloro-8-(propan-2-yl)imidazo[1,2-b]pyridazin-7-yl)urea To a mixture of 2-chloro-8-(propan-2-yl)imidazo[1,2-b]pyridazine-7-carboxylic acid (60 mg) and triethylamine (51 mg) in dioxane (3 mL) was added DPPA (130 mg) at 10° C. After the mixture was stirred at the same temperature for 30 minutes, 5-chloro-6-(difluoromethoxy)pyridine-3-amine (58 mg) obtained in Reference Example 1 was added, followed by stirring at 100° C. for 1 hour under a nitrogen atmosphere. The resultant reaction mixture was concentrated under reduced pressure. The residue was purified by silica gel column chromatography (ethyl acetate/petroleum ether), followed by HPLC to yield the title compound (31 mg).

$^1$H NMR (400 MHz, DMSO-d$_6$) δ 1.46 (6H, d, J=6.8 Hz), 3.41-3.57 (1H, m), 7.67 (1H, t, J=72.8 Hz), 8.20-8.40 (3H, m), 8.71 (1H, s), 9.03 (1H, brs), 9.62 (1H, brs).

MS: [M+H]$^+$ 430.9.

Example 9

N-(5-chloro-6-(2H-1,2,3-triazol-2-yl)pyridin-3-yl)-N'-(2-methyl-8-(propan-2-yl)imidazo[1,2-b]pyridazin-7-yl)urea

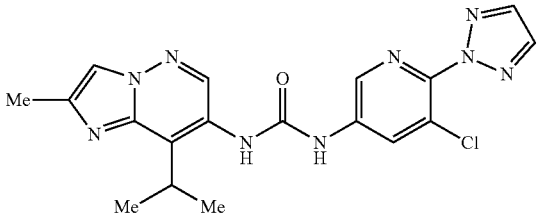 [SMILES: Cc1cn2ncc(NC(=O)Nc3cnc(-n4nccn4)c(Cl)c3)c(C(C)C)c2n1]

A) Methyl 2-chloro-8-(propan-2-yl)imidazo[1,2-b]pyridazine-7-carboxylate

To a solution of 2-chloro-8-(propan-2-yl)imidazo[1,2-b]pyridazine-7-carboxylic acid (462 mg) in methanol was add a solution of 0.6 M trimethylsilyldiazomethane in hexane (9.6 mL) at room temperature. The reaction mixture was stirred at room temperature for 1 hour, and then concentrated under reduced pressure to yield the title compound (475 mg).

MS: [M+H]$^+$ 254.1.

B) Methyl 2-methyl-8-(propan-2-yl)imidazo[1,2-b]pyridazine-7-carboxylate

To a mixture of methyl 2-chloro-8-(propan-2-yl)imidazo[1,2-b]pyridazine-7-carboxylate (475 mg), 2,4,6-trimethylboroxin (0.52 mL), tripotassium phosphate (1.92 g), SPhos (307 mg), toluene (3 mL) and water (0.3 mL) was added Pd(OAc)$_2$ (84 mg) under an argon atmosphere. The resultant reaction mixture was heated at 130° C. for 1 hour, and then poured into a saturated aqueous sodium hydrogen carbonate solution, followed by extraction with ethyl acetate. The organic layer was washed with saturated saline, dried over magnesium sulfate, and then concentrated under reduced pressure. The residue was purified by silica gel column chromatography (ethyl acetate/hexane) to yield the title compound (356 mg).

MS: [M+H]$^+$ 234.2.

C) 2-Methyl-8-(propan-2-yl)imidazo[1,2-b]pyridazine-7-carboxylic acid

To a solution of methyl 2-methyl-8-(propan-2-yl)imidazole[1,2-b]pyridazine-7-carboxylate (356 mg) in methanol (15 mL) was added a 2M aqueous sodium hydroxide solution (1.5 mL), followed by stirring of the mixture at room temperature for 2 hours. To the mixture was added an 8M aqueous sodium hydroxide solution (0.76 mL), followed by stirring at room temperature for 4 hours. After a 1 N hydrochloric acid solution was added to the resultant reaction mixture at 0° C. for neutralization, the mixture was extracted with ethyl acetate. The organic layer was washed with water, followed by saturated saline, dried over magnesium sulfate, and then concentrated under reduced pressure to yield the title compound (254 mg).

MS: [M+H]$^+$ 220.2.

D) N-(5-chloro-6-(2H-1,2,3-triazol-2-yl)pyridin-3-yl)-N'-(2-methyl-8-(propan-2-yl)imidazo[1,2-b]pyridazin-7-yl)urea To a solution of 2-methyl-8-(propan-2-yl)imidazo[1,2-b]pyridazine-7-carboxylic acid (80 mg) and triethylamine (0.15 mL) in toluene (10 mL) was added diphenylphosphoryl azide (0.09 mL). After the mixture was stirred at the same temperature for 40 minutes, 5-chloro-6-(2H-1,2,3-triazol-2-yl)pyridine-3-amine (71 mg) obtained in Reference Example 3 was added, followed by stirring at 100° C. for 2 hours. The resultant reaction mixture was poured into a saturated aqueous sodium hydrogen carbonate solution, followed by extraction with ethyl acetate. The organic layer was washed with saturated saline, dried over magnesium sulfate, and then concentrated under reduced pressure. The residue was purified by silica gel column chromatography (ethyl acetate/hexane), and suspended in and washed with ethyl acetate/hexane to yield the title compound (83 mg).

$^1$H NMR (300 MHz, DMSO-d$_6$) δ 1.49 (6H, d, J=7.2 Hz), 2.38 (3H, s), 3.48 (1H, quin, J=6.9 Hz), 7.93 (1H, d, J=0.8 Hz), 8.12-8.16 (2H, m), 8.46 (1H, d, J=2.3 Hz), 8.49 (1H, s), 8.57 (1H, d, J=2.3 Hz), 8.82 (1H, s), 9.73 (1H, brs).

MS: [M+H]$^+$ 412.2.

The following compounds of Examples 10 to 270 were synthesized in the same manner.

TABLE 1-1

| Example No. | | Salt | MS |
|---|---|---|---|
| 1 | (S)-N-(5-Chloro-6-(difluoromethoxy)pyridin-3-yl)-N'-(8-(1-methoxyethyl)-2-methylimidazo[1,2-b]pyridazin-7-yl)urea | | 427.0 |
| 2 | (S)-N-(6-Chloro-4-(1-methoxyethyl)-1,5-naphthyridin-3-yl)-N'-(6-(2H-1,2,3-triazol-2-yl)-5-(trifluoromethyl)pyridin-3-yl)urea | | 491.1 |
| 3 | (S)-N-(4-(1-Methoxyethyl)-6-methyl-1,5-naphthyridin-3-yl)-N'-(6-(2H-1,2,3-triazol-2-yl)-5-(trifluoromethyl)pyridin-3-yl)urea | | 473.0 |
| 4 | (S)-N-(5-Chloro-6-(2H-1,2,3-triazol-2-yl)pyridin-3-yl)-N'-(8-(1-methoxyethyl)-2-methylimidazo[1,2-b]pyridazin-7-yl)urea | | 428.1 |
| 5 | (S)-N-(5-Cyano-6-(difluoromethoxy)pyridin-3-yl)-N'-(8-(1-methoxyethyl)-2-methylimidazo[1,2-b]pyridazin-7-yl)urea | | 418.1 |
| 6 | (S)-N-(8-(1-Methoxyethyl)-2-methylimidazo[1,2-b]pyridazin-7-yl)-N'-(6-(2H-1,2,3-triazol-2-yl)-5-(trifluoromethyl)pyridin-3-yl)urea | | 461.9 |
| 7 | N-(5-Chloro-6-(2H-1,2,3-triazol-2-yl)pyridin-3-yl)-N'-(8-(2-methoxypropan-2-yl)-2-methylimidazo[1,2-b]pyridazin-7-yl)urea | | 442.1 |
| 8 | N-(5-Chloro-6-(difluoromethoxy)pyridin-3-yl)-N'-(2-chloro-8-(propan-2-yl)imidazo[1,2-b]pyridazin-7-yl)urea | | 429.0 |
| 9 | N-(5-Chloro-6-(2H-1,2,3-triazol-2-yl)pyridin-3-yl)-N'-(2-methyl-8-(propan-2-yl)imidazo[1,2-b]pyridazin-7-yl)urea | | 412.0 |
| 10 | (R)-N-(5-Chloro-6-(difluoromethoxy)pyridin-3-yl)-N'-(8-(1-methoxyethyl)-2-methylimidazo[1,2-b]pyridazin-7-yl)urea | HCl | 427.1 |
| 11 | (R)-N-(5-Chloro-6-(difluoromethoxy)pyridin-3-yl)-N'-(8-(1-methoxyethyl)-2-methylimidazo[1,2-b]pyridazin-7-yl)urea | H$_2$SO$_4$ | 427.1 |
| 12 | (S)-N-(6-Chloro-4(1-methoxyethyl)-1,5-naphthyridin-3-yl)-N'-(6-(2H-1,2,3-triazol-2-yl)-5-(trifluoromethyl)pyridin-3-yl)urea | HCl | 493.1 |
| 13 | (S)-N-(6-Chloro-4-(1-methoxyethyl)-1,5-naphthyridin-3-yl)-N'-(6-(2H-1,2,3-triazol-2-yl)-5-(trifluoromethyl)pyridin-3-yl)urea | 0.5H$_2$SO$_4$ | 493.1 |
| 14 | N-(5-Chloro-6-(difluoromethoxy)pyridin-3-yl)-N'-(8-(1-methoxyethyl)-2-methylimidazo[1,2-b]pyridazin-7-yl)urea | | 427.1 |

TABLE 1-2

| | | |
|---|---|---|
| 15 | (R)-N-(5-Chloro-6-(difluoromethoxy)pyridin-3-yl)-N'-(8-(1-methoxyethyl)-2-methylimidazo[1,2-b]pyridazin-7-yl)urea | 427.0 |
| 16 | N-(5-Cyanopyridin-3-yl)-N'-(8-(1-methoxyethyl)-2-methylimidazo[1,2-b]pyridazin-7-yl)urea | 350.1 |
| 17 | N-(8-(1-Methoxyethyl)-2-methylimidazo[1,2-b]pyridazin-7-yl)-N'-(6-(2H-1,2,3-triazol-2-yl)-5-(trifluoromethyl)pyridin-3-yl)urea | 462.0 |
| 18 | (R)-N-(8-(1-Methoxyethyl)-2-methylimidazo[1,2-b]pyridazin-7-yl)-N'-(6-(2H-1,2,3-triazol-2-yl)-5-(trifluoromethyl)pyridin-3-yl)urea | 461.9 |
| 19 | N-(5-Chloro-6-(2H-1,2,3-triazol-2-yl)pyridin-3-yl)-N'-(8-(1-methoxyethyl)-2-methylimidazo[1,2-b]pyridazin-7-yl)urea | 428.0 |
| 20 | (R)-N-(5-Chloro-6-(2H-1,2,3-triazol-2-yl)pyridin-3-yl)-N'-(8-(1-methoxyethyl)-2-methylimidazo[1,2-b]pyridazin-7-yl)urea | 428.2 |
| 21 | (S)-N-(5-Chloro-6-(3-methyl-1H-1,2,4-triazol-1-yl)pyridin-3-yl)-N'-(8-(1-methoxyethyl)-2-methylimidazo[1,2-b]pyridazin-7-yl)urea | 442.2 |
| 22 | (S)-N-(8-(1-Methoxyethyl)-2-methylimidazo[1,2-b]pyridazin-7-yl)-N'-(2-methyl-6-(2H-1,2,3-triazol-2-yl)-5-(trifluoromethyl)pyridin-3-yl)urea | 475.9 |

TABLE 1-2-continued

| | | |
|---|---|---|
| 23 | (S)-N-(5-Chloro-2-methyl-6-(2H-1,2,3-triazol-2-yl)pyridin-3-yl)-N'-(8-(1-methoxyethyl)-2-methylimidazo[1,2-b]pyridazin-7-yl)urea | 442.2 |
| 24 | (S)-N-(5-Chloro-6-(1,3-oxazol-2-yl)pyridin-3-yl)-N'-(8-(1-methoxyethyl)-2-methylimidazo[1,2-b]pyridazin-7-yl)urea | 428.1 |
| 25 | (S)-N-(5-Chloro-6-(1-methyl-1H-imidazol-4-yl)pyridin-3-yl)-N'-(8-(1-methoxyethyl)-2-methylimidazo[1,2-b]pyridazin-7-yl)urea | 441.1 |
| 26 | (S)-N-(8-(1-Methoxyethyl)-2-methylimidazo[1,2-b]pyridazin-7-yl)-N'-(6-(1,3-oxazol-2-yl)-5-(trifluoromethyl)pyridin-3-yl)urea | 462.2 |
| 27 | (S)-N-(8-(1-Methoxyethyl)-2-methylimidazo[1,2-b]pyridazin-7-yl)-N'-(5-methyl-6-(2H-1,2,3-triazol-2-yl)pyridin-3-yl)urea | 408.1 |

TABLE 1-3-continued

| | | | |
|---|---|---|---|
| 37 | (S)-N-(5-Chloro-6-(4-methyl-2H-1,2,3-triazol-2-yl)pyridin-3-yl)-N'-(8-(1-methoxyethyl)-2-methylimidazo[1,2-b]pyridazin-7-yl)urea | | 442.1 |
| 38 | (S)-N-(6-(Difluoromethoxy)-5-(difluoromethyl)pyridin-3-yl)-N'-(8-(1-methoxyethyl)-2-methylimidazo[1,2-b]pyridazin-7-yl)urea | | 443.1 |
| 39 | (S)-N-(5-Cyano-6-(2H-1,2,3-triazol-2-yl)pyridin-3-yl)-N'-(8-(1-methoxyethyl)-2-methylimidazo[1,2-b]pyridazin-7-yl)urea | | 418.9 |
| 40 | (S)-N-(5-Chloro-6-(difluoromethoxy)-2-methylpyridin-3-yl)-N'-(8-(1-methoxyethyl)-2-methylimidazo[1,2-b]pyridazin-7-yl)urea | | 441.1 |
| 41 | N-(6-Chloro-4-(1-methoxyethyl)-1,5-naphthyridin-3-yl)-N'-(5-cyanopyridin-3-yl)urea | | 381.0 |
| 42 | N-(6-Chloro-4-(1-methoxyethyl)-1,5-naphthyridin-3-yl)-N'-(6-(2H-1,2,3-triazol-2-yl)-5-(trifluoromethyl)pyridin-3-yl)urea | | 491.0 |

TABLE 1-4

| | | | |
|---|---|---|---|
| 43 | (R)-N-(6-Chloro-4-(1-methoxyethyl)-1,5-naphthyridin-3-yl)-N'-(6-(2H-1,2,3-triazol-2-yl)-5-(trifluoromethyl)pyridin-3-yl)urea | | 491.1 |
| 44 | (R)-N-(6-Chloro-4-(1-methoxyethyl)-1,5-naphthyridin-3-yl)-N'-(6-(2H-1,2,3-triazol-2-yl)-5-(trifluoromethyl)pyridin-3-yl)urea | HCl | 493.1 |
| 45 | (R)-N-(6-Chloro-4-(1-methoxyethyl)-1,5-naphthyridin-3-yl)-N'-(6-(2H-1,2,3-triazol-2-yl)-5-(trifluoromethyl)pyridin-3-yl)urea | 0.5$H_2SO_4$ | 493.1 |
| 46 | N-(6-Chloro-4-(1-methoxyethyl)-1,5-naphthyridin-3-yl)-N'-(1-methyl-3-(trifluoromethyl)-1H-pyrazol-5-yl)urea | | 427.1 |
| 47 | N-(6-Chloro-4-(1-methoxyethyl)-1,5-naphthyridin-3-yl)-N'-(5-chloro-6-(2H-1,2,3-triazol-2-yl)pyridin-3-yl)urea | | 459.1 |
| 48 | N-(6-Chloro-4-(1-methoxyethyl)-1,5-naphthyridin-3-yl)-N'-(5-chloro-6-(2H-1,2,3-triazol-2-yl)pyridin-3-yl)urea | | 459.1 |
| 49 | N-(6-Chloro-4-(1-methoxyethyl)-1,5-naphthyridin-3-yl)-N'-(5-chloro-6-(2H-1,2,3-triazol-2-yl)pyridin-3-yl)urea | | 459.1 |
| 50 | N-(6-Chloro-4-(1-methoxyethyl)-1,5-naphthyridin-3-yl)-N'-(5-cyano-6-(2H-1,2,3-triazol-2-yl)pyridin-3-yl)urea | | 448.1 |
| 51 | N-(6-Chloro-4-(1-methoxyethyl)-1,5-naphthyridin-3-yl)-N'-(5-chloro-6-methoxypyridin-3-yl)urea | | 421.9 |
| 52 | N-(5-Chloro-6-(2-methoxyethoxy)pyridin-3-yl)-N'-(6-chloro-4-(1-methoxyethyl)-1,5-naphthyridin-3-yl)urea | | 465.9 |
| 53 | N-(6-(Azetidin-1-yl)-5-chloropyridin-3-yl)-N'-(6-chloro-4-(1-methoxyethyl)-1,5-naphthyridin-3-yl)urea | | 447.0 |
| 54 | N-(6-Chloro-4-(1-methoxyethyl)-1,5-naphthyridin-3-yl)-N'-(5-chloro-6-(2-oxopyrrolidin-1-yl)pyridin-3-yl)urea | | 474.9 |
| 55 | N-(6-Chloro-4-(1-methoxyethyl)-1,5-naphthyridin-3-yl)-N'-(1-ethyl-3-(trifluoromethyl)-1H-pyrazol-5-yl)urea | | 443.0 |
| 56 | N-(6-Chloro-4-(1-methoxyethyl)-1,5-naphthyridin-3-yl)-N'-(3-(difluoromethyl)-1-methyl-1H-pyrazol-5-yl)urea | | 411.0 |

TABLE 1-2-continued

| | | |
|---|---|---|
| 28 | (S)-N-(6-(Difluoromethoxy)-5-methylpyridin-3-yl)-N'-(8-(1-methoxyethyl)-2-methylimidazo[1,2-b]pyridazin-7-yl)urea | 407.1 |

TABLE 1-3

| | | |
|---|---|---|
| 29 | (S)-N-(5-Chloro-6-(1-methyl-1H-1,2,4-triazol-3-yl)pyridin-3-yl)-N'-(8-(1-methoxyethyl)-2-methylimidazo[1,2-b]pyridazin-7-yl)urea | 442.1 |
| 30 | (S)-N-(8-(1-Methoxyethyl)-2-methylimidazo[1,2-b]pyridazin-7-yl)-N'-(6-(4-methyl-2H-1,2,3-triazol-2-yl)-5-(trifluoromethyl)pyridin-3-yl)urea | 476.2 |
| 31 | (S)-N-(5-(Difluoromethyl)-6-(2H-1,2,3-triazol-2-yl)pyridin-3-yl)-N'-(8-(1-methoxyethyl)-2-methylimidazo[1,2-b]pyridazin-7-yl)urea | 444.2 |
| 32 | (S)-N-(8-(1-Methoxyethyl)-2-methylimidazo[1,2-b]pyridazin-7-yl)-N'-[6-(4-(methoxymethyl)-2H-1,2,3-triazol-2-yl)-5-(trifluoromethyl)pyridin-3-yl]urea | 506.3 |
| 33 | (S)-N-(8-(1-Methoxyethyl)-2-methylimidazo[1,2-b]pyridazin-7-yl)-N'-(6-(3-methyl-1H-1,2,4-triazol-1-yl)-5-(trifluoromethyl)pyridin-3-yl)urea | 476.2 |
| 34 | (S)-N-[6-(4-(Difluoromethyl)-2H-1,2,3-triazol-2-yl)-5-(trifluoromethyl)pyridin-3-yl]-N'-(8-(1-methoxyethyl)-2-methylimidazo[1,2-b]pyridazin-7-yl)urea | 512.2 |
| 35 | (S)-N-(5-Bromo-6-(difluoromethoxy)pyridin-3-yl)-N'-(8-(1-methoxyethyl)-2-methylimidazo[1,2-b]pyridazin-7-yl)urea | 471.1 |
| 36 | (S)-N-[5-Chloro-6-(4-(methoxymethyl)-2H-1,2,3-triazol-2-yl)pyridin-3-yl]-N'-(8-(1-methoxyethyl)-2-methylimidazo[1,2-b]pyridazin-7-yl)urea | 472.2 |

TABLE 1-5

| | | |
|---|---|---|
| 57 | N-(6-Chloro-4-(1-methoxyethyl)-1,5-naphthyridin-3-yl)-N'-(5-fluoro-6-methoxypyridin-3-yl)urea | 406.0 |
| 58 | N-(6-Chloro-4-(1-methoxyethyl)-1,5-naphthyridin-3-yl)-N'-(2-cyano-5-methylpyridin-4-yl)urea | 397.2 |
| 59 | N-(5-Chloro-6-(difluoromethoxy)pyridin-3-yl)-N'-(6-chloro-4-(1-methoxyethyl)-1,5-naphthyridin-3-yl)urea | 456.0 |
| 60 | N-(5-Chloro-6-(difluoromethoxy)pyridin-3-yl)-N'-(6-chloro-4-(1-methoxyethyl)-1,5-naphthyridin-3-yl)urea | 458.1 |
| 61 | N-(5-Chloro-6-(difluoromethoxy)pyridin-3-yl)-N'-(6-chloro-4-(1-methoxyethyl)-1,5-naphthyridin-3-yl)urea | 458.1 |
| 62 | N-(6-Chloro-4-(1-methoxyethyl)-1,5-naphthyridin-3-yl)-N'-(2-methyl-6-(2H-1,2,3-triazol-2-yl)-5-(trifluoromethyl)pyridin-3-yl)urea | 507.1 |
| 63 | (R)-N-(6-Chloro-4-(1-methoxyethyl)-1,5-naphthyridin-3-yl)-N'-(2-methyl-6-(2H-1,2,3-triazol-2-yl)-5-(trifluoromethyl)pyridin-3-yl)urea | 507.1 |
| 64 | (R)-N-(6-Chloro-4-(1-methoxyethyl)-1,5-naphthyridin-3-yl)-N'-(5-chloro-2-methyl-6-(2H-1,2,3-triazol-2-yl)pyridin-3-yl)urea | 473.1 |
| 65 | (R)-N-(5-Chloro-6-(difluoromethoxy)-2-methylpyridin-3-yl)-N'-(6-chloro-4-(1-methoxyethyl)-1,5-naphthyridin-3-yl)urea | 472.0 |
| 66 | (S)-N-(6-Chloro-4-(1-methoxyethyl)-1,5-naphthyridin-3-yl)-N'-(2-methyl-6-(2H-1,2,3-triazol-2-yl)-5-(trifluoromethyl)pyridin-3-yl)urea | 507.2 |
| 67 | (S)-N-(5-Chloro-6-(difluoromethoxy)-2-methylpyridin-3-yl)-N'-(6-chloro-4-(1-methoxyethyl)-1,5-naphthyridin-3-yl)urea | 472.1 |
| 68 | (S)-N-(6-Chloro-4-(1-methoxyethyl)-1,5-naphthyridin-3-yl)-N'-(5-chloro-2-methyl-6-(2H-1,2,3-triazol-2-yl)pyridin-3-yl)urea | 473.2 |

TABLE 1-5-continued

| | | |
|---|---|---|
| 69 | (S)-N-(6-Chloro-4-(1-methoxyethyl)-1,5-naphthyridin-3-yl)-N'-(6-(1,3-oxazol-2-yl)-5-(trifluoromethyl)pyridin-3-yl)urea | 493.1 |
| 70 | (S)-N-(6-Chloro-4-(1-methoxyethyl)-1,5-naphthyridin-3-yl)-N'-(5-methyl-6-(2H-1,2,3-triazol-2-yl)pyridin-3-yl)urea | 439.1 5 |

TABLE 1-6

| | | |
|---|---|---|
| 71 | (S)-N-(6-Chloro-4-(1-methoxyethyl)-1,5-naphthyridin-3-yl)-N'-(5-chloro-6-(3-methyl-1H-1,2,4-triazol-1-yl)pyridin-3-yl)urea | 473.1 |
| 72 | (S)-N-(6-Chloro-4-(1-methoxyethyl)-1,5-naphthyridin-3-yl)-N'-(5-chloro-6-(1,3-oxazol-2-yl)pyridin-3-yl)urea | 459.1 |
| 73 | (S)-N-(6-Chloro-4-(1-methoxyethyl)-1,5-naphthyridin-3-yl)-N'-(5-chloro-6-(1-methyl-1H-1,2,4-triazol-3-yl)pyridin-3-yl)urea | 473.1 |
| 74 | (S)-N-(6-Chloro-4-(1-methoxyethyl)-1,5-naphthyridin-3-yl)-N'-(6-(difluoromethoxy)-5-methylpyridin-3-yl)urea | 438.1 |
| 75 | (S)-N-(6-Chloro-4-(1-methoxyethyl)-1,5-naphthyridin-3-yl)-N'-(5-cyano-6-(difluoromethoxy)pyridin-3-yl)urea | 449.1 |
| 76 | (S)-N-(6-Chloro-4-(1-methoxyethyl)-1,5-naphthyridin-3-yl)-N'-(6-(4-methyl-2H-1,2,3-triazol-2-yl)-5-(trifluoromethyl)pyridin-3-yl)urea | 507.2 |
| 77 | (S)-N-(6-Chloro-4-(1-methoxyethyl)-1,5-naphthyridin-3-yl)-N'-{6-(4-(methoxymethyl)-2H-1,2,3-triazol-2-yl)-5-(trifluoromethyl)pyridin-3-yl}urea | 537.2 |
| 78 | (S)-N-(6-Chloro-4-(1-methoxyethyl)-1,5-naphthyridin-3-yl)-N'-(6-(3-methyl-1H-1,2,4-triazol-1-yl)-5-(trifluoromethyl)pyridin-3-yl)urea | 507.2 |
| 79 | (S)-N-(6-Chloro-4-(1-methoxyethyl)-1,5-naphthyridin-3-yl)-N'-(5-(difluoromethyl)-6-(2H-1,2,3-triazol-2-yl)pyridin-3-yl)urea | 475.1 |
| 80 | (S)-N-(6-Chloro-4-(1-methoxyethyl)-1,5-naphthyridin-3-yl)-N'-(6-(4-(difluoromethyl)-2H-1,2,3-triazol-2-yl)-5-(trifluoromethyl)pyridin-3-yl)urea | 543.2 |
| 81 | (S)-N-(6-Chloro-4-(1-methoxyethyl)-1,5-naphthyridin-3-yl)-N'-(6-(difluoromethoxy)-5-(difluoromethyl)pyridin-3-yl)urea | 474.1 |
| 82 | (S)-N-(5-Bromo-6-(difluoromethoxy)pyridin-3-yl)-N'-(6-chloro-4-(1-methoxyethyl)-1,5-naphthyridin-3-yl)urea | 502.1 |
| 83 | N-(5-Chloro-6-(2H-1,2,3-triazol-2-yl)pyridin-3-yl)-N'-(4-(1-methoxyethyl)-6-methyl-1,5-naphthyridin-3-yl)urea | 439.1 |
| 84 | N-(4-(1-Methoxyethyl)-6-methyl-1,5-naphthyridin-3-yl)-N'-(6-(2H-1,2,3-triazol-2-yl)-5-(trifluoromethyl)pyridin-3-yl)urea | 473.1 |

TABLE 1-7

| | | | |
|---|---|---|---|
| 85 | (R)-N-(4-(1-Methoxyethyl)-6-methyl-1,5-naphthyridin-3-yl)-N'-(6-(2H-1,2,3-triazol-2-yl)-5-(trifluoromethyl)pyridin-3-yl)urea | | 472.9 |
| 86 | N-(5-Chloro-6-(difluoromethoxy)pyridin-3-yl)-N'-(4-(1-methoxyethyl)-6-methyl-1,5-naphthyridin-3-yl)urea | | 438.1 |
| 87 | N-(2-Cyano-5-methylpyridin-4-yl)-N'-(4-(1-methoxyethyl)-6-methyl-1,5-naphthyridin-3-yl)urea | | 377.2 |
| 88 | (R)-N-(4-(1-Methoxyethyl)-6-methyl-1,5-naphthyridin-3-yl)-N'-(2-methyl-6-(2H-1,2,3-triazol-2-yl)-5-(trifluoromethyl)pyridin-3-yl)urea | | 487.2 |
| 89 | (R)-N-(5-Chloro-6-(difluoromethoxy)-2-methylpyridin-3-yl)-N'-(4-(1-methoxyethyl)-6-methyl-1,5-naphthyridin-3-yl)urea | | 452.1 |
| 90 | (R)-N-(5-Chloro-2-methyl-6-(2H-1,2,3-triazol-2-yl)pyridin-3-yl)-N'-(4-(1-methoxyethyl)-6-methyl-1,5-naphthyridin-3-yl)urea | | 453.2 |
| 91 | (R)-N-(5-Chloro-6-(2H-1,2,3-triazol-2-yl)pyridin-3-yl)-N'-(4-(1-methoxyethyl)-6-methyl-1,5-naphthyridin-3-yl)urea | | 439.2 |
| 92 | (R)-N-(5-Chloro-6-(2H-1,2,3-triazol-2-yl)pyridin-3-yl)-N'-(4-(1-methoxyethyl)-6-methyl-1,5-naphthyridin-3-yl)urea | HCl | 439.2 |
| 93 | (S)-N-(4-(1-Methoxyethyl)-6-methyl-1,5-naphthyridin-3-yl)-N'-(2-methyl-6-(2H-1,2,3-triazol-2-yl)-5-(trifluoromethyl)pyridin-3-yl)urea | | 487.2 |
| 94 | (S)-N-(5-Chloro-6-(difluoromethoxy)-2-methylpyridin-3-yl)-N'-(4-(1-methoxyethyl)-6-methyl-1,5-naphthyridin-3-yl)urea | | 452.2 |
| 95 | (S)-N-(5-Chloro-2-methyl-6-(2H-1,2,3-triazol-2-yl)pyridin-3-yl)-N'-(4-(1-methoxyethyl)-6-methyl-1,5-naphthyridin-3-yl)urea | | 453.2 |
| 96 | (S)-N-(5-Chloro-6-(2H-1,2,3-triazol-2-yl)pyridin-3-yl)-N'-(4-(1-methoxyethyl)-6-methyl-1,5-naphthyridin-3-yl)urea | | 439.2 |
| 97 | (S)-N-(5-Chloro-6-(2H-1,2,3-triazol-2-yl)pyridin-3-yl)-N'-(4-(1-methoxyethyl)-6-methyl-1,5-naphthyridin-3-yl)urea | HCl | 439.2 |
| 98 | N-(2-Chloro-8-(propan-2-yl)imidazo[1,2-b]pyridazin-7-yl)-N'-(5-cyanopyridin-3-yl)urea | | 353.9 |

TABLE 1-8

| | | | |
|---|---|---|---|
| 99 | N-(2-Chloro-8-(propan-2-yl)imidazo[1,2-b]pyridazin-7-yl)-N'-(6-(2H-1,2,3-triazol-2-yl)-5-(trifluoromethyl)pyridin-3-yl)urea | HCOOH | 464.1 |
| 100 | N-(2-Chloro-8-(propan-2-yl)imidazo[1,2-b]pyridazin-7-yl)-N'-(5-chloro-6-(2H-1,2,3-triazol-2-yl)pyridin-3-yl)urea | HCOOH | 430.0 |
| 101 | N-(2-Chloro-8-(propan-2-yl)imidazo[1,2-b]pyridazin-7-yl)-N'-(5-cyano-6-(2H-1,2,3-triazol-2-yl)pyridin-3-yl)urea | HCOOH | 421.1 |
| 102 | N-(2-Chloro-8-(propan-2-yl)imidazo[1,2-b]pyridazin-7-yl)-N'-(3-cyano-1-methyl-1H-pyrazol-5-yl)urea | HCOOH | 357.0 |
| 103 | N-(2-Chloro-8-(propan-2-yl)imidazo[1,2-b]pyridazin-7-yl)-N'-(1-methyl-3-(trifluoromethyl)-1H-pyrazol-5-yl)urea | HCOOH | 400.0 |
| 104 | N-(2-Chloro-8-(propan-2-yl)imidazo[1,2-b]pyridazin-7-yl)-N'-(3,4-dicyanophenyl)urea | | 378.1 |
| 105 | N-(2-Chloro-8-(propan-2-yl)imidazo[1,2-b]pyridazin-7-yl)-N'-(5-cyano-6-methoxypyridin-3-yl)urea | | 384.0 |
| 106 | N-(5-Chloro-6-methoxypyridin-3-yl)-N'-(2-chloro-8-(propan-2-yl)imidazo[1,2-b]pyridazin-7-yl)urea | | 395.1 |
| 107 | N-(2-Chloro-8-(propan-2-yl)imidazo[1,2-b]pyridazin-7-yl)-N'-(3-(difluoromethoxy)-1-methyl-1H-pyrazol-5-yl)urea | | 398.0 |
| 108 | N-(2-Chloro-8-(propan-2-yl)imidazo[1,2-b]pyridazin-7-yl)-N'-(1-(difluoromethyl)-1H-pyrazol-4-yl)urea | | 368.0 |
| 109 | N-(5-Chloro-6-cyanopyridin-3-yl)-N'-(2-chloro-8-(propan-2-yl)imidazo[1,2-b]pyridazin-7-yl)urea | | 388.0 |
| 110 | N-(8-Chloroimidazo[1,2-a]pyridin-6-yl)-N'-(2-chloro-8-(propan-2-yl)imidazo[1,2-b]pyridazin-7-yl)urea | | 404.0 |
| 111 | N-(2-Chloro-8-(propan-2-yl)imidazo[1,2-b]pyridazin-7-yl)-N'-(6-cyano-5-(trifluoromethyl)pyridin-3-yl)urea | | 422.0 |
| 112 | N-(2-Chloro-8-(propan-2-yl)imidazo[1,2-b]pyridazin-7-yl)-N'-(6-cyano-5-(trifluoromethyl)pyridin-3-yl)urea | | 422.0 |

TABLE 1-9

| | | |
|---|---|---|
| 113 | N-(2-Chloro-8-(propan-2-yl)imidazo[1,2-b]pyridazin-7-yl)-N'-(3-(difluoromethyl)-1-methyl-1H-pyrazol-5-yl)urea | 382.0 |
| 114 | N-(3-Chloro-1-methyl-1H-pyrazol-5-yl)-N'-(2-chloro-8-(propan-2-yl)imidazo[1,2-b]pyridazin-7-yl)urea | 366.0 |
| 115 | N-(2-Chloro-8-(propan-2-yl)imidazo[1,2-b]pyridazin-7-yl)-N'-(1-(difluoromethyl)-3-methyl-1H-pyrazol-4-yl)urea | 384.0 |
| 116 | N-(2-Methyl-8-(propan-2-yl)imidazo[1,2-b]pyridazin-7-yl)-N'-(6-(2H-1,2,3-triazol-2-yl)-5-(trifluoromethyl)pyridin-3-yl)urea | 446.0 |
| 117 | N-(6-Chloro-5-(trifluoromethyl)pyridin-3-yl)-N'-(2-methyl-8-(propan-2-yl)imidazo[1,2-b]pyridazin-7-yl)urea | 413.1 |
| 118 | N-(2-Methyl-8-(propan-2-yl)imidazo[1,2-b]pyridazin-7-yl)-N'-(6-(1-methyl-1H-pyrazol-4-yl)-5-(trifluoromethyl)pyridin-3-yl)urea | 459.1 |
| 119 | N-(5-Chloro-6-(difluoromethoxy)pyridin-3-yl)-N'-(2-methyl-8-(propan-2-yl)imidazo[1,2-b]pyridazin-7-yl)urea | 410.9 |
| 120 | N-(6-Cyano-5-(trifluoromethyl)pyridin-3-yl)-N'-(2-methyl-8-(propan-2-yl)imidazo[1,2-b]pyridazin-7-yl)urea | 404.2 |
| 121 | N-(3-Chloro-4-methoxyphenyl)-N'-(2-methyl-8-(propan-2-yl)imidazo[1,2-b]pyridazin-7-yl)urea | 374.1 |
| 122 | N-(2-Methyl-8-(propan-2-yl)imidazo[1,2-b]pyridazin-7-yl)-N'-(2-(trifluoromethyl)pyridin-4-yl)urea | 379.2 |
| 123 | N-(3-Chloro-4-(trifluoromethoxy)phenyl)-N'-(2-methyl-8-(propan-2-yl)imidazo[1,2-b]pyridazin-7-yl)urea | 427.9 |
| 124 | N-(3-Chloro-4-(difluoromethoxy)phenyl)-N'-(2-methyl-8-(propan-2-yl)imidazo[1,2-b]pyridazin-7-yl)urea | 409.9 |
| 125 | N-(5-Chloro-6-(1-methyl-1H-pyrazol-3-yl)pyridin-3-yl)-N'-(2-methyl-8-(propan-2-yl)imidazo[1,2-b]pyridazin-7-yl)urea | 425.0 |
| 126 | N-(3-Chloro-4-(1H-1,2,4-triazol-1-yl)phenyl)-N'-(2-methyl-8-(propan-2-yl)imidazo[1,2-b]pyridazin-7-yl)urea | 411.0 |

TABLE 1-10

| | | |
|---|---|---|
| 127 | N-(5-Cyano-6-(difluoromethoxy)pyridin-3-yl)-N'-(2-methyl-8-(propan-2-yl)imidazo[1,2-b]pyridazin-7-yl)urea | 402.0 |
| 128 | N-(2-Chloro-8-(1-methoxyethyl)imidazo[1,2-b]pyridazin-7-yl)-N'-(3,4-dicyanophenyl)urea | 394.0 |
| 129 | N-(2-Chloro-8-(1-methoxyethyl)imidazo[1,2-b]pyridazin-7-yl)-N'-(5-cyanopyridin-3-yl)urea | 370.0 |
| 130 | N-(2-Chloro-8-(1-methoxyethyl)imidazo[1,2-b]pyridazin-7-yl)-N'-(5-cyano-6-methoxypyridin-3-yl)urea | 400.0 |

TABLE 1-10-continued

| | | |
|---|---|---|
| 131 | N-(2-Chloro-8-(1-methoxyethyl)imidazo[1,2-b]pyridazin-7-yl)-N'-(5-cyano-6-(2H-1,2,3-triazol-2-yl)pyridin-3-yl)urea | 437.1 |
| 132 | N-(2-Chloro-8-(1-methoxyethyl)imidazo[1,2-b]pyridazin-7-yl)-N'-(1-methyl-3-(trifluoromethyl)-1H-pyrazol-5-yl)urea | 415.9 |
| 133 | N-(2-Chloro-8-(1-methoxyethyl)imidazo[1,2-b]pyridazin-7-yl)-N'-(5-chloro-6-(2H-1,2,3-triazol-2-yl)pyridin-3-yl)urea | 447.9 |
| 134 | N-(2-Chloro-8-(1-methoxyethyl)imidazo[1,2-b]pyridazin-7-yl)-N'-(6-(2H-1,2,3-triazol-2-yl)-5-(trifluoromethyl)pyridin-3-yl)urea | 479.9 |
| 135 | N-(2-Chloro-8-(1-methoxyethyl)imidazo[1,2-b]pyridazin-7-yl)-N'-(6-(2H-1,2,3-triazol-2-yl)-5-(trifluoromethyl)pyridin-3-yl)urea | 479.9 |
| 136 | N-(2-Chloro-8-(1-methoxyethyl)imidazo[1,2-b]pyridazin-7-yl)-N'-(6-(2H-1,2,3-triazol-2-yl)-5-(trifluoromethyl)pyridin-3-yl)urea | 479.9 |
| 137 | N-(5-Chloro-6-(difluoromethoxy)pyridin-3-yl)-N'-(2-chloro-8-(1-methoxyethyl)imidazo[1,2-b]pyridazin-7-yl)urea | 444.9 |
| 138 | N-(2-Bromo-8-(1-methoxyethyl)imidazo[1,2-b]pyridazin-7-yl)-N'-(5-cyanopyridin-3-yl)urea | 414.0 |
| 139 | N-(5-Cyanopyridin-3-yl)-N'-(8-(1-methoxyethyl)-2-phenylimidazo[1,2-b]pyridazin-7-yl)urea | 414.1 |
| 140 | N-(5-Cyanopyridin-3-yl)-N'-(2-cyclopropyl-8-(1-methoxyethyl)imidazo[1,2-b]pyridazin-7-yl)urea | 378.1 |

TABLE 1-11

| | | | |
|---|---|---|---|
| 141 | N-(5-Cyanopyridin-3-yl)-N'-(2-methoxy-8-(1-methoxyethyl)imidazo[1,2-b]pyridazin-7-yl)urea | | 366.0 |
| 142 | N-(2-Cyano-8-(1-methoxyethyl)imidazo[1,2-b]pyridazin-7-yl)-N'-(5-cyanopyridin-3-yl)urea | | 361.1 |
| 143 | N-(5-Chloro-6-methoxypyridin-3-yl)-N'-(8-(1-methoxyethyl)-2-(trifluoromethyl)imidazo[1,2-b]pyridazin-7-yl)urea | | 445.1 |
| 144 | N-(5-Chloro-6-methoxypyridin-3-yl)-N'-(2-(difluoromethyl)-8-(1-methoxyethyl)imidazo[1,2-b]pyridazin-7-yl)urea | | 427.2 |
| 145 | N-(5-Chloro-6-(2H-1,2,3-triazol-2-yl)pyridin-3-yl)-N'-(2-(difluoromethyl)-8-(1-methoxyethyl)imidazo[1,2-b]pyridazin-7-yl)urea | | 464.1 |
| 146 | N-(5-Chloro-6-(2H-1,2,3-triazol-2-yl)pyridin-3-yl)-N'-(2-(difluoromethyl)-8-(1-methoxyethyl)imidazo[1,2-b]pyridazin-7-yl)urea | | 464.1 |
| 147 | N-(5-Chloro-6-(difluoromethoxy)pyridin-3-yl)-N'-(3-fluoro-8-(1-methoxyethyl)-2-methylimidazo[1,2-b]pyridazin-7-yl)urea | | 445.1 |
| 148 | N-(5-Chloro-6-(difluoromethoxy)pyridin-3-yl)-N'-(3-fluoro-8-(1-methoxyethyl)-2-methylimidazo[1,2-b]pyridazin-7-yl)urea | | 445.1 |
| 149 | N-(5-Chloro-6-(difluoromethoxy)pyridin-3-yl)-N'-(3-fluoro-8-(1-methoxyethyl)-2-methylimidazo[1,2-b]pyridazin-7-yl)urea | | 445.1 |
| 150 | N-(5-Chloro-6-(difluoromethoxy)pyridin-3-yl)-N'-(8-(2-methoxypropan-2-yl)-2-methylimidazo[1,2-b]pyridazin-7-yl)urea | | 441.1 |
| 151 | N-(5-Chloro-6-(2H-1,2,3-triazol-2-yl)pyridin-3-yl)-N'-(8-(1-methoxyethyl)imidazo[1,2-b]pyridazin-7-yl)urea | | 413.9 |
| 152 | N-(8-(1-Methoxyethyl)imidazo[1,2-b]pyridazin-7-yl)-N'-(6-(2H-1,2,3-triazol-2-yl)-5-(trifluoromethyl)pyridin-3-yl)urea | | 447.9 |
| 153 | N-(8-(2-Chlorophenyl)imidazo[1,2-b]pyridazin-7-yl)-N'-(2,4-difluorophenyl)urea | | 400.1 |
| 154 | N-(8-(2-Chlorophenyl)imidazo[1,2-b]pyridazin-7-yl)-N'-(2,4-difluorophenyl)urea | HCl | 400.1 |

TABLE 1-12

| | | |
|---|---|---|
| 155 | N-(3-Chloro-8-(2-chlorophenyl)imidazo[1,2-b]pyridazin-7-yl)-N'-(2,4-difluorophenyl)urea | 434.0 |
| 156 | N-(2-Chloro-8-(dimethylamino)imidazo[1,2-b]pyridazin-7-yl)-N'-(5-cyanopyridin-3-yl)urea | 355.0 |
| 157 | N-(2-Chloro-8-cyclopropylimidazo[1,2-b]pyridazin-7-yl)-N'-(5-cyanopyridin-3-yl)urea | 351.9 |
| 158 | N-(2-Chloro-8-ethylimidazo[1,2-b]pyridazin-7-yl)-N'-(5-cyanopyridin-3-yl)urea | 339.9 |
| 159 | N-(8-(Butan-2-yl)-2-chloroimidazo[1,2-b]pyridazin-7-yl)-N'-(5-cyanopyridin-3-yl)urea | 367.9 |
| 160 | N-(8-(Butan-2-yl)-2-chloroimidazo[1,2-b]pyridazin-7-yl)-N'-(5-chloro-6-(1H-1,2,3-triazol-1-yl)pyridin-3-yl)urea | 444.0 |
| 161 | N-(8-(Butan-2-yl)-2-chloroimidazo[1,2-b]pyridazin-7-yl)-N'-(5-chloro-6-(2H-1,2,3-triazol-2-yl)pyridin-3-yl)urea | 444.0 |
| 162 | N-(8-(Butan-2-yl)-2-chloroimidazo[1,2-b]pyridazin-7-yl)-N'-(6-(2H-1,2,3-triazol-2-yl)-5-(trifluoromethyl)pyridin-3-yl)urea | 478.1 |
| 163 | N-(8-(Butan-2-yl)-2-chloroimidazo[1,2-b]pyridazin-7-yl)-N'-(6-(1H-1,2,3-triazol-1-yl)-5-(trifluoromethyl)pyridin-3-yl)urea | 478.1 |
| 164 | N-(8-(Butan-2-yl)-2-chloroimidazo[1,2-b]pyridazin-7-yl)-N'-(1-methyl-3-(trifluoromethyl)-1H-pyrazol-5-yl)urea | 414.0 |
| 165 | N-(8-(Butan-2-yl)-2-chloroimidazo[1,2-b]pyridazin-7-yl)-N'-(3-cyano-1-methyl-1H-pyrazol-5-yl)urea | 373.1 |
| 166 | N-(8-(Butan-2-yl)-2-chloroimidazo[1,2-b]pyridazin-7-yl)-N'-(5-cyano-6-(2H-1,2,3-triazol-2-yl)pyridin-3-yl)urea | 435.0 |
| 167 | N-(8-(Butan-2-yl)-2-chloroimidazo[1,2-b]pyridazin-7-yl)-N'-(5-cyano-6-(2H-1,2,3-triazol-2-yl)pyridin-3-yl)urea | 435.1 |
| 168 | N-(8-(Butan-2-yl)-2-chloroimidazo[1,2-b]pyridazin-7-yl)-N'-(5-cyano-6-(2H-1,2,3-triazol-2-yl)pyridin-3-yl)urea | 435.1 |

TABLE 1-13

| | | |
|---|---|---|
| 169 | N-(8-(Butan-2-yl)-2-chloroimidazo[1,2-b]pyridazin-7-yl)-N'-(3-(difluoromethoxy)-1-methyl-1H-pyrazol-5-yl)urea | 412.1 |
| 170 | N-(8-(Butan-2-yl)-2-chloroimidazo[1,2-b]pyridazin-7-yl)-N'-(3-chloro-1-methyl-1H-pyrazol-5-yl)urea | 380.1 |
| 171 | N-(2-Chloro-8-(1,1,1-trifluoropropan-2-yl)imidazo[1,2-b]pyridazin-7-yl)-N'-(5-cyanopyridin-3-yl)urea | 408.0 |
| 172 | N-(2-Chloro-8-(1,1,1-trifluoropropan-2-yl)imidazo[1,2-b]pyridazin-7-yl)-N'-(3-cyano-1-methyl-1H-pyrazol-5-yl)urea | 411.1 |
| 173 | N-(5-Chloro-6-(difluoromethoxy)pyridin-3-yl)-N'-(2-chloro-8-(1,1,1-trifluoropropan-2-yl)imidazo[1,2-b]pyridazin-7-yl)urea | 483.0 |
| 174 | N-(2-Chloro-8-(1,1,1-trifluoropropan-2-yl)imidazo[1,2-b]pyridazin-7-yl)-N'-(6-(2H-1,2,3-triazol-2-yl)-5-(trifluoromethyl)pyridin-3-yl)urea | 518.1 |
| 175 | N-(2-Chloro-8-(1,1,1-trifluoropropan-2-yl)imidazo[1,2-b]pyridazin-7-yl)-N'-(5-cyano-6-(2H-1,2,3-triazol-2-yl)pyridin-3-yl)urea | 475.1 |
| 176 | N-(5-Chloro-6-methoxypyridin-3-yl)-N'-(2-chloro-8-(1,1,1-trifluoropropan-2-yl)imidazo[1,2-b]pyridazin-7-yl)urea | 447.0 |
| 177 | N-(2-Chloro-8-(1,1,1-trifluoropropan-2-yl)imidazo[1,2-b]pyridazin-7-yl)-N'-(1-methyl-3-(trifluoromethyl)-1H-pyrazol-5-yl)urea | 454.0 |
| 178 | N-(2-Chloro-8-(1,1,1-trifluoropropan-2-yl)imidazo[1,2-b]pyridazin-7-yl)-N'-(3-(difluoromethoxy)-1-methyl-1H-pyrazol-5-yl)urea | 452.0 |
| 179 | N-(5-Chloro-6-(2H-1,2,3-triazol-2-yl)pyridin-3-yl)-N'-(2-chloro-8-(1,1,1-trifluoropropan-2-yl)imidazo[1,2-b]pyridazin-7-yl)urea | 484.0 |
| 180 | N-(3-Chloro-1-methyl-1H-pyrazol-5-yl)-N'-(2-chloro-8-(1,1,1-trifluoropropan-2-yl)imidazo[1,2-b]pyridazin-7-yl)urea | 419.9 |
| 181 | N-(2-Chloro-8-(1-hydroxyethyl)imidazo[1,2-b]pyridazin-7-yl)-N'-(2,4-difluorophenyl)urea | 368.0 |
| 182 | N-(2-Chloro-8-(1-methoxypropan-2-yl)imidazo[1,2-b]pyridazin-7-yl)-N'-(5-cyanopyridin-3-yl)urea | HCOOH 384.0 |

TABLE 1-14

| | | |
|---|---|---|
| 183 | N-(2-Chloro-8-(3-chloro-1-methyl-1H-pyrazol-4-ypimidazo[1,2-b]pyridazin-7-yl)-N'-(5-cyanopyridin-3-yl)urea | HCOOH 428.1 |
| 184 | N-(2-Chloro-8-(3-chloro-1-methyl-1H-pyrazol-4-ypimidazo[1,2-b]pyridazin-7-yl)-N'-(5-cyano-6-methoxypyridin-3-yl)urea | 458.0 |
| 185 | N-(2-Chloro-8-(3-chloro-1-methyl-1H-pyrazol-4-ypimidazo[1,2-b]pyridazin-7-yl)-N'-(5-chloro-6-methoxypyridin-3-yl)urea | 466.9 |
| 186 | N-(1-Methyl-3-(trifluoromethyl)-1H-pyrazol-5-yl)-N'-(8-(propan-2-yl)imidazo[1,2-b]pyridazin-7-yl)urea | 366.0 |
| 187 | N-(6-Methoxy-4-(1-methoxyethyl)-1,5-naphthyridin-3-yl)-N'-(1-methyl-3-(trifluoromethyl)-1H-pyrazol-5-yl)urea | 425.1 |
| 188 | N-(6-Methoxy-4-(1-methoxyethyl)-1,5-naphthyridin-3-yl)-N'-(6-(2H-1,2,3-triazol-2-yl)-5-(trifluoromethyl)pyridin-3-yl)urea | 489.1 |
| 189 | N-(5-Chloro-6-(2H-1,2,3-triazol-2-yl)pyridin-3-yl)-N'-(6-methoxy-4-(1-methoxyethyl)-1,5-naphthyridin-3-yl)urea | 455.1 |
| 190 | N-(5-Chloro-6-(difluoromethoxy)pyridin-3-yl)-N'-(6-methoxy-4-(1-methoxyethyl)-1,5-naphthyridin-3-yl)urea | 454.0 |
| 191 | N-(5-Cyano-6-(2H-1,2,3-triazol-2-yl)pyridin-3-yl)-N'-(6-methoxy-4-(1-methoxyethyl)-1,5-naphthyridin-3-yl)urea | 446.2 |
| 192 | N-(5-Chloro-6-(difluoromethoxy)pyridin-3-yl)-N'-(4-(1-methoxyethyl)-6-(trifluoromethyl)-1,5-naphthyridin-3-yl)urea | 490.1 |
| 193 | N-(4-(1-Methoxyethyl)-6-(trifluoromethyl)-1,5-naphthyridin-3-yl)-N'-(6-(2H-1,2,3-triazol-2-yl)-5-(trifluoromethyl)pyridin-3-yl)urea | 525.1 |
| 194 | N-(5-Chloro-6-(2H-1,2,3-triazol-2-yl)pyridin-3-yl)-N'-(4-(1-methoxyethyl)-6-(trifluoromethyl)-1,5-naphthyridin-3-yl)urea | 491.1 |
| 195 | N-(4-(1-Methoxyethyl)-6-(trifluoromethyl)-1,5-naphthyridin-3-yl)-N'-(1-methyl-3-(trifluoromethyl)-1H-pyrazol-5-yl)urea | 461.1 |
| 196 | N-(5-Cyano-6-(2H-1,2,3-triazol-2-yl)pyridin-3-yl)-N'-(4-(1-methoxyethyl)-6-(trifluoromethyl)-1,5-naphthyridin-3-yl)urea | 482.1 |

TABLE 1-15

| | | |
|---|---|---|
| 197 | N-(5-Cyano-6-(2H-1,2,3-triazol-2-yl)pyridin-3-yl)-N'-(4-(1-methoxyethyl)-6-(trifluoromethyl)-1,5-naphthyridin-3-yl)urea | 484.1 |
| 198 | N-(5-Cyano-6-(2H-1,2,3-triazol-2-yl)pyridin-3-yl)-N'-(4-(1-methoxyethyl)-6-(trifluoromethyl)-1,5-naphthyridin-3-yl)urea | 484.1 |
| 199 | N-(5-Chloro-6-(difluoromethoxy)pyridin-3-yl)-N'-(4-(1-methoxyethyl)-1,5-naphthyridin-3-yl)urea | 424.1 |
| 200 | N-(5-Chloro-6-(2H-1,2,3-triazol-2-yl)pyridin-3-yl)-N'-(4-(1-methoxyethyl)-1,5-naphthyridin-3-yl)urea | 425.1 |
| 201 | N-(4-(1-Methoxyethyl)-1,5-naphthyridin-3-yl)-N'-(6-(2H-1,2,3-triazol-2-yl)-5-(trifluoromethyl)pyridin-3-yl)urea | 459.2 |
| 202 | N-(6-Chloro-4-(1-ethoxyethyl)-1,5-naphthyridin-3-yl)-N'-(6-(2H-1,2,3-triazol-2-yl)-5-(trifluoromethyl)pyridin-3-yl)urea | 506.8 |
| 203 | N-(6-(Difluoromethyl)-4-(1-methoxyethyl)-1,5-naphthyridin-3-yl)-N'-(6-(2H-1,2,3-triazol-2-yl)-5-(trifluoromethyl)pyridin-3-yl)urea | 509.2 |
| 204 | N-(6-Ethyl-4-(1-methoxyethyl)-1,5-naphthyridin-3-yl)-N'-(6-(2H-1,2,3-triazol-2-yl)-5-(trifluoromethyl)pyridin-3-yl)urea | 487.2 |
| 205 | N-(6-Ethyl-4-(1-methoxyethyl)-1,5-naphthyridin-3-yl)-N'-(6-(2H-1,2,3-triazol-2-yl)-5-(trifluoromethyl)pyridin-3-yl)urea | 487.2 |

TABLE 1-15-continued

| | | |
|---|---|---|
| 206 | N-(6-Chloro-4-(2-methoxypropan-2-yl)-1,5-naphthyridin-3-yl)-N'-(6-(2H-1,2,3-triazol-2-yl)-5-(trifluoromethyl)pyridin-3-yl)urea | 507.2 |
| 207 | N-(6-Chloro-4-(propan-2-yl)-1,5-naphthyridin-3-yl)-N'-(6-(2H-1,2,3-triazol-2-yl)-5-(trifluoromethyl)pyridin-3-yl)urea | 476.9 |
| 208 | N-(6-Chloro-4-(propan-2-yl)-1,5-naphthyridin-3-yl)-N'-(3-(1,1-difluoroethyl)-1-methyl-1H-pyrazol-5-yl)urea | 409.2 |
| 209 | N-(6-Chloro-4-(propan-2-yl)-1,5-naphthyridin-3-yl)-N'-(3-methyl-1(2,2,2-trifluoroethyl)-1H-pyrazol-5-yl)urea | 427.1 |
| 210 | N-(6-Chloro-4-(propan-2-yl)-1,5-naphthyridin-3-yl)-N'-(5-(difluoromethyl)-6-methoxypyridin-3-yl)urea | 422.1 |

TABLE 1-16

| | | |
|---|---|---|
| 211 | N-(6-Chloro-4-(propan-2-yl)-1,5-naphthyridin-3-yl)-N'-(1-(propan-2-yl)-3-(trifluoromethyl)-1H-pyrazol-5-yl)urea | 441.1 |
| 212 | N-(6-Chloro-4-(propan-2-yl)-1,5-naphthyridin-3-yl)-N'-(3,3-difluorocyclohexyl)urea | 383.2 |
| 213 | N-(6-Chloro-4-(propan-2-yl)-1,5-naphthyridin-3-yl)-N'-(3-(trifluoromethyl)cyclohexyl)urea | 415.1 |
| 214 | N-(6-Chloro-4-(propan-2-yl)-1,5-naphthyridin-3-yl)-N'-(5-chloro-6-(2H-1,2,3-triazol-2-yl)pyridin-3-yl)urea | 443.1 |
| 215 | N-(6-Chloro-4-(propan-2-yl)-1,5-naphthyridin-3-yl)-N'-(2-(trifluoromethyl)pyridin-4-yl)urea | 409.9 |
| 216 | N-(6-Chloro-4-(propan-2-yl)-1,5-naphthyridin-3-yl)-N'-(2-cyanopyridin-4-yl)urea | 366.9 |
| 217 | N-(5-Chloro-6-(difluoromethoxy)pyridin-3-yl)-N'-(6-chloro-4-(propan-2-yl)-1,5-naphthyridin-3-yl)urea | 441.9 |
| 218 | N-(6-Chloro-4-(propan-2-yl)-1,5-naphthyridin-3-yl)-N'-(5-(trifluoromethyl)pyridin-3-yl)urea | 409.9 |
| 219 | N-(6-Chloro-4-(propan-2-yl)-1,5-naphthyridin-3-yl)-N'-(6-methoxy-5-(trifluoromethyl)pyridin-3-yl)urea | 439.9 |
| 220 | N-(6-Chloro-4-(propan-2-yl)-1,5-naphthyridin-3-yl)-N'-(5-cyanopyridin-3-yl)urea | 366.9 |
| 221 | N-(6-Chloro-4-(propan-2-yl)-1,5-naphthyridin-3-yl)-N'-(5-chloro-6-(2,2,2-trifluoroethoxy)pyridin-3-yl)urea | 473.8 |
| 222 | N-(6-Chloro-4-(propan-2-yl)-1,5-naphthyridin-3-yl)-N'-(2-(difluoromethyl)pyridin-4-yl)urea | 390.1 |
| 223 | N-(6-Chloro-4-(propan-2-yl)-1,5-naphthyridin-3-yl)-N'-(2-(difluoromethoxy)pyridin-4-yl)urea | 408.1 |
| 224 | N-(5-Chloro-6-(difluoromethyl)pyridin-3-yl)-N'-(6-chloro-4-(propan-2-yl)-1,5-naphthyridin-3-yl)urea | 426.1 |

TABLE 1-17

| | | |
|---|---|---|
| 225 | N-(6-Chloro-4-(propan-2-yl)-1,5-naphthyridin-3-yl)-N'-(2-cyano-5-methylpyridin-4-yl)urea | 380.9 |
| 226 | N-(6-Chloro-4-(propan-2-yl)-1,5-naphthyridin-3-yl)-N'-(2-cyano-6-methylpyridin-4-yl)urea | 380.9 |
| 227 | N-(6-Chloro-4-(propan-2-yl)-1,5-naphthyridin-3-yl)-N'-(2-cyano-3-methylpyridin-4-yl)urea | 380.9 |
| 228 | N-(6-Chloro-4-(propan-2-yl)-1,5-naphthyridin-3-yl)-N'-(5-methyl-2-(trifluoromethyl)pyridin-4-yl)urea | 424.1 |
| 229 | N-(6-Chloro-4-(propan-2-yl)-1,5-naphthyridin-3-yl)-N'-(2-methyl-5-(trifluoromethyl)pyridin-4-yl)urea | 424.0 |
| 230 | N-(6-Chloro-4-(propan-2-yl)-1,5-naphthyridin-3-yl)-N'-(6-(1H-tetrazol-5-yl)-5-(trifluoromethyl)pyridin-3-yl)urea | 477.9 |
| 231 | N-(5-Bromo-2-(trifluoromethyl)pyridin-4-yl)-N'-(6-chloro-4-(propan-2-yl)-1,5-naphthyridin-3-yl)urea | 487.7 |
| 232 | N-(6-Chloro-4-(propan-2-yl)-1,5-naphthyridin-3-yl)-N'-(5-fluoro-2-(trifluoromethyl)pyridin-4-yl)urea | 427.9 |
| 233 | N-(6-Chloro-4-(propan-2-yl)-1,5-naphthyridin-3-yl)-N'-(5-chloro-2-(trifluoromethyl)pyridin-4-yl)urea | 443.9 |
| 234 | N-(6-Chloro-4-(propan-2-yl)-1,5-naphthyridin-3-yl)-N'-(2-methyl-6-(2H-1,2,3-triazol-2-yl)-5-(trifluoromethyl)pyridin-3-yl)urea | 490.9 |
| 235 | N-(6-Chloro-4-(propan-2-yl)-1,5-naphthyridin-3-yl)-N'-(5-chloro-6-(pyrimidin-2-yl)pyridin-3-yl)urea | 453.9 |
| 236 | N-(6-Chloro-4-(propan-2-yl)-1,5-naphthyridin-3-yl)-N'-(6-(1-methyl-1H-tetrazol-5-yl)-5-(trifluoromethyl)pyridin-3-yl)urea | 491.9 |
| 237 | N-(6-Chloro-4-(propan-2-yl)-1,5-naphthyridin-3-yl)-N'(6-(2-methyl-2H-tetrazol-5-yl)-5-(trifluoromethyl)pyridin-3-yl)urea | 491.9 |
| 238 | N-(5-Chloro-6-(difluoromethoxy)-2-methylpyridin-3-yl)-N'-(6-chloro-4-(propan-2-yl)-1,5-naphthyridin-3-yl)urea | 454.1 |

TABLE 1-18

| | | |
|---|---|---|
| 239 | N-(5-Chloro-2-methyl-6-(2H-1,2,3-triazol-2-yl)pyridin-3-yl)-N'-(6-chloro-4-(propan-2-yl)-1,5-naphthyridin-3-yl)urea | 457.1 |
| 240 | N-(6-Chloro-4-(propan-2-yl)-1,5-naphthyridin-3-yl)-N'-(2-methoxy-5-(trifluoromethyl)pyridin-3-yl)urea | 438.1 |
| 241 | N-(4-(Propan-2-yl)-1,5-naphthyridin-3-yl)-N'-(6-(2H-1,2,3-triazol-2-yl)-5-(trifluoromethyl)pyridin-3-yl)urea | 443.2 |
| 242 | N-(5-Chloro-6-(2H-1,2,3-triazol-2-yl)pyridin-3-yl)-N'-(4-(propan-2-yl)-1,5-naphthyridin-3-yl)urea | 409.1 |
| 243 | N-(6-Methyl-4-(propan-2-yl)-1,5-naphthyridin-3-yl)-N'-(6-(2H-1,2,3-triazol-2-yl)-5-(trifluoromethyl)pyridin-3-yl)urea | 456.9 |
| 244 | N-(5-Chloro-6-(2H-1,2,3-triazol-2-yl)pyridin-3-yl)-N'-(6-methyl-4-(propan-2-yl)-1,5-naphthyridin-3-yl)urea | 422.9 |
| 245 | N-(5-Chloro-6-(difluoromethoxy)pyridin-3-yl)-N'-(6-methyl-4-(propan-2-yl)-1,5-naphthyridin-3-yl)urea | 422.0 |
| 246 | N-(2-Cyano-5-methylpyridin-4-yl)-N'-(6-methyl-4-(propan-2-yl)-1,5-naphthyridin-3-yl)urea | 361.1 |
| 247 | N-(6-(2,2-Difluoroethoxy)-4-(propan-2-yl)-1,5-naphthyridin-3-yl)-N'-(6-(2H-1,2,3-triazol-2-yl)-5-(trifluoromethyl)pyridin-3-yl)urea | 522.9 |
| 248 | N-(6-(Difluoromethoxy)-4-(propan-2-yl)-1,5-naphthyridin-3-yl)-N'-(6-(2H-1,2,3-triazol-2-yl)-5-(trifluoromethyl)pyridin-3-yl)urea | 508.9 |
| 249 | N-(6-(Methoxymethyl)-4-(propan-2-yl)-1,5-naphthyridin-3-yl)-N'-(6-(2H-1,2,3-triazol-2-yl)-5-(trifluoromethyl)pyridin-3-yl)urea | 487.1 |
| 250 | N-(6-{((4-Methoxyphenyl)methoxy)methyl}-4-(propan-2-yl)-1,5-naphthyridin-3-yl)-N'-(6-(2H-1,2,3-triazol-2-yl)-5-(trifluoromethyl)pyridin-3-yl)urea | 593.2 |
| 251 | N-(6-(Hydroxymethyl)-4-(propan-2-yl)-1,5-naphthyridin-3-yl)-N'-(6-(2H-1,2,3-triazol-2-yl)-5-(trifluoromethyl)pyridin-3-yl)urea | 473.2 |
| 252 | N-(4-(2-Chlorophenyl)-1,5-naphthyridin-3-yl)-N'-(2,4-difluorophenyl)urea | 411.1 |

TABLE 1-19

| | | |
|---|---|---|
| 253 | N-(2-Chloro-8-(2-chlorophenyl)imidazo[1,2-b]pyridazin-7-yl)-N'-(2,4-difluorophenyl)urea | 434.0 |
| 254 | N-(4-(2-Chlorophenyl)-1,6-naphthyridin-3-yl)-N'-(2,4-difluorophenyl)urea | 411.1 |
| 255 | N-(5-Methoxy-4-(1-methoxyethyl)-1,6-naphthyridin-3-yl)-N'-(6-(2H-1,2,3-triazol-2-yl)-5-(trifluoromethyl)pyridin-3-yl)urea | 487.1 |
| 256 | N-(5-Chloro-6-(2H-1,2,3-triazol-2-yl)pyridin-3-yl)-N'-(5-methoxy-4-(1-methoxyethyl)-1,6-naphthyridin-3-yl)urea | 453.1 |
| 257 | N-(5-Cyanopyridin-3-yl)-N'-(5-methoxy-4-(1-methoxyethyl)-1,6-naphthyridin-3-yl)urea | 377.1 |
| 258 | N-(5-Chloro-4-(1-methoxyethyl)-1,6-naphthyridin-3-yl)-N'-(5-chloro-6-(2H-1,2,3-triazol-2-yl)pyridin-3-yl)urea | 457.0 |
| 259 | N-(5-Chloro-6-(difluoromethoxy)pyridin-3-yl)-N'-(5-methyl-4-(propan-2-yl)-1,6-naphthyridin-3-yl)urea | 422.2 |
| 260 | N-(5-Chloro-6-(difluoromethoxy)pyridin-3-yl)-N'-(4-(1-methoxyethyl)-5-methyl-1,6-naphthyridin-3-yl)urea | 438.1 |
| 261 | N-(4-(1-Methoxyethyl)-5-methyl-1,6-naphthyridin-3-yl)-N'-(6-(2H-1,2,3-triazol-2-yl)-5-(trifluoromethyl)pyridin-3-yl)urea | 473.2 |
| 262 | N-(4-(1-Methoxyethyl)-5-methyl-1,6-naphthyridin-3-yl)-N'-(6-(2H-1,2,3-triazol-2-yl)-5-(trifluoromethyl)pyridin-3-yl)urea | 473.2 |
| 263 | N-(4-(1-Methoxyethyl)-5-methyl-1,6-naphthyridin-3-yl)-N'-(6-(2H-1,2,3-triazol-2-yl)-5-(trifluoromethyl)pyridin-3-yl)urea | 473.2 |
| 264 | N-(5-Chloro-6-(2H-1,2,3-triazol-2-yl)pyridin-3-yl)-N'-(4-(1-methoxyethyl)-5-methyl-1,6-naphthyridin-3-yl)urea | 439.1 |
| 265 | N-(5-Chloro-6-(2H-1,2,3-triazol-2-yl)pyridin-3-yl)-N'-(4-(1-methoxyethyl)-5-methyl-1,6-naphthyridin-3-yl)urea | 439.1 |
| 266 | N-(5-Chloro-6-(2H-1,2,3-triazol-2-yl)pyridin-3-yl)-N'-(4-(1-methoxyethyl)-5-methyl-1,6-naphthyridin-3-yl)urea | 439.1 |

TABLE 1-20

| | | |
|---|---|---|
| 267 | N-(5-Chloro-6-(2H-1,2,3-triazol-2-yl)pyridin-3-yl)-N'-(4-(1-methoxyethyl)-5-methyl-6-oxo-5,6-dihydro-1,5-naphthyridin-3-yl)urea | 455.2 |
| 268 | N-(4-(1-Methoxyethyl)-5-methyl-6-oxo-5,6-dihydro-1,5-naphthyridin-3-yl)-N'-(6-(2H-1,2,3-triazol-2-yl)-5-(trifluoromethyl)pyridin-3-yl)urea | 489.2 |
| 269 | N-(4-(1-Methoxyethyl)-5-methyl-6-oxo-5,6-dihydro-1,5-naphthyridin-3-yl)-N'-(6-(2H-1,2,3-triazol-2-yl)-5-(trifluoromethyl)pyridin-3-yl)urea | 489.2 |
| 270 | N-(5-Chloro-6-methoxypyridin-3-yl)-N'-(4-(1-methoxyethyl)-6-methyl-5-oxo-5,6-dihydro-1,6-naphthyridin-3-yl)urea | 418.0 |

Preparation Example 1 (Production of Capsules)

| | | |
|---|---|---|
| 1) Compound of Example 1 | 30 mg | |
| 2) Fine powdered cellulose | 10 mg | |
| 3) Lactose | 19 mg | |
| 4) Magnesium stearate | 1 mg | |
| Total | 60 mg | |

1), 2), 3) and 4) are mixed and filled in a gelatin capsule.

Preparation Example 2 (Production of Tablets)

| | | |
|---|---|---|
| 1) Compound of Example 1 | 30 g | |
| 2) Lactose | 50 g | |
| 3) Corn starch | 15 g | |
| 4) Carboxymethyl cellulose calcium | 44 g | |
| 5) Magnesium stearate | 1 g | |
| 1000 tablets Total | 140 g | |

The whole amount of 1), 2) and 3), and 30 g of 4) are knead with water and vacuum dried, followed by granulation. With this grain-sized powder are mixed 14 g of 4) and 1 g of 5), followed by tableting with a tableting machine. In this way, 1000 tablets are obtained containing 30 mg of the compound of Example 1 per tablet.

Test Example 1

Preparation of recombinant human MALT1 protein

On the human MALT1 gene, PCR was carried out using GC-030-D09 (pENTR221/MALT1, GeneCopoeia) as a template with primers having BamH I restriction enzyme at the N-terminal and Not I restriction enzyme at the C-terminal to form a human MALTI (340-789aa) dimer. On the leucine zipper gene of yeast GCN4, PCR was carried out using yeast DNA as a template with primers having Nde I restriction enzyme at the N-terminal, and a linker sequence (GGAAGTGGCTCAGGTAGC (SEQ ID NO: 1)) and BamH I restriction enzyme at the C-terminal to yield yeast GCN4 (251-281aa). Both of the obtained fragments were treated with the restriction enzymes, and inserted between Nde I and Not I of a pET28a (Novagen) vector to yield a recombinant human MALT1 protein expression vector pET28a/His-LZ-hMALTlvl (340-789)-His.

The recombinant human MALT1 protein was prepared by transforming the expression plasmid prepared as above with ECOS Competent *E. coli* BL21 (DE3) (Nippon Gene Co., Ltd.). *Escherichia coli* obtained by transformation was inoculated into 300 mL of LB medium (1% tryptone, 0.5% yeast extract, 0.5% sodium chloride, 0.01% ampicillin) and cultured at 30° C. for 16 hours. The obtained culture solution was transplanted into ajar culture tank containing 6 L of a main fermentation medium (0.3% potassium dihydrogen phosphate, 0.6% disodium hydrogen phosphate, 0.1% ammonium chloride, 0.05% sodium chloride, 0.024% magnesium sulfate, 0.01% Antifoam PE-L, 1.5% sorbitol, 1.5% casamino acid, 0.5% yeast extract and 0.01% ampicillin), and the culturing was started at 37° C., aeration rate of 5 L/min, and stirring rotation speed of 400 rpm. When the turbidity of the culture solution reached about 500 Klett units, the culture temperature was lowered to 16° C., and then isopropyl-β-D-thiogalactopyranoside (IPTG) was added to a final concentration of 0.1 mM. Furthermore, culturing was carried out for 16 hours to induce expression of human MALT1 protein. After completion of the culture, the culture solution was centrifuged at 5,000 rpm for 10 minutes. After suspending the obtained human MALT1 protein-expressing *Escherichia coli* in a buffer solution containing 50 mM Tris-HCl pH 8.0, 300 mM NaCl, 5 mM DTT, 5 U/ml benzonase, 20 mM imidazole, 10% glycerol and 0.1% NP-40, sonication was carried out using Sonifier (Branson). This crushed liquid was centrifuged (15,300×G, 30 min, TOMY MX-301), and the obtained supernatant was passed through and adsorbed to a Ni-NTA Superflow (QIA-GEN) column previously equilibrated with 50 mM Tris-HCl pH 8.0, 300 mM NaCl, 5 mM DTT and 10% glycerol, followed by elution in a buffer containing 50 mM Tris-HCl pH 8.0, 300 mM NaCl, 5 mM DTT, 10% glycerol and 250 mM imidazole. Furthermore, gel filtration was carried out on a Superdex 200 pg column previously equilibrated with a buffer solution containing 50 mM Tris-HCl pH 8.0, 150 mM NaCl, 5 mM DTT and 10% glycerol to collect a target fraction, and equal amounts of 50 mM Tris-HCl pH 8.0, 150 mM NaCl, 5 mM DTT and 90% glycerol were added to yield purified human MALT1 protein. The prepared protein was stored at −30° C., and the protein concentration was measured with a BCA Protein Assay Kit (PIERCE) using BSA as a standard.

Measurement of MALT1 enzyme inhibitory activity

To a 384 well black plate (Greiner) was added 2 μL of a compound solution diluted with an assay buffer ((20 mM HEPES (Dojin Laboratories), 10 mM KCl (Wako Pure Chemical Industries, Ltd.), 1.5 mM MgCl$_2$ (Sigma-Aldrich), 1 mM EDTA (pH 8.0) (Nippon Gene Co., Ltd.), 0.01% Triton X-100 (Sigma-Aldrich) and 1 mM DTT (Wako Pure Chemical Industries, Ltd.)). Subsequently, 2 μL of a purified recombinant human MALT1 enzyme solution was added, followed by incubation for 60 minutes at room temperature. To the mixture were added 2 μL of a substrate solution (75 μM Ac-LRSR-AFC (SM Biochemicals), 20 mM HEPES (Dojin Laboratories), 10 mM KCl (Wako Pure Chemical Industries, Ltd.), 1.5 mM MgCl$_2$ (Sigma-Aldrich), 1 mM EDTA (pH 8.0) (Nippon Gene Co., Ltd.), 0.01% Triton X-100 (Sigma-Aldrich) and 1 mM DTT (Wako Pure Chemical Industries, Ltd.), followed by incubation for 60 minutes at room temperature. The fluorescence values of excitation 400 nm and emission 485 nm immediately after substrate addition and after enzymatic reaction were measured with a plate reader Envision (PerkinElmer), and the fluorescence values increased by enzymatic reaction were used for calculation of the inhibition rate (%). The inhibition rate (%) was calculated regarding the value without enzyme addition as 100% and the value without compound addition as 0%.

The measurement results of MALT1 enzyme inhibitory activity are shown below.

TABLE 2

| Example No. | MALT1 enzyme inhibition rate (%) at 3 μM compound |
|---|---|
| 1 | 104 |
| 2 | 99 |
| 3 | 101 |
| 4 | 111 |
| 5 | 99 |
| 6 | 108 |
| 7 | 98 |
| 8 | 94 |
| 9 | 99 |
| 22 | 104 |
| 31 | 103 |
| 35 | 105 |
| 36 | 101 |
| 59 | 95 |

TABLE 2-continued

| Example No. | MALT1 enzyme inhibition rate (%) at 3 µM compound |
|---|---|
| 66 | 99 |
| 133 | 99 |
| 173 | 99 |
| 255 | 97 |
| 261 | 98 |
| 269 | 99 |
| 270 | 94 |

From these results, it has been indicated that the compound of the present invention has MALT1 enzyme inhibitory activity.

Test Example 2

Measurement of growth inhibitory activity using OCI-Ly3 cells

OCI-Ly3 cells were seeded in a cell culture medium IMDM (Fujifilm Wako Pure Chemical Corporation) containing 20% FCS (fetal calf serum, Thermo Fisher Scientific) and monothioglycerol (Fujifilm Wako Pure Chemical Corporation) so as to be at $1.25 \times 10^3$ cells/well on a 96-well plate. Cell Titer-Glo solution (Promega) was added to cells to which the test compound had not been added, followed by stirring at room temperature for 15 minutes. Subsequently, the luminescence value was measured with Envision (PerkinElmer) on the day of seeding. Cells to which the test compound dissolved in dimethyl sulfoxide (Fujifilm Wako Pure Chemical Corporation) had been added were allowed to stand in a $CO_2$ incubator (37° C.) for 6 days. Subsequently, the luminescence value was measured in the same manner. The inhibition rate (%) of the test compound on OCI-Ly3 cell growth was calculated by the following formula.

Cell growth inhibition rate (%)=(1−(Luminescent value on day 6 of test compound treatment—Luminescent value before test compound treatment)/(Luminescent value on day 6 without compound addition—Luminescent value before compound treatment))×100

The measurement results of the cell growth inhibition rate are shown below.

TABLE 3

| Example No. | Cell growth inhibition rate (%) at 3 µM compound |
|---|---|
| 1 | 96 |
| 2 | 97 |
| 3 | 99 |
| 4 | 97 |
| 5 | 93 |
| 6 | 99 |
| 7 | 95 |
| 9 | 99 |
| 22 | 102 |
| 31 | 96 |
| 35 | 95 |
| 36 | 96 |
| 59 | 98 |
| 66 | 100 |
| 133 | 98 |
| 173 | 85 |
| 255 | 99 |
| 261 | 88 |
| 269 | 95 |
| 270 | 40 |

From these results, it has been indicated that the compound of the present invention inhibits cell growth.

Test Example 3

Antitumor effect on OCI-Ly3 cell-bearing cancer model

Human diffuse large-cell B-cell lymphoma cells OCI-Ly3 (DSMZ, German Collection of Microorganisms and Cell Cultures) were suspended in a Matrigel (BD Biosciences):HBSS (Thermo Fisher Scientific)=1:1 solution, and $1 \times 10^7$ cells were transplanted subcutaneously into the abdomen of NOG female mice (CLEA Japan, Inc.). The tumor diameter of the engrafted tumor was measured, and the tumor volume was calculated by the following formula.

Tumor volume=major axis×minor axis×minor axis×(1/2)

Individuals with the engrafted tumor having a tumor volume of about 120 mm³ were selected, and 6 animals per group were used in the experiment. A suspension of the test compound in 0.5% methylcellulose solution (Fujifilm Wako Pure Chemical Corporation) was orally administered at a dose of 10 mg/kg (10 mL/kg) twice daily for 3 weeks. The tumor volume was measured on the day before the start of administration and every 3 to 4 days over time, and the tumor diameter was finally measured the day after the end of administration for 21 days to calculate the tumor volume. The tumor growth of the test compound-administered group compared with the control-administered group was calculated by the following formula as an average tumor volume increase ratio T/C.

T/C=((Tumor volume after the end of administration for the test compound-administered group−Tumor volume of the day before the start of administration for the test compound-administered group)/(Tumor volume after the end of administration for the control-administered group−Tumor volume of the day before the start of administration for the control-administered group))×100

The T/C of the test compound is shown below.

TABLE 4

| Example No. | Dose (mg/kg) | T/C (%) |
|---|---|---|
| 1 | 10 | 13.4 |
| 2 | 10 | 2.0 |
| 3 | 10 | 38.7 |
| 4 | 10 | 43.3 |

From these results, it has been indicated that the compound of the present invention has an antitumor effect in human diffuse large-cell B-cell lymphoma cell OCI-Ly3-subcutaneously transplanted models.

INDUSTRIAL APPLICABILITY

The compound of the present invention can have an effect of inhibiting MALT1 and is expected as useful as a prophylactic or therapeutic drug for cancer etc.

This application is based on Japanese Patent Application No. 2018-222530 filed in Japan, the content of which is incorporated herein by reference in its entirety.

The invention claimed is:

1. A pharmaceutical composition comprising a compound or a salt thereof, or a co-crystal, a hydrate, or a solvate thereof, wherein the compound is (S)-N-(6-chloro-4-(1-methoxyethyl)-1,5-naphthyridin-3-yl)-N'-(6-(2H-1,2,3-triazol-2-yl)-5-(trifluoromethyl)pyridin-3-yl)urea.

2. A pharmaceutical composition comprising a compound or a salt thereof, wherein the compound is (S)-N-(6-chloro-4-(1-methoxyethyl)-1,5-naphthyridin-3-yl)-N'-(6-(2H-1,2,3-triazol-2-yl)-5-(trifluoromethyl)pyridin-3-yl)urea.

3. A pharmaceutical composition comprising a compound of the following structure:

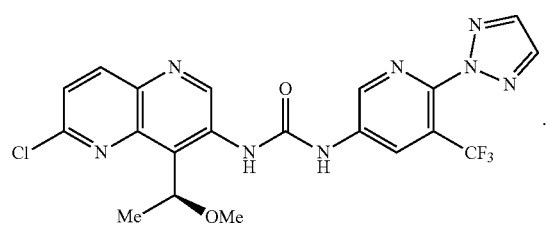 [SMILES: CO[C@@H](C)c1c(NC(=O)Nc2cnc(-n3nccn3)c(C(F)(F)F)c2)cnc2ccc(Cl)nc12]

4. A pharmaceutical composition comprising a salt of a compound of the following structure:

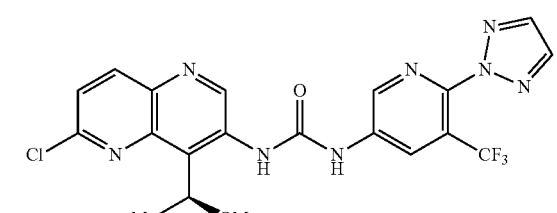

* * * * *